US007888381B2

(12) United States Patent
Duan et al.

(10) Patent No.: US 7,888,381 B2
(45) Date of Patent: Feb. 15, 2011

(54) MODULATORS OF GLUCOCORTICOID RECEPTOR, AP-1, AND/OR NF-κB ACTIVITY, AND USE THEREOF

(75) Inventors: Jingwu Duan, Yardley, PA (US); Zhonghui Lu, King of Prussia, PA (US); David S. Weinstein, East Windsor, NJ (US); Bin Jiang, Norristown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 632 days.

(21) Appl. No.: 11/451,660

(22) Filed: Jun. 13, 2006

(65) Prior Publication Data

US 2007/0129400 A1 Jun. 7, 2007

Related U.S. Application Data

(60) Provisional application No. 60/690,355, filed on Jun. 14, 2005, provisional application No. 60/782,636, filed on Mar. 15, 2006.

(51) Int. Cl.
*C07D 231/56* (2006.01)
*A01N 43/56* (2006.01)

(52) U.S. Cl. .................................... 514/406; 548/360.1

(58) Field of Classification Search ........................ None
See application file for complete search history.

(56) References Cited

U.S. PATENT DOCUMENTS

| | | | |
|---|---|---|---|
| 3,452,085 A | 6/1969 | Francesco et al. |
| 3,736,332 A | 5/1973 | Butula |
| 4,166,131 A | 8/1979 | Payne |
| 6,083,969 A | 7/2000 | Ferro et al. |
| 2005/0090529 A1 | 4/2005 | McAlpine et al. |

FOREIGN PATENT DOCUMENTS

| | | |
|---|---|---|
| DE | 2354610 A1 | 5/1974 |
| EP | 0474991 A1 | 3/1992 |
| JP | 54141768 | 11/1979 |
| JP | 55 019226 | 2/1980 |
| WO | WO 01/02369 | 1/2001 |
| WO | WO 02/10137 | 2/2002 |
| WO | WO 03/035625 | 5/2003 |
| WO | WO 03/061651 | 7/2003 |
| WO | WO 03/086294 | 10/2003 |
| WO | WO 2004/009017 | 1/2004 |
| WO | WO 2004/010995 | 2/2004 |
| WO | WO 2004/075840 | 9/2004 |
| WO | WO 2004/094388 | 11/2004 |
| WO | WO 2005/095353 | 10/2005 |

OTHER PUBLICATIONS

Auwers et al., caplu san 1924:6075.*
Hamed, A.A. et al., "Reactivity of 4,6-Diacetylcyclohexenones Towards Some Nucleophilic Reagents", Egypt. J. Chem., vol. 29, No. 4, pp. 485-493 (1986).
Salem, M.A.I. et al., "Some Reactions with Cinnamoyl Cyclohexenone Derivatives", Egypt. J. Chem., vol. 30, No. 1, pp. 89-95 (1987).
Nagakura, et al., Journal of Medicinal Chemistry, vol. 22, No. 1, pp. 48-52, (1979).
Chaloner, et al., Tetrahedron, vol. 48, No. 37, pp. 8101-8116 (1992).
Chemical Abstracts, Heterocycles, 36(12), 2839-50, (1993).
Chemical Abstracts, Heterocycles, 37(2), 967-78 (1994).
Chemical Abstracts, Chemie, 36B(9), 1147-8 (1981).
Chemical Abstracts, Indian Journal of Chemistry, 15(8), 690-3 (1977).
Chemical Abstracts, Indian Journal of Chemistry, 15B(4), 359-63 (1977).
Chemical Abstracts, Zh. Org. Khim.; vol. 1, 2232-2236 (1965).
Chemical Abstracts, Farmaco, vol. 47, No. 3, 357-365 (1992).
Chemical Abstracts, Justus Liebigs Ann., vol. 287, p. 149, (1895).
Chemical Abstracts, Tetrahedron, vol. 26, 5793-5801 (1970).
Chemical Abstracts, Eur. Journal of Organic Chemistry, vol. 9, 1673-1680 (2001).
Chemical Abstracts, Tetrahedron Lett., vol. 34, No. 31, 4957-4960 (1993).
Chemical Abstracts, Journal of the Chemical Society, vol. 10, 2749-2750 (1990).
Chemical Abstracts, Recl. Tray. Chim. Pays-Bas, vol. 77, 792-798, (1958).
Chemical Abstracts, Can. J. Chem., vol. 50, 726-736, (1972).
CAS Registry No. 344573-23-5 (no references).
CAS Registry No. 116373-85-4 (no references).
Baldwin, Jr., A.S., "The transcription factor NF-κB and human disease", The Journal of Clinical Investigation, vol. 107, No. 1, pp. 3-6 (2001).

(Continued)

*Primary Examiner*—Joseph McKane
*Assistant Examiner*—Sun Jae Y Loewe
(74) *Attorney, Agent, or Firm*—Burton Rodney; Laurelee A. Duncan

(57) ABSTRACT

Non-steroidal compounds are provided which are useful in treating diseases associated with modulation of the glucocorticoid receptor, AP-1, and/or NF-κB activity including obesity, diabetes, inflammatory and immune diseases, and have the structure of formula (I)

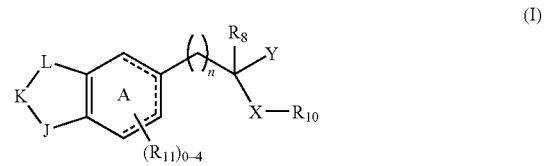

(I)

or an enantiomer, a diastereomer, a pharmaceutically acceptable salt, or hydrate thereof, where J is selected from $NR_1$ or $C(R_4)(R_{4a})$; K is selected from $NR_2$ or $C(R_5)(R_{5a})$; L is selected from $NR_3$ or $C(R_6)(R_{6a})$; and A, X, Y, $R_1$, $R_2$, $R_3$, $R_4$, $R_{4a}$, $R_5$, $R_{5a}$, $R_6$, $R_{6a}$, $R_8$, $R_{10}$, $R_{11}$, and n are defined herein. Also provided are pharmaceutical compositions and methods of treating obesity, diabetes and inflammatory or immune associated diseases comprising said compounds.

6 Claims, No Drawings

OTHER PUBLICATIONS

Bekhit, A.A. et al., "Non-Steroidal anti-inflammatory agents: Synthesis of novel benzopyrazolyl, benzoxazolyl and quinazolinyl derivatives of 4(3H)-quinazolinones", Pharmazie, vol. 53, No. 8, pp. 539-543 (1998).

Bouillon, J.-P. et al., "Spiroannelation Starting from β-Trifluoroacetylpyrrolidone", Polish J. Chem., vol. 68, pp. 2315-2322 (1994).

Burke, J.R., "Targeting IκB kinase for the treatment of inflammatory and other disorders", Current Opinion in Drug Discovery & Development, vol. 6, No. 5, pp. 720-728 (2003).

Caldenhoven, E. et al., "Negative Cross-Talk between RelA and the Glucocorticoid Receptor: A Possible Mechanism for the Antiinflammatory Action of Glucocorticoids", Molecular Endocrinology, vol. 9, No. 4, pp. 401-412 (1995).

Chakravarti, D. et al., "Role of CBP/P300 in nuclear receptor signalling", Nature, vol. 383, pp. 99-103 (1996).

Diamond, M.I. et al., "Transcription Factor Interactions: Selectors of Positive or Negative Regulation from a Single DNA Element", Science, vol. 249, pp. 1266-1272 (1990).

Elkasaby, M.A., "Some Reactions of 6-Acetyl-5-aryl-4-carbethoxy-3-methylcyclohex-2-enones", Indian Journal of Chemistry, vol. 15B, pp. 690-693 (1977).

Firestein, G.S. et al., "Signal Transduction and Transcription Factors in Rheumatic Disease", Arthritis & Rheumatism, vol. 42, No. 4, pp. 609-621 (1999).

Hamed, A.A. et al., "Reactivity of 4,6-Diacetylcyclohexenones Towards Some Nucleophilic Reagents", Polish Journal of Chemistry, vol. 59, pp. 1161-1166 (1985).

Jonat, C. et al., "Antitumor Promotion and Antiinflammation: Down-Modulation of AP-1 (Fos/Jun) Activity by Glucocorticoid Hormone", Cell, vol. 62, pp. 1189-1204 (1990).

Kamei, Y. et al., "A CBP Integrator Complex Mediates. Transcriptional Activation and AP-1 Inhibition by Nuclear Receptors", Cell, vol. 85, pp. 403-414 (1996).

Manning, A.M. et al., "Targeting JNK for Therapeutic Benefit: From Junk to Gold", Nature Reviews Drug Discovery, vol. 2, pp. 554-565 (2003).

Miesfeld, R. et al., "Characterization of a steroid hormone receptor gene and mRNA in wild-type and mutant cells", Nature, vol. 312, pp. 779-781 (1984).

Peltz, G., "Transcription factors in immune-mediated disease", Current Opinion in Biotechnology, vol. 8, pp. 467-473 (1997).

Reichardt, H.M. et al., "DNA Binding of the Glucocorticoid Receptor Is Not Essential for Survival", Cell, vol. 93, pp. 531-541 (1998).

Reichardt, H.M. et al., "Repression of inflammatory responses in the absence of DNA binding by the glucocorticoid receptor", The EMBO Journal, vol. 20, No. 24, pp. 7168-7173 (2001).

Weinberger, C. et al., "Domain structure of human glucocorticoid receptor and its relationship to the v-erb-A oncogene product", Nature, vol. 318, pp. 670-672 (1985).

Weinberger, C. et al., "Identification of Human Glucocorticoid Receptor Complementary DNA Clones by Epitope Selection", Science, vol. 228, pp. 740-742 (1985).

Yang-Yen, H.-F. et al., "Transcriptional Interference between c-Jun and the Glucocorticoid Receptor: Mutual Inhibition of DNA Binding Due to Direct Protein-Protein Interaction", Cell, vol. 62, pp. 1205-1215 (1990).

* cited by examiner

MODULATORS OF GLUCOCORTICOID RECEPTOR, AP-1, AND/OR NF-κB ACTIVITY, AND USE THEREOF

This application claims priority from U.S. Provisional Application Ser. Nos. 60/690,355 and 60/782,636 filed Jun. 14, 2005 and Mar. 15, 2006, respectively.

FIELD OF THE INVENTION

The present invention relates to new non-steroidal compounds which are effective modulators of the glucocorticoid receptor, AP-1, and/or NF-κB activity and thus are useful in treating diseases such as obesity, diabetes and inflammatory or immune associated diseases, and to a method for using such compounds to treat these and related diseases.

BACKGROUND OF THE INVENTION

The transcription factors NF-κB and AP-1 are involved in regulating the expression of a number of genes involved in mediating inflammatory and immune responses. NF-κB regulates the transcription of genes including TNF-α, IL-1, IL-2, IL-6, adhesion molecules (such as E-selectin) and chemokines (such as Rantes), among others. AP-1 regulates the production of the cytokines TNF-α, IL-1, IL-2, as well as, matrix metalloproteases. Drug therapies targeting TNF-α, a gene whose expression is regulated by both NF-κB and AP-1, have been shown to be highly efficacious in several inflammatory human diseases including rheumatoid arthritis and Crohn's disease. Accordingly, NF-κB and AP-1 play key roles in the initiation and perpetuation of inflammatory and immunological disorders. See Baldwin, A S, *Journal of Clin. Investigation*, 107, 3 (2001); Firestein, G. S., and Manning, A. M., *Arthritis and Rheumatism*, 42, 609 (1999); and Peltz, G., *Curr. Opin, in Biotech.* 8, 467 (1997).

There are many signaling molecules (kinases and phosphatases) upstream of AP-1 and NF-κB which are potential therapeutic drug targets. The kinase JNK plays an essential role in regulating the phosphorylation and subsequent activation of c-jun, one of the subunits which constitute the AP-1 complex (fos/c-jun). Compounds which inhibit JNK have been shown to be efficacious in animal models of inflammatory disease. See Manning A M and Davis R J, *Nature Rev. Drug Disc.*, V. 2, 554 (2003). A kinase critical to the activation of NF-κB is the IκB kinase (IKK). This kinase plays a key role in the phosphorylation of IκB. Once IκB is phosphorylated it undergoes degradation leading to the release of NF-κB which can translocate into the nucleus and activate the transcription of the genes described above. An inhibitor of IKK, BMS-345541, has been shown to be efficacious in animal models of inflammatory disease. See Burke J R., *Curr Opin Drug Discov Devel.*, September; 6(5), 720-8, (2003).

In addition to inhibiting signaling cascades involved in the activation of NF-κB and AP-1, the glucocorticoid receptor has been shown to inhibit the activity of NF-κB and AP-1 via direct physical interactions. The glucocorticoid receptor (GR) is a member of the nuclear hormone receptor family of transcription factors, and a member of the steroid hormone family of transcription factors. Affinity labeling of the glucocorticoid receptor protein allowed the production of antibodies against the receptor which facilitated cloning the glucocorticoid receptors. For results in humans see Weinberger, et al., *Science* 228, 640-742, (1985); Weinberger, et al., *Nature*, 318, 670-672 (1986) and for results in rats see Miesfeld, R., *Nature*, 312, 779-781, (1985).

Glucocorticoids which interact with GR have been used for over 50 years to treat inflammatory diseases. It has been clearly shown that glucocorticoids exert their anti-inflammatory activity via the inhibition by GR of the transcription factors NF-κB and AP-1. This inhibition is termed transrepression. It has been shown that the primary mechanism for inhibition of these transcription factors by GR is via a direct physical interaction. This interaction alters the transcription factor complex and inhibits the ability of NF-κB and AP-1 to stimulate transcription. See Jonat, C., et al., *Cell*, 62, 1189 (1990); Yang-Yen, H. F., et al., *Cell*, 62, 1205 (1990); Diamond, M. I., et al., *Science* 249, 1266 (1990); and Caldenhoven, E,. et al., *Mol. Endocrinol.*, 9, 401 (1995). Other mechanisms such as sequestration of co-activators by GR have also been proposed. See Kamer Y., et al., *Cell*, 85, 403 (1996); and Chakravarti, D., et al., *Nature*, 383, 99 (1996).

In addition to causing transrepression, the interaction of a glucocorticoid with GR can cause GR to induce transcription of certain genes. This induction of transcription is termed transactivation. Transactivation requires dimerization of GR and binding to a glucocorticoid response element (GRE).

Recent studies using a transgenic GR dimerization defective mouse which cannot bind DNA have shown that the transactivation (DNA binding) activities of GR could be separated from the transrepressive (non-DNA binding) effect of GR. These studies also indicate that many of the side effects of glucocorticoid therapy are due to the ability of GR to induce transcription of various genes involved in metabolism, whereas, transrepression, which does not require DNA binding leads to suppression of inflammation. See Tuckermann, J. et al., *Cell*, 93, 531 (1998) and Reichardt, H M, *EMBO J.*, 20, 7168 (2001).

PCT application WO 2004/009017 published Jan. 29, 2004, assigned to Applicant and incorporated herein by reference in its entirety, describes substituted bicyclooctane compounds useful in treating diseases such as obesity, diabetes and inflammatory or immune associated diseases.

In addition, a number of patent applications, including WO 03/086294 and WO04/075840, published Oct. 23, 2003 and Sep. 10, 2004, respectively, both assigned to Merck and Co., Inc, as well as WO 03/061651, published Jul. 31, 2003 and assigned to The Regents of the U. of CA, describe compounds having a fused tricyclic ring system that are said to be useful in treating diseases associated with binding to the glucocorticoid receptor, including autoimmune and inflammatory diseases and conditions.

Compounds that modulate AP-1 and/or NF-κB activity would be useful as such compounds would be useful in the treatment of inflammatory and immune diseases and disorders such as osteoarthritis, rheumatoid arthritis, multiple sclerosis, asthma, inflammatory bowel disease, transplant rejection and graft vs. host disease.

Also, with respect to the glucocorticoid receptor pathway, it is known that glucocorticoids are potent anti-inflammatory agents, however their systemic use is limited by side effects. Compounds that retain the anti-inflammatory efficacy of glucocorticoids while minimizing the side effects such as diabetes, osteoporosis and glaucoma would be of great benefit to a very large number of patients with inflammatory diseases.

Additionally concerning GR, the art is in need of compounds that antagonize transactivation. Such compounds may be useful in treating metabolic diseases associated with increased levels of glucocorticoid, such as diabetes, osteoporosis and glaucoma.

Additionally concerning GR, the art is in need of compounds that cause transactivation. Such compounds may be useful in treating metabolic diseases associated with a deficiency in glucocorticoid. Such diseases include Addison's disease.

Also, there is a need for new compounds with improved activity compared with known modulators of GR, AP-1, and/or NF-κB activity. It is also desirable and preferable to find compounds with advantageous and improved characteristics in one or more categories, which may be, but are not limited to, the following: (a) pharmaceutical properties; (b) dosage requirements; (c) factors which decrease blood concentration peak-to-trough characteristics; (d) factors that increase the concentration of active drug at the receptor; (e) factors that decrease the liability for clinical drug-drug interactions; (f) factors that decrease the potential for adverse side-effects; (g) factors that improve manufacturing costs or feasibility and (h) factors leading to desirable physical characteristics.

DESCRIPTION OF THE INVENTION

The present invention relates to new non-steroidal compounds which are which are particularly effective modulators of the glucocorticoid receptor, AP-1, and/or NF-κB activity and thus are useful in treating diseases such as obesity, diabetes and inflammatory or immune associated diseases, and to a method and composition for using such compounds to treat these and related diseases.

In accordance with the present invention, compounds are provided having the structure of formula (I)

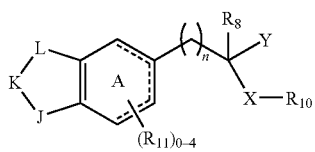

or an enantiomer, a diastereomer, or a pharmaceutically acceptable salt thereof, wherein:
----- is a single or double bond;
A is a partially saturated ring;
n is 0, 1, or 2;
J is $NR_1$ or $C(R_4)(R_{4a})$;
K is $NR_2$ or $C(R_5)(R_{5a})$;
L is $NR_3$ or $C(R_6)(R_{6a})$;
X is a bond, alkylene, alkenylene, alkynylene, —C(O), —N($R_{14}$)—, —N($R_{14}$)alkylene-, —Oalkylene-, —N($R_{14}$)—C(O)—, —N($R_{14}$)—C(O)O—, —$NR_{15}$C(O) $NR_{16}$, —S(O)$_t$—

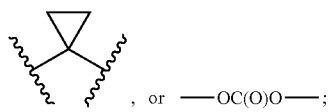, or —OC(O)O—;

Y is selected from hydrogen, halogen, nitro, cyano; $OR_{12}$, $NR_{12}R_{13}$, $C(=O)R_{12}$, $CO_2R_{12}$, $C(=O)NR_{12}R_{13}$, O—C(=O)$NR_{12}R_{13}$, —O—C(=O)$R_{12}$, $NR_{12}C(=O)R_{13}$, $NR_{12}C(O)OR_{13}$, $NR_{12}C(O)N(R_{13})_2$, $NR_{12}C(S)OR_{13}$, S(O)$_p R_{20}$, $NR_{12}S(O)_p N(R_{13})_2$, $NR_{12}S(O)_p R_{20}$, and S(O)$_p NR_{12}R_{13}$; or Y is taken together with $R_8$ to form an oxo, a substituted alkenyl, or an unsubstituted alkenyl;

$R_1$ is selected from (i) alkyl, substituted alkyl, alkenyl, substituted alkenyl, alkynyl, substituted alkynyl, $OR_{14}$, $NR_{14}S(O)_p R_{21}$, cycloalkyl, heterocyclo, aryl, and heteroaryl; and/or (ii) $R_1$ is taken together with $R_2$ or $R_2$ is taken together with $R_3$ to form a double bond;

$R_2$, and $R_3$ are independently selected from (i) hydrogen, alkyl, substituted alkyl, alkenyl, substituted alkenyl, alkynyl, substituted alkynyl, $OR_{14}$, $NR_{14}S(O)_p R_{21}$, cycloalkyl, heterocyclo, aryl, and heteroaryl; and/or (ii) $R_1$ is taken together with $R_2$ or $R_2$ is taken together with $R_3$ to form a double bond;

$R_4$, $R_{4a}$, $R_5$, $R_{5a}$, $R_6$, and $R_{6a}$ are independently selected from (i) hydrogen, halogen, alkyl, substituted alkyl, alkenyl, substituted alkenyl, alkynyl, substituted alkynyl, nitro, azide, cyano, $OR_{15}$, $NR_{15}R_{16}$, $C(=O)R_{15}$, $CO_2R_{15}$, $C(=O)NR_{15}R_{16}$, O—C(=O)$NR_{12}R_{13}$, —O—C(=O)$R_{15}$, $NR_{15}C(=O)R_{16}$, $NR_{15}C(O)OR_{16}$, $NR_{15}C(S)OR_{16}$, S(O)$_q R_{22}$, $NR_{15}S(O)_q R_{22}$, S(O)$_q NR_{15}R_{16}$, cycloalkyl, heterocyclo, aryl, and heteroaryl; and/or (ii) $R_4$ may be taken together with $R_{4a}$, and/or $R_5$ may be taken together with $R_{5a}$, and/or $R_6$ may be taken together with $R_{6a}$ to form an oxo, alkenyl, or substituted alkenyl group; and/or (iii) each one of $R_4$, $R_{4a}$, $R_5$, $R_{5a}$, $R_6$, and $R_{6a}$ is taken together with any one of $R_4$, $R_{4a}$, $R_5$, $R_{5a}$, $R_6$, and $R_{6a}$ located on an adjacent carbon atom to form a double bond or a fused ring; or when J is $NR_2$, and/or K is $NR_2$, and/or L is $NR_3$, each one of $R_1$, $R_2$, and/or $R_3$ is taken together with one of $R_4$, $R_{4a}$, $R_5$, $R_{5a}$, $R_6$, and $R_{6a}$ which is located on an adjacent carbon atom to form a double bond;

$R_8$ and $R_{10}$ are independently selected from (i) hydrogen, alkyl, substituted alkyl, alkenyl, substituted alkenyl, alkynyl, substituted alkynyl, $OR_{17}$, S(O)$_r R_{23}$, $NR_{17}S(O)_r R_{23}$, cycloalkyl, heterocyclo, aryl, and heteroaryl; or (ii) $R_8$ is taken together with $R_{10}$ to form a cycloalkyl, heterocyclo, aryl, and heteroaryl ring; and/or (iii) $R_8$ is taken together with Y to form an oxo, alkenyl, or a substituted alkenyl group;

$R_{11}$ at each occurrence is independently selected from (i) alkyl, substituted alkyl, alkenyl, substituted alkenyl, alkynyl, substituted alkynyl, halogen, nitro, azide, cyano, $OR_{19}$, cycloalkyl, -heterocyclo, aryl, and heteroaryl; and/or (ii) two $R_1$ groups located on the same carbon atom are taken together to form an oxo, alkenyl, or a substituted alkenyl group;

$R_{12}$, $R_{13}$, $R_{14}$, $R_{15}$, $R_{16}$, $R_{17}$, $R_{18}$, and $R_{19}$ at each occurrence are independently selected from (i) hydrogen, alkyl, substituted alkyl, alkenyl, substituted alkenyl, alkynyl, substituted alkynyl, cycloalkyl, aryl, heteroaryl, and heterocyclo; or (ii) $R_{12}$ is taken together with $R_{13}$ and/or $R_{15}$ is taken together with $R_{16}$ to form a heteroaryl or heterocyclo ring;

$R_{20}$, $R_{21}$, $R_{22}$, and $R_{23}$ are independently selected from alkyl, substituted alkyl, alkenyl, substituted alkenyl, alkynyl, substituted alkynyl, cycloalkyl, aryl, heteroaryl, and heterocyclo; and p, q, r and t are independently selected from 0, 1 and 2.

Preferred embodiments of the compounds are within the scope of formula (I) and are described in paragraphs 1-14, below. Aspects of each embodiment may be combined with other embodiments to form other preferred embodiments.

1. A compound, or an enantiomer, a diastereomer, a pharmaceutically acceptable salt, or hydrate thereof, wherein J is $NR_1$; K is $NR_2$; L is $C(R_6)(R_{6a})$; and $R_2$ and $R_{6a}$ are joined together to form a double bond.

2. A compound, within the scope of embodiment 1, or an enantiomer, a pharmaceutically acceptable salt, or hydrate thereof, wherein an optional double bond shown in ring A of the compound of Formula I is present.

3. A compound, within the scope of embodiments 1 or 2, or an enantiomer, a diastereomer, a pharmaceutically acceptable salt, or hydrate thereof, wherein:

$R_1$ is cycloalkyl, aryl, heterocyclo, or heteroaryl, said cycloalkyl, aryl, heterocyclo, or heteroaryl is substituted with from one up to the maximum number of substitutable positions with a substituent independently selected from hydrogen, halogen, nitro, cyano, $C_{1-6}$alkyl, substituted $C_{1-6}$alkyl, $C_{2-6}$alkenyl, substituted $C_{2-6}$alkenyl, $C_{2-6}$alkynyl, substituted $C_{2-6}$alkynyl, $OR_a$, $C(=O)NR_aR_b$, $C(=O)R_a$, $CO_2R_a$, $O-C(=O)NR_aR_b$, $C(=O)NR_aR_b$, $-O-C(=O)R_a$, $NR_aC(=O)R_b$, $NR_aC(O)OR_b$, $NR_8C(S)OR_b$, $S(O)_sR_c$, $NR_aS(O)_sR_c$, $S(O)_pNR_aR_b$, cycloalkyl, heterocyclo, aryl, and heteroaryl;

$R_a$ and $R_b$ at each occurrence are independently selected from (i) hydrogen, alkyl, substituted alkyl, alkenyl, substituted alkenyl, alkynyl, substituted alkynyl, cycloalkyl, aryl, heteroaryl, and heterocyclo; or (ii) $R_a$ is taken together with $R_b$ to form a heteroaryl or heterocyclo ring;

$R_c$ is selected from alkyl, substituted alkyl, alkenyl, substituted alkenyl, alkynyl, substituted alkynyl, cycloalkyl, aryl, heteroaryl, and heterocyclo; and s is 1 or 2.

More preferably, $R_1$ is aryl or heteroaryl, each of which is substituted with 1-3 groups selected from hydrogen, halogen, nitro, cyano, $C_{1-6}$alkyl, substituted $C_{1-6}$alkyl, $OR_a$, $NR_aR_b$, $C(=O)NR_aR_b$, $S(O)_sW$, $NR_aS(O)_sR_c$, $S(O)_pNR_aR_b$, and $C_{3-7}$cycloalkyl. Even more preferably, $R_1$ is aryl (e.g. phenyl, napthyl, etc.) or a nitrogen containing heteroaryl (e.g. pyridyl, pyradizinyl, etc.) substituted by 1-3 groups selected from hydrogen, halogen, amido, cyano, nitro, trifluoromethyl, or $C_{1-4}$alkyl (particularly where $R_1$ is phenyl substituted by 1-2 halogens, preferably fluoro).

4. A compound within the scope of embodiments 1, 2, or 3, or an enantiomer, a diastereomer, a pharmaceutically acceptable salt, or hydrate thereof, wherein:

X is a bond, alkylene, $-N(R_{14})-$, $-N(R_{14})$alkylene-, $-N(R_{14})C(O)-$, $-O$alkylene-, $-NR_{15}C(O)NR_{16}-$, $-S(O)_t-$, $-OC(O)NH-$, or $-OC(O)O-$ (preferably X is a bond, alkylene, or $-N(R_{14})C(O)-$);

Y is (i) hydrogen, $OR_{12}$, $NR_{12}R_{13}$, or $O-C(=O)NR_{12}R_{13}$; or (ii) Y together with $R_8$ combines to form oxo or alkenyl (preferably Y is (i) hydrogen or $OR_{12}$; or (ii) Y is taken together with $R_8$ to form oxo);

$R_8$ is (i) hydrogen, alkyl, substituted alkyl; or (ii) $R_8$ together with Y forms oxo or alkenyl; or (iii) $R_8$ together with $R_{10}$ combines to form heterocyclo (preferably $R_8$ is (i) hydrogen, alky or substituted alkyl; or (ii) $R_8$ is taken together with Y to form oxo);

$R_{10}$ is (i) hydrogen, hydroxy, alkyl, substituted alkyl, alkenyl, substituted alkenyl, alkynyl, or substituted alkynyl; or (ii) cycloalkyl, aryl, heterocyclo, or heteroaryl; wherein said cycloalkyl, aryl, heterocyclo, or heteroaryl is optionally substituted with from one up to the maximum number of substitutable positions with a substituent independently selected from the group consisting of halogen, nitro, cyano, $C_{1-6}$alkyl, oxo, N-oxide, substituted $C_{1-6}$alkyl, $C_{2-6}$alkenyl, substituted $C_{2-6}$alkenyl, $C_{2-6}$alkynyl, substituted $C_{2-6}$alkynyl, $OR_d$, $NR_dR_e$, $C(=O)R_d$, $CO_2R_d$, $-O-C(=O)NR_dR_e$, $C(=O)NR_dR_e$, $-O-C(=O)R_d$, $NR_dC(=O)R_e$, $N_dC(O)OR_e$, $NR_dC(S)OR_e$, $S(O)_vR_f$, $NR_dS(O)_vR_f$, $S(O)_vNR_dR_e$, cycloalkyl, heterocyclo, aryl, and heteroaryl (preferably $R_{10}$ is cycloalkyl, heterocyclo, aryl or heteroaryl, each group of which is optionally substituted);

$R_d$ and $R_e$ at each occurrence are independently selected from (i) hydrogen, alkyl, substituted alkyl, alkenyl, substituted alkenyl, alkynyl, substituted alkynyl, cycloalkyl, aryl, heteroaryl, and heterocyclo; and/or (ii) $R_d$ is taken together with $R_e$ to form a heteroaryl or heterocyclo ring;

$R_f$ is selected from hydrogen, alkyl, substituted alkyl, alkenyl, substituted alkenyl, alkynyl, substituted alkynyl, cycloalkyl, aryl, heteroaryl, and heterocyclo; and v is 1 or 2.

5. A compound, within the scope of embodiments 1, 2, 3 or 4, or an enantiomer, a diastereomer, a pharmaceutically acceptable salt, or hydrate thereof, wherein X is a bond, alkylene, alkenylene, alkynylene, $-C(O)$, $-N(R_{14})-$, $-N(R_{14})-C(O)-$, or

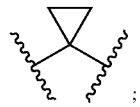

Y is selected from hydrogen, halogen, nitro, cyano; $OR_{12}$, $NR_{12}R_{13}$, $C(=O)R_{12}$, $CO_2R_{12}$, $C(=O)NR_{12}R_{13}$, $O-C(=O)NR_{12}R_{13}$, $-O-C(=O)R_{12}$, $NR_{12}C(=O)R_{13}$, $NR_{12}C(O)OR_{13}$, $NR_{12}C(S)OR_{13}$, $S(O)_pR_{20}$, $NR_{12}S(O)_pN(R_{13})_2$, $NR_{12}S(O)_pR_{20}$, and $S(O)_pNR_{12}R_{13}$;

$R_8$ and $R_{10}$ are independently selected from (i) hydrogen, alkyl, substituted alkyl, alkenyl, substituted alkenyl, alkynyl, substituted alkynyl, $OR_{17}$, $S(O)_rR_{23}$, $NR_{17}S(O)_rR_{23}$, cycloalkyl, heterocyclo, aryl, and heteroaryl; or (ii) $R_8$ may be taken together with $R_{10}$ to form a ring;

$R_{11}$ at each occurrence is independently selected from alkyl, substituted alkyl, alkenyl, substituted alkenyl, halogen, cyano, nitro, $OR_{19}$, cycloalkyl, heterocyclo, aryl, and heteroaryl; and p, q, and r are independently selected from 1 and 2.

6. A compound, within the scope of embodiments 1, 2, 3, 4, or 5, having formula II:

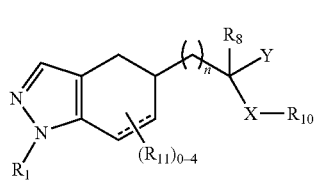

II or an enantiomer, a diastereomer, or a pharmaceutically acceptable salt thereof.

7. A compound, within the scope of embodiments 1, 2, 3, 4, 5, or 6, or an enantiomer, a diastereomer, a pharmaceutically acceptable salt, or hydrate thereof, wherein X is a (i) a bond, alkylene, $-N(R_{14})-$, $-N(R_{14})$alkylene-, $-N(R_{14})C(O)-$, $-O$alkylene-, $-NR_{15}C(O)NR_{16}-$, $-S(O)_t-$, $-OC(O)N(R_{14})-$, or $-OC(O)O-$ (X is preferably a bond or $-C(=O)N(R_{14})-$;

Y is (i) hydrogen, $OR_{12}$, $NR_{12}R_{13}$, or $O-C(=O)NR_{12}R_{13}$; or (ii) Y is taken together with $R_8$ to form oxo or alkenyl (Y is preferably (i) $OR_{12}$; or (ii) Y is taken together with $R_8$ to form oxo);

$R_1$ is aryl substituted with 1-3 groups selected from hydrogen, halogen, nitro, cyano, $C_{1-6}$alkyl, substituted $C_{1-6}$alkyl, $OR_a$, $NR_aR_b$, $C(=O)NR_aR_b$, $S(O)_sR_c$, $NR_aS(O)_sR_c$, $S(O)_p NR_aR_b$, and $C_{3-7}$cycloalkyl; $R_8$ is (i) hydrogen, $C_{1-6}$alkyl, or substituted $C_{1-6}$alkyl; or (ii) $R_8$ is taken together with Y to form oxo or alkenyl; or (iii) $R_8$ is combined with $R_{10}$ to form a heterocyclo;

$R_{10}$ is (i) hydrogen, hydroxy, alkyl, substituted alkyl, alkenyl, substituted alkenyl, alkynyl, or substituted alkynyl; or (ii) cycloalkyl, aryl, heterocyclo, or heteroaryl; said cycloalkyl, aryl, heterocyclo, or heteroaryl optionally substituted with from one up to the maximum number of substitutable positions with substituents independently selected from halogen, nitro, cyano, $C_{1-6}$alkyl, oxo, N-oxide, substituted $C_{1-6}$alkyl, $C_{2-6}$alkenyl, substituted $C_{2-6}$alkenyl, $C_{2-6}$alkynyl, substituted $C_{2-6}$alkynyl, $OR_d$, $NR_dR_e$, C(=O)$R_d$, $CO_2R_d$, —O—C(=O)$NR_dR_e$, C(=O)$NR_dR_e$, —O—C(=O)$R_d$, $NR_dC$(=O)$R_e$, $NR_dC(O)OR_e$, $NR_dC(S)OR_e$, $S(O)_vR_f$, $NR_dS(O)_vR_f$, $S(O)_vNR_dR_e$, cycloalkyl, heterocyclo, aryl, and heteroaryl (preferably $R_{10}$ is cycloalkyl, heterocyclo, aryl or heteroaryl; said cycloalkyl, heterocyclo, aryl or heteroaryl optionally substituted with one substituent chosen from halogen, CN, $NR_dR_e$, N-oxide, $C_{1-6}$alkyl, substituted $C_{1-6}$alkyl (especially substituted methylene), OH, $OC_{1-6}$alkyl, $OCF_3$, $CF_3$, phenyl, pyrrolyl, morpholinyl, —O (optionally substituted phenyl), or —O (optionally substituted benzyl)); or (iii) $R_8$ is combined with $R_{10}$ to form benozdioxinyl or dioxolanyl);

each $R_{11}$ is (i) independently selected from hydrogen, halogen, cyano, nitro, $C_{1-6}$alkyl, substituted $C_{1-6}$alkyl, cycloalkyl, $OR_{19}$, $C_{2-6}$alkenyl, substituted $C_{2-6}$alkenyl, and $C_{3-6}$cycloalkyl; and/or (ii) two $R_{11}$ groups located on the same carbon atom are taken together to form an oxo group;

$R_{12}$ and $R_{13}$ are independently selected from hydrogen, $C_{1-6}$alkyl, substituted $C_{1-6}$alkyl, $C_{2-6}$alkenyl, substituted $C_{2-6}$alkenyl, $C_{2-6}$alkynyl, substituted $C_{2-6}$alkynyl, $C_{3-7}$cycloalkyl, $C_{2-6}$alkenyl, or acetyl;

$R_a$, $R_b$, $R_d$ and $R_e$ at each occurrence are independently selected from (i) hydrogen, alkyl, substituted alkyl, alkenyl, substituted alkenyl, alkynyl, substituted alkynyl, cycloalkyl, aryl, heteroaryl, and heterocyclo; or (ii) $R_a$ is taken together with $R_b$ and/or $R_d$ is taken together with $R_e$ to form a heteroaryl or heterocyclo ring;

$R_e$ and $R_f$ at each occurrence are independently selected from alkyl, substituted alkyl, alkenyl, substituted alkenyl, alkynyl, substituted alkynyl, cycloalkyl, aryl, heteroaryl, and heterocyclo; and v is 1 or 2.

8. A compound within the scope of embodiments 1, 2, 3, 4, 5, 6 or 7, an enantiomer, a diastereomer, a pharmaceutically acceptable salt, or hydrate thereof, wherein:

n is 0 or 1;

X is a (i) a bond; or (ii) $C_{1-4}$alkylene or $C_{2-4}$alkenylene, each of which is substituted with one to three groups selected from hydrogen, halogen, OH, $OCH_3$, and $OCF_3$;

Y is $OR_{12}$;

$R_8$ is (i) hydrogen, $C_{1-6}$alkyl, or substituted $C_{1-6}$alkyl; or (ii) $R_8$ is combined with Y to form =O;

$R_{10}$ is selected from the group consisting of: (i) hydroxy, $C_{1-6}$alkyl, substituted $C_{1-6}$alkyl, $C_{2-6}$alkenyl, substituted $C_{2-6}$alkenyl, $C_{2-6}$alkynyl, substituted $C_{2-6}$alkynyl, and $C_{3-6}$cycloalkyl; or (ii) phenyl, phenylsulfonyl, napthyl, quinolinyl, pyrrolyl, pyridyl, thiazolyl, benzothiazolyl, thienyl, benzothienyl, furyl, and benzofuryl, each group of which is optionally further substituted by one up to the maximum number of substitutable positions with a substituent independently selected from halogen, CN, $NR_dR_e$, $C_{1-6}$alkyl, OH, $OC_{1-6}$alkyl, $OCF_3$, $CF_3$, —O (optionally substituted phenyl), or —O (optionally substituted benzyl);

$R_d$ and $R_e$ are independently selected (i) from hydrogen, $C_{1-6}$alkyl, and substituted $C_{1-6}$alkyl; or (ii) $R_d$ is taken together with $R_e$ to form a heteroaryl or heterocyclo ring;

each $R_{11}$ is independently selected from $C_{1-6}$alkyl, substituted $C_{1-6}$alkyl, $C_{2-6}$alkenyl, substituted $C_{2-6}$alkenyl, and $C_{3-6}$cycloalkyl; and $R_{12}$ is hydrogen or $C_{1-6}$alkyl.

9. A compound within the scope of embodiments 1, 2, 3, 4, 5, 6, or 7, an enantiomer, a diastereomer, a pharmaceutically acceptable salt, or hydrate thereof, having formula III:

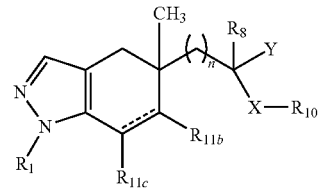

III wherein:

$R_1$ is phenyl substituted with 1-3 groups selected from halogen, nitro, cyano, methyl, methoxy, ethoxy, nitro, cyano, and $CF_3$, particularly where the substituents are one to two halogens, especially fluoro;

$R_{11b}$ and $R_{11c}$ are independently selected from hydrogen, halogen, nitro, cyano, $C_{1-6}$alkyl, substituted $C_{1-6}$alkyl, $C_{2-6}$alkenyl, substituted $C_{2-6}$alkenyl, and $C_{3-7}$cycloalkyl.

10. A compound within the scope of embodiments 1, 2, 3, 4, 5, 6, 7 and 9, an enantiomer, a diastereomer, a pharmaceutically acceptable salt, or hydrate thereof, wherein:

X is a bond, alkylene, or —N($R_{14}$)—;

Y is (i) hydrogen or $OR_{12}$; or (ii) Y is taken together with $R_8$ to form oxo;

$R_8$ is (i) hydrogen, $CF_3$, or $CH_3$; or (ii) $R_8$ is taken together with Y to form oxo.

$R_{10}$ is selected from the group consisting of: (i) hydrogen, hydroxy, $C_{1-6}$alkyl, substituted $C_{1-6}$alkyl, $C_{2-6}$alkenyl, substituted $C_{2-6}$alkenyl, $C_{2-6}$alkynyl, substituted $C_{2-6}$alkynyl, and $C_{3-6}$cycloalkyl; or (ii) cyclopentyl, cyclohexyl, phenyl, phenylsulfonyl, napthyl, quinolinyl, pyrrolyl, pyridyl, thiazolyl, thiadiazolyl, benzothiazolyl, thienyl,, benzothienyl, furyl, 1,3-dihydroisobenzofuryl, and benzofuryl, each group of which is optionally further substituted by one up to the maximum number of substitutable positions with a substituent independently selected from halogen, CN, $N_dR_e$, N-oxide, $C_{1-6}$alkyl, substituted $C_{1-6}$alkyl, OH, $OC_{1-6}$alkyl, $OCF_3$, $CF_3$, phenyl, pyrrolyl, morpholinyl, —O (optionally substituted phenyl), or —O (optionally substituted benzyl); or (iii) $R_8$ is combined with $R_{10}$ to form benozdioxinyl or dioxolanyl; and $R_{14}$ is selected from hydrogen, $C_{1-6}$alkyl, and —C(O)$C_{1-6}$alkyl;

v is 1 or 2.

11. Compounds within the scope of embodiments 1-7 and 9-10, an enantiomer, a diastereomer, a pharmaceutically acceptable salt, or hydrate thereof, wherein:

X is a bond, methylene, ethylene, butylene, or —N($R_{14}$)—;

$R_{12}$ and $R_{13}$ are independently selected from hydrogen, $C_{1-6}$alkyl, substituted $C_{1-6}$alkyl, acetyl, $C_{2-6}$alkenyl, and —OC(O)NH$C_{1-6}$alkyl;

$R_{14}$ is selected from hydrogen, ethyl, and —C(O)Me;

$R_d$ and $R_e$ are independently (i) hydrogen, $C_{1-6}$alkyl, or substituted $C_{1-6}$alkyl; or (ii) $R_d$ is taken together with $R_e$ to form a heteroaryl or heterocyclo ring;

$R_f$ is selected from hydrogen, alkyl, substituted alkyl, alkenyl, substituted alkenyl, alkynyl, substituted alkynyl, cycloalkyl, aryl, heteroaryl, and heterocyclo; and v is 1 or 2.

12. Compounds within the scope of embodiments 1-7 and 9-11, of formula (IV):

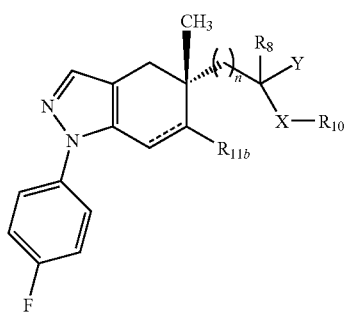

or an enantiomer, a diastereomer, or a pharmaceutically acceptable salt thereof.

13. Compounds within the scope of embodiments 1-7 and 9-12, or an enantiomer, a diastereomer, or a pharmaceutically acceptable salt thereof, wherein:

X is a bond;
Y is $-OC_{1-6}$alkyl or $-OC_{2-6}$alkenyl;
$R_8$ is hydrogen;
$R_{10}$ is an optionally substituted phenyl group;
$R_{11b}$ is $C_{1-6}$alkyl; and
n is 1.

14. Compounds within the scope of embodiments 1-7 and 9-12, or an enantiomer, a diastereomer, or a pharmaceutically acceptable salt thereof, wherein:

X is $-NH-$;
Y is taken together with $R_8$ to form oxo;
$R_{10}$ is an optionally substituted five-membered heteroaryl group;
$R_{11b}$ is $C_{1-6}$alkyl; and
n is 2.

In another embodiment of the present invention, there is provided pharmaceutical compositions useful in treating endocrine disorders, rheumatic disorders, collagen diseases, dermatologic disease, allergic disease, ophthalmic disease, respiratory disease, hematologic disease, gastrointestinal disease, inflammatory disease, autoimmune disease, diabetes, obesity, and neoplastic disease (especially inflammatory and autoimmune disease), as well as other uses as described herein, which includes a therapeutically effective amount (depending upon use) of a compound of formula (I) of the invention and a pharmaceutically acceptable carrier.

In still another embodiment, the present invention provides a method of treating endocrine disorders, rheumatic disorders, collagen diseases, dermatologic disease, allergic disease, ophthalmic disease, respiratory disease, hematologic disease, gastrointestinal disease, inflammatory disease, autoimmune disease, diabetes, obesity, and neoplastic disease (especially inflammatory and autoimmune disease), that is a disease associated with the expression product of a gene whose transcription is stimulated or repressed by glucocorticoid receptors, or a disease associated with AP-1- and/or NFκB (particularly AP-1-)-induced transcription, or a disease associated with AP-1 and/or NFκB— (particularly AP-1-) dependent gene expression, wherein the disease is associated with the expression of a gene under the regulatory control of AP-1 and/or NF-κB (particularly AP-1), including inflammatory and immune diseases and disorders as described hereinafter, which includes the step of administering a therapeutically effective amount of a compound of formula (I) of the invention to a patient.

Another embodiment of the present invention involves a method for treating a disease or disorder associated with the expression product of a gene whose transcription is stimulated or repressed by glucocorticoid receptors, or a method of treating a disease or disorder associated with AP-1- and/or NF-κB— (particularly AP-1-) induced transcription, or a method for treating a disease or disorder associated with AP-1 and/or NF-κB (particularly AP-1) dependent gene expression, wherein the disease is associated with the expression of a gene under the regulatory control of AP-1 and/or NF-κβ (particularly AP-1), such as inflammatory and immune disorders, cancer and tumor disorders, such as solid tumors, lymphomas and leukemia, and fungal infections such as mycosis fungoides (especially inflammatory and immune disorders).

The term "disease associated with GR transactivation," as used herein, refers to a disease associated with the transcription product of a gene whose transcription is transactivated by a GR. Such diseases include, but are not limited to: osteoporosis, diabetes, glaucoma, muscle loss, facial swelling, personality changes, hypertension, obesity, depression, and AIDS, the condition of wound healing, primary or secondary andrenocortical insufficiency, and Addison's disease.

The term "treat", "treating", or "treatment," in all grammatical forms, as used herein refers to the prevention, reduction, or amelioration, partial or complete alleviation, or cure of a disease, disorder, or condition, wherein prevention indicates treatment of a person at risk for developing such a disease, disorder or condition.

The terms "glucocorticoid receptor" and "GR," as used herein, refer either to a member of the nuclear hormone receptor ("NHR") family of transcription factors which bind glucocorticoids and either stimulate or repress transcription, or to GR-beta. These terms, as used herein, refer to glucocorticoid receptor from any source, including but not limited to: human glucocorticoid receptor as disclosed in Weinberger, et al. *Science* 228, p 640-742 (1985), and in Weinberger, et al. *Nature*, 318, p 670-672 (1986); rat glucocorticoid receptor as disclosed in Miesfeld, R. *Nature*, 312, p 779-781 (1985); mouse glucocortoid receptor as disclosed in Danielson, M. et al. *EMBO J.*, 5, 2513; sheep glucocorticoid receptor as disclosed in Yang, K., et al. *J. Mol. Endocrinol.* 8, p 173-180 (1992); marmoset glucocortoid receptor as disclosed in Brandon, D. D., et al, *J. Mol. Endocrinol.* 7, p 89-96 (1991); and human GR-beta as disclosed in Hollenberg, S M. et al. *Nature*, 318, p 635, 1985, Bamberger, C. M. et al. *J. Clin Invest.* 95, p 2435 (1995).

The term, "disease or disorder associated with AP-1 and/or NF-κB" as used herein, refers to a disease associated with the expression product of a gene under the regulatory control of AP-1 and/or NF-κB. Such diseases include, but are not limited to: inflammatory and immune diseases and disorders; cancer and tumor disorders, such as solid tumors, lymphomas and leukemia; and fungal infections such as mycosis fungoides.

The term "inflammatory or immune associated diseases or disorders" is used herein to encompass any condition, disease, or disorder that has an inflammatory or immune component, including, but not limited to, each of the following conditions: transplant rejection (e.g., kidney, liver, heart, lung, pancreas (e.g., islet cells), bone marrow, cornea, small bowel, skin allografts, skin homografts (such as employed in burn treatment), heart valve xenografts, serum sickness, and graft vs. host disease, autoimmune diseases, such as rheumatoid arthritis, psoriatic arthritis, multiple sclerosis, Type I and Type II diabetes, juvenile diabetes, obesity, asthma, inflammatory bowel disease (such as Crohn's disease and ulcerative colitis), pyoderma gangrenum, lupus (systemic lupus erythematosis), myasthenia gravis, psoriasis, dermatitis, dermatomyositis; eczema, seborrhoea, pulmonary inflammation, eye uveitis, hepatitis, Grave's disease, Hashimoto's thyroiditis, autoimmune thyroiditis, Behcet's or Sjorgen's syndrome (dry eyes/mouth), pernicious or immunohaemolytic anaemia, atherosclerosis, Addison's disease (autoimmune disease of the adrenal glands), idiopathic adrenal insufficiency, autoimmune polyglandular disease (also known as autoimmune polyglandular syndrome), glomerulonephritis, scleroderma, morphea, lichen planus, viteligo (depigmentation of the skin), alopecia greata, autoimmune alopecia, autoimmune hypopituatarism, Guillain-Barre syndrome, and alveolitis; T-cell mediated hypersensitivity diseases, including contact hypersensitivity, delayed-type hypersensitivity, contact dermatitis (including that due to poison ivy), uticaria, skin allergies, respiratory allergies (hayfever, allergic rhinitis) and gluten-sensitive enteropathy (Celiac disease); inflammatory diseases such as osteoarthritis, acute pancreatitis, chronic pancreatitis, acute respiratory distress syndrome, Sezary's syndrome and vascular diseases which have an inflammatory and or a proliferatory component such as restenosis, stenosis and artherosclerosis. Inflammatory or immune associated diseases or disorders also includes, but is not limited to: endocrine disorders, rheumatic disorders, collagen diseases, dermatologic disease, allergic disease, ophthalmic disease, respiratory disease, hematologic disease, gastrointestinal disease, inflammatory disease, autoimmune disease, congenital adrenal hyperplasia, nonsuppurative thyroiditis, hypercalcemia associated with cancer, juvenile rheumatoid arthritis, Ankylosing spondylitis, acute and subacute bursitis, acute nonspecific tenosynovitis, acute gouty arthritis, post-traumatic osteoarthritis, synovitis of osteoarthritis, epicondylitis, acute rheumatic carditis, pemphigus, bullous dermatitis herpetiformis, severe erythema multiforme, exfoliative dermatitis, seborrheic dermatitis, seasonal or perennial allergic rhinitis, bronchial asthma, contact dermatitis, atopic dermatitis, drug hypersensitivity reactions, allergic conjunctivitis, keratitis, herpes zoster ophthalmicus, iritis and iridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) hemolytic anemia, leukemias and lymphomas in adults, acute leukemia of childhood, regional enteritis, autoimmune vasculitis, multiple sclerosis, chronic obstructive pulmonary disease, solid organ transplant rejection, sepsis. Preferred treatments include treatment of transplant rejection, rheumatoid arthritis, psoriatic arthritis, multiple sclerosis, Type 1 diabetes, asthma, inflammatory bowel disease, systemic lupus erythematosis, psoriasis and chronic pulmonary disease. In a particular embodiment, the disease or disorder may be selected from transplant rejection, rheumatoid arthritis, psoriatic arthritis multiple sclerosis, Type I diabetes, asthma, inflammatory bowel disease, systemic lupus erthematosis, psoriasis and chronic pulmony disease.

In addition, in accordance with the present invention a method of treating a disease associated with AP-1-induced and/or NF-κB-induced transcription (particularly AP-1-induced transcription) is provided wherein a compound of formula (I) of the invention is administered to a patient at risk of developing the disease in a therapeutically effective amount to induce NHR transrepression of the AP-1-induced and/or NF-κB-induced transcription (particularly AP-1-induced transcription), thereby treating the disease.

Other therapeutic agents, such as those described hereafter, may be employed with the compounds of the invention in the present methods. In the methods of the present invention, such other therapeutic agent(s) may be administered prior to, simultaneously with or following the administration of the compound(s) of the present invention.

An embodiment of the present invention is a pharmaceutical combination comprising compounds of Formula (I) and an immunosuppressant, an anticancer agent, an anti-viral agent, an anti-inflammatory agent, an anti-fungal agent, an anti-biotic, an anti-vascular hyperproliferation agent, an antidepressant agent, a lipid-lowering agent, a lipid modulating agent, an antidiabetic agent, an anti-obesity agent, an antihypertensive agent, a platelet aggregation inhibitor, and/or an antiosteoporosis agent, wherein the antidiabetic agent is 1, 2, 3 or more of a biguanide, a sulfonyl urea, a glucosidase inhibitor, a PPAR γ agonist, a PPAR α/γ dual agonist, an SGLT2 inhibitor, a DP4 inhibitor, an aP2 inhibitor, an insulin sensitizer, a glucagon-like peptide-1 (GLP-1), insulin and/or a meglitinide, wherein the anti-obesity agent is a beta 3 adrenergic agonist, a lipase inhibitor, a serotonin (and dopamine) reuptake inhibitor, a thyroid receptor agonist, an aP2 inhibitor and/or an anorectic agent, wherein the lipid lowering agent is an MTP inhibitor, an HMG CoA reductase inhibitor, a squalene synthetase inhibitor, a fibric acid derivative, an upregulator of LDL receptor activity, a lipoxygenase inhibitor, or an ACAT inhibitor, wherein the antihypertensive agent is an ACE inhibitor, angiotensin II receptor antagonist, NEP/ACE inhibitor, calcium channel blocker and/or β-adrenergic blocker.

The antidiabetic agent may be 1, 2, 3 or more of metformin, glyburide, glimepiride, glipyride, glipizide, chlorpropamide, gliclazide, acarbose, miglitol, pioglitazone, troglitazone, rosiglitazone, insulin, G1-262570, isaglitazone, JTT-501, NN-2344, L895645, YM-440, R-119702, AJ9677, repaglinde, nateglinide, KAD1129, AR-HO39242, GW-409544, KRP297, AC2993, LY315902, P32/98 and/or NVP-DPP-728A, and the anti-obesity agent may be orlistat, ATL-962, AJ9677, L750355, CP331648, sibutramine, topiramate, axokine, dexamphetamine, phentermine, phenylpropanolamine, and/or mazindol, and the lipid_lowering agent may be pravastatin, lovastatin, simvastatin, atorvastatin, cerivastatin, fluvastatin, itavastatin, visastatin, fenofibrate, gemfibrozil, clofibrate, avasimibe, TS-962, MD-700, cholestagel, niacin and/or LY295427, and the antihypertensive agent may be an ACE inhibitor which is captopril, fosinopril, enalapril, lisinopril, quinapril, benazepril, fentiapril, ramipril or moexipril; and an NEP/ACE inhibitor which may be omapatrilat, [S[(R*,R*)]-hexahydro-6-[(2-mercapto-1-oxo-3-phenylpropyl)amino]-2,2-dimethyl-7-oxo-1H-azepine-1-acetic acid (gemopatrilat) or CGS 30440; and an angiotensin II receptor antagonist which may be irbesartan, losartan or valsartan; amlodipine besylate, prazosin HCl, verapamil, nifedipine, nadolol, propranolol, carvedilol, or clonidine HCl, and the platelet aggregation inhibitor may be aspirin, clopidogrel, ticlopidine, dipyridamole or ifetroban; and the immunosuppressant may be a cyclosporin, mycophenolate, interferon-beta, deoxyspergolin, FK-506 or Ant.-IL-2; and the anti-cancer agent may be azathiprine, 5-fluorouracel, cyclophosphamide, cisplatin, methotrexate, thiotepa, or carboplatin; and the anti-viral agent may be abacavir, aciclovir, ganciclovir, zidanocin, or vidarabine; and the antiinflammatory drug may be ibuprofen, celecoxib, rofecoxib, aspirin, naproxen, ketoprofen, diclofenac sodium, indomethacin, piroxicam, prednisone, dexamethasone, hydrocortisone, or triamcinolone diacetate.

In a particular embodiment, the compounds of the present invention are useful for the treatment of the aforementioned exemplary disorders irrespective of their etiology, for example, for the treatment of transplant rejection, rheumatoid arthritis, inflammatory bowel disease, and viral infections.

Methods of Synthesis

The compounds of the present invention may be synthesized by many methods available to those skilled in the art of organic chemistry. General synthetic schemes, in accordance with the present invention, for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds. Examples of compounds of the present invention prepared by methods described in the general schemes are given in the preparations and examples section set out hereinafter.

Scheme 1 outlines a general synthesis for a series of 4,5-dihydroindazoles. Many of the starting β-keto esters 1 are commercially available. Others are prepared following well known literature procedures, such as reaction of acid chlorides ($R_{11b}$—COCl) with potassium methyl malonate (Clay et al. *Synthesis* 1993, 290).

The alkylation of 1 may be effected with mild bases such as potassium carbonate. A wide variety of alkylating reagents ($R_{11a}$-LG) may be used for this reaction. The leaving group (LG) may be a halogen or sulfonate. After condensation of malonates 2 with (S)-alpha-methylbenzylamine, the stereoselective Michael reaction of enamine intermediates 3 with methyl vinyl ketone may be achieved under conditions reported by Nour et al. (Nour et al *Tetrahedron Asymmetry* 2001, 12, 765). After hydrolysis of the chiral amine auxiliary, diketones 4 can be obtained in enantiomerically enriched form. The antipodes of 4 may be synthesized from 2 using the other α-methylbenzylamine enantiomer. Alternative syntheses of diketones 4 include enantioselective Michael reaction to methyl vinyl ketone with a palladium catalyst (Hamashima et al. *J. Am. Chem. Soc.* 2002, 124, 11240), La-Na-BINOL complex (Sasai et al *Tetrahedron Lett.* 1996, 37, 5561), and copper catalyst (Christoffers et al *Chem. Eur. J.* 2001, 7, 1014). Diketones 4 can also be synthesized in racemic form from 2 and methyl vinyl ketone in the presence of catalytic amount of bases, such as sodium hydride (Begue et al *Synth. Commun.* 1992, 22, 573), or Lewis acids, such as ytterbium (III) trifluoromethanesulfonate (Keller et al *Tetrahedron Lett.* 1996, 37, 1879). The resolution of 4 or subsequent intermediates may be achieved using a variety of chiral HPLC columns.

Intramolecular aldol condensation of 4, in the presence of piperidine and acetic acid gives Hagemann's esters 5, which, in turn, can be converted to keto aldehydes 6 with ethyl formate, sodium in ethanol and ether. Treatment of 6 with hydrazines ($R_1$—$NHNH_2$), sodium acetate and acetic acid would yield 4,5-dihydroindazole intermediates 7, which may then be reduced to aldehydes 8 with diisobutylaluminum hydride. Reaction of 8 with organo lithium or magnesium reagents ($R_{10}$—X-M) would give the corresponding alcohols 10 (n=0). Alternatively, 8 may be elongated to aldehydes 9 via reaction with (methoxymethylene)triphenylphosphorane followed by acid hydrolysis. Aldehydes 9 can react with $R_{10}$—X-M to provide 10 (n=1). Alcohols 10 may then be oxidzed to ketones 11 under oxidation conditions, such as tetrapropylammonium perruthenate (TPAP) or Dess-Martin periodinane. Tertiary alcohols 12 may be obtained from 11 using organolithium or magnesium reagents ($R_8$-M). Analogues of 12 where $R_8$ is trifluoromethyl group may be prepared with (trifluoromethyl)trimethylsilane and tetrabutylammonium fluoride. Alcohols 10 can also be converted to variety of ethers (12a) with alkylating reagents ($R_{12}$-LG) under basic conditions such as sodium hydride in N,N-dimethyl formamide.

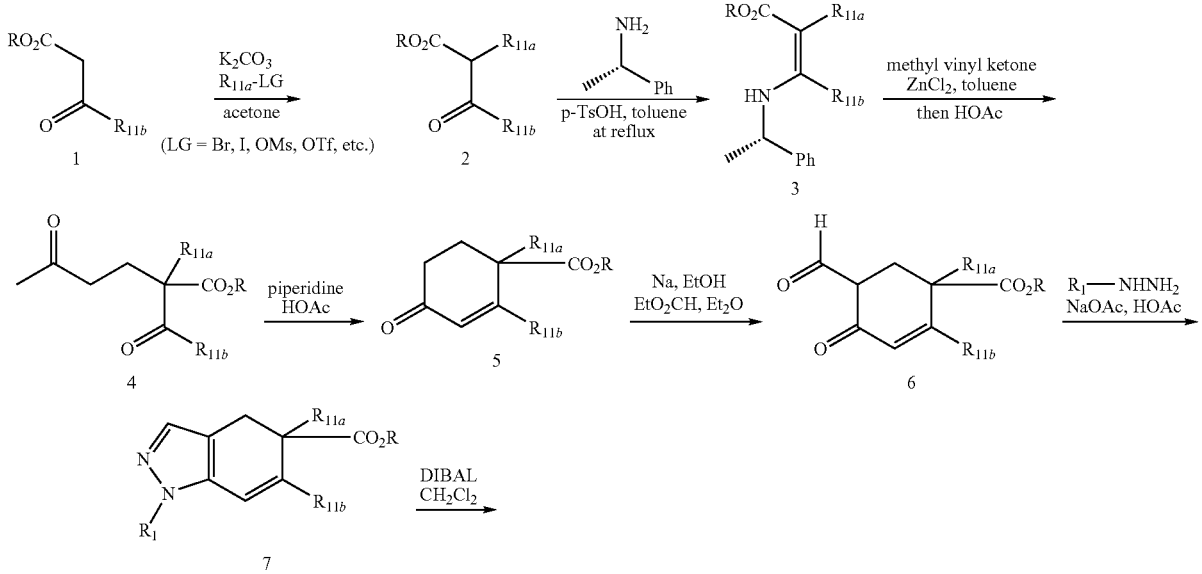

Scheme 1

-continued

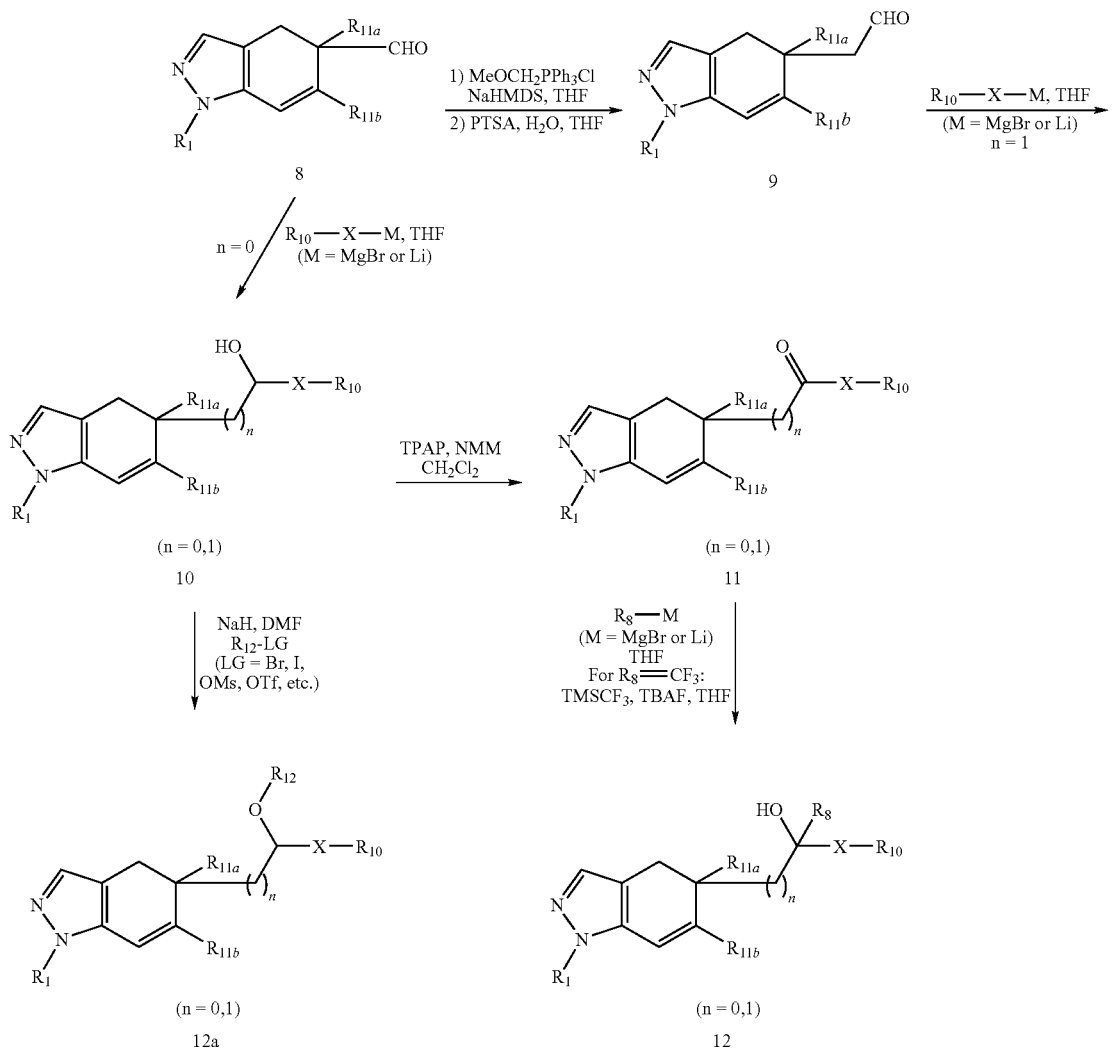

Scheme 2 outlines a general synthesis for a series of 4,5,6,7-tetrahydroindazoles. Treatment of ethyl 4-oxocyclohexanecarboxylate (13) with sodium ethoxide and ethyl formate would provide keto aldehydes 14, which can be converted to 4,5,6,7-tetrahydroindazoles 15 with hydrazines ($R_1$—$NHNH_2$), sodium acetate and acetic acid. Incorporation of $R_{11a}$ can be achieved by alkylation with LDA and $R_{11a}$-LG. Addition of hexamethylphosphoramide (HMPA) may improve the efficiency of reaction. Subsequent transformations are analogous to those described above for the 4,5-dihydroindazole series. Various secondary alcohols (19), ketones (20), tertiary alcohols (21) and ethers (19a) of the 4,5,6,7-tetrahydroindazoles can be synthesized using this route.

Scheme 2

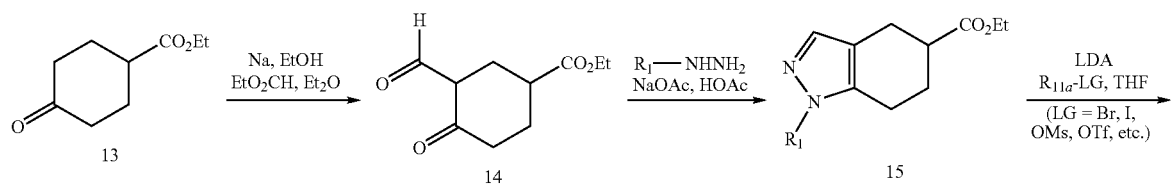

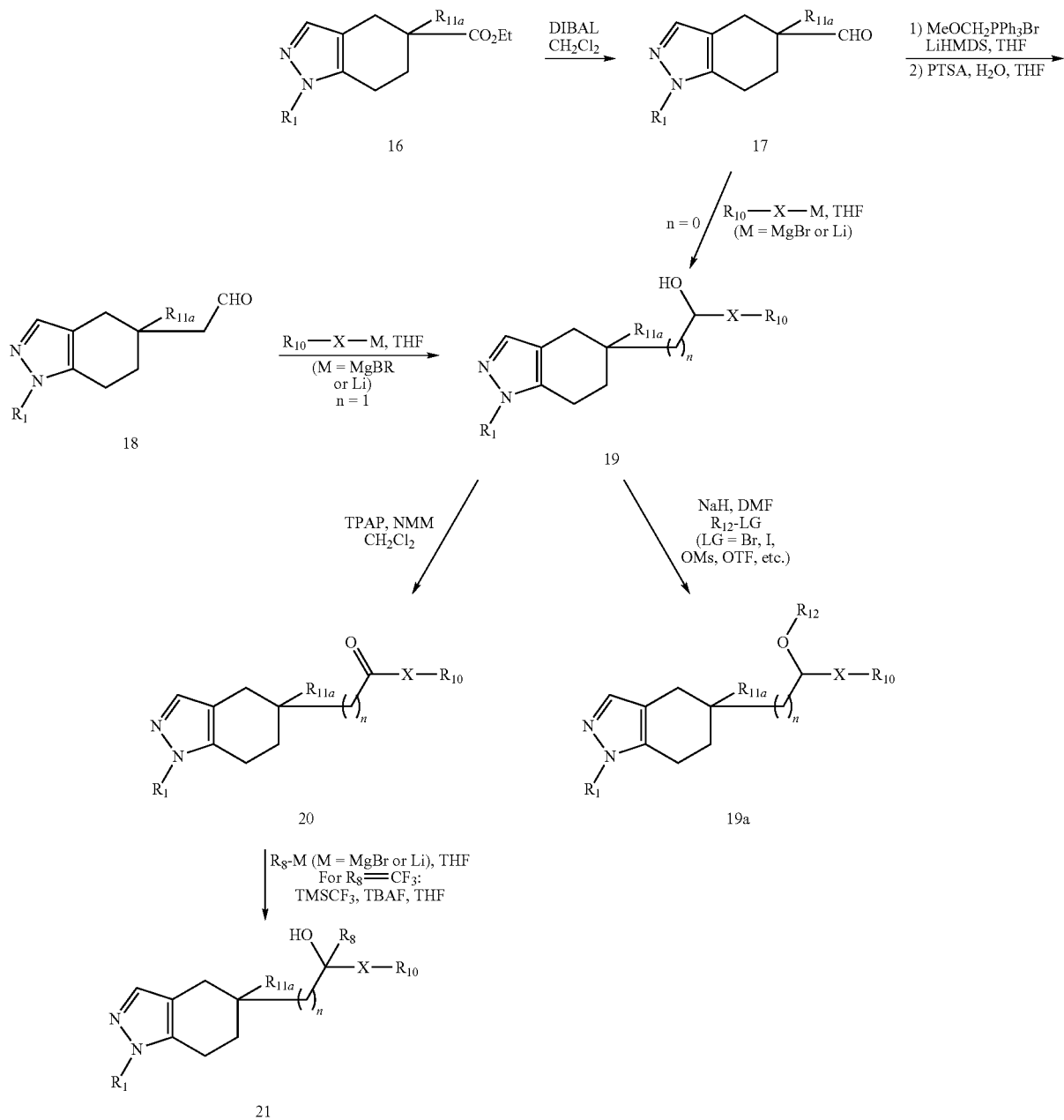

Aldehydes 8 and 9 from Scheme 1 can be useful intermediates for diversification. They can be reacted under Horner-Emmons or Wittig conditions to yield olefins 22 (Scheme 3). They can be reacted with amines ($R_{10}$—$NH_2$) under reductive conditions such as sodium triacetoxyborohydride to give secondary amines 23, which can be further derivatized to tertiary amines 24 under similar conditions. Alternatively, they can be converted to primary amines 25 by reaction with O-benzylhydroxylamine ($NH_2OBn$) to form oximes and reduction using conditions such as zinc in formic acid at elevated temperature. These primary amines can be converted to amides, carbamates and ureas (26) by reaction with acid chlorides, chloroformates, carbamoyl chlorides and isocyanates. Aldehydes 8 and 9 can also be converted to acetals 27 using trimethylsilyl trifluoromethanesulfonate (TMSOTf) conditions reported by Tsunoda et al (*Tetrahedron Lett.* 1980, 21, 1357). Furthermore, aldehydes 8 and 9 can be reduced with sodium borohydride, diisobutylaluminum hydride or lithium aluminum hydride to give alcohols 28, another useful intermediate for diversification. For example, 28 can react with acid chlorides, chloroformates, carbamoyl chloride and isocyanates to yield esters, carbonates and carbamates (29). 28 can also react with disulfide ($R_{10}SSR_{10}$) under Mitsunobu conditions to give sulfides 30, which can be oxidized to sulfoxides and sulfones 31 using oxone or metachloroperbenzoic acid.

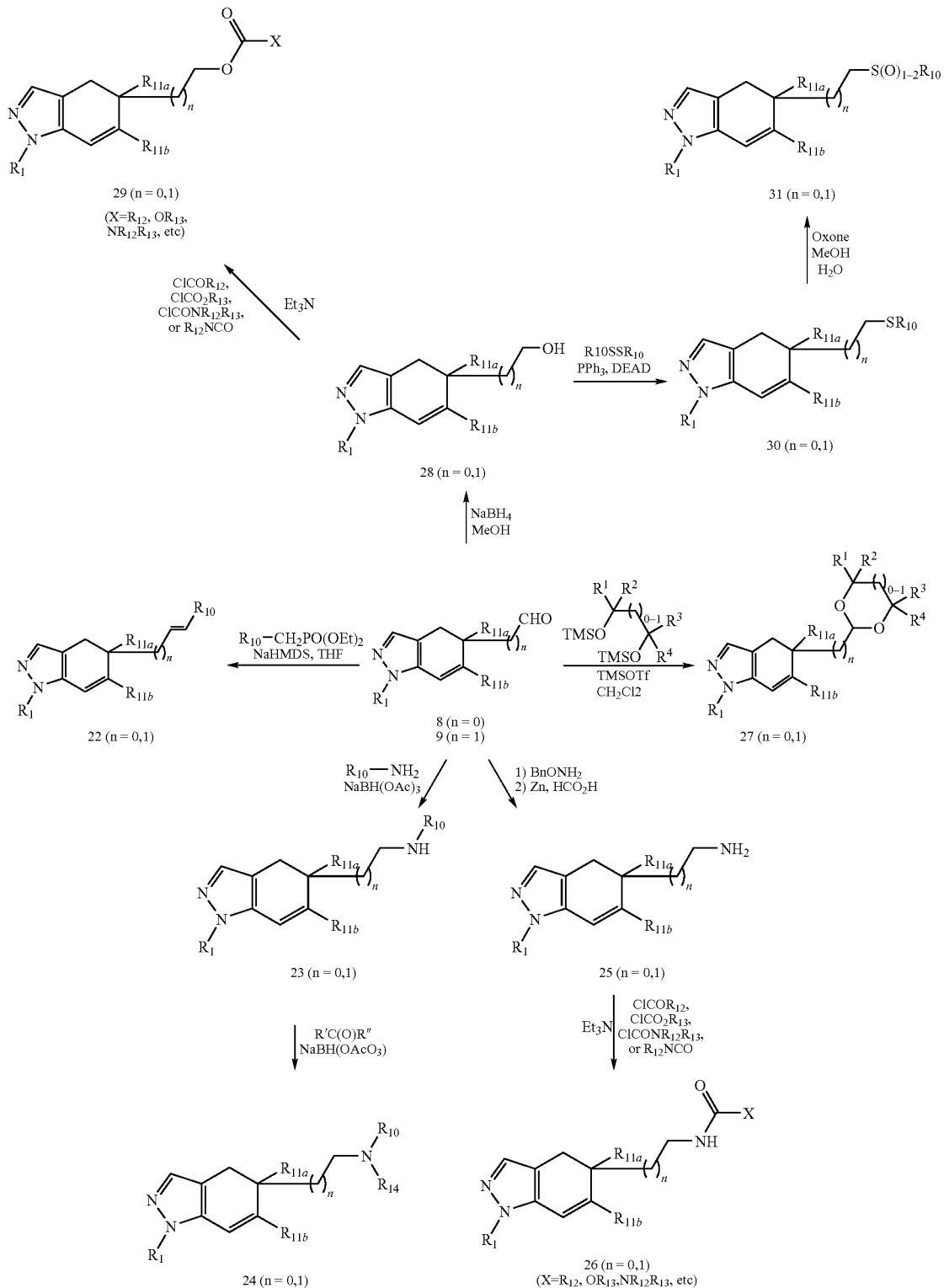

A series of amide derivatives 35 can be prepared following a sequence outlined in Scheme 4. Esters 7 can be converted to acids 32 using saponification conditions such as sodium hydroxide in methanol and water (for methyl or ethyl esters) or acidic conditions such as hydrogen chloride or trifluoroacetic acid (for t-butyl esters). Oxidation of aldehydes 9 under Sharpless sodium chlorite conditions will give acids 33. For preparation of acids 34, aldehydes 8 can be treated with stabilized Wittig ylide (Ph$_3$PCHCO$_2$Me). The resulting enoates could be selectively reduced with magnesium in methanol (Hudlicky et al. *Tetrahedron Lett.* 1987, 28, 5287). Subsequent hydrolysis with lithium hydroxide can provide the desired acids 34. Acids 32-34 can be coupled with variety of amines under standard coupling conditions, such as EDC, DCC, or BOP conditions, to give amides 35.

enyl, substituted alkenyl, alkynyl, nitro, cyano, oxo (=O), $OR_a$, $SR_a$, (=S), $-NR_aR_b$, $-N(alkyl)_3^+$, $-NR_aSO_2$, $-NR_aSO_2R_c$, $-SO_2R_c$ $-SO_2NR_aR_b$, $-SO_2NR_aC(=O)$ $R_b$, $SO_3H$, $-PO(OH)_2$, $-C(=O)R_a$, $-CO_2R_a$, $-C(=O)$ $NR_aR_b$, $-C(=O)(C_{1-4}alkylene)NR_aR_b$, $-C(=O)NR_a$

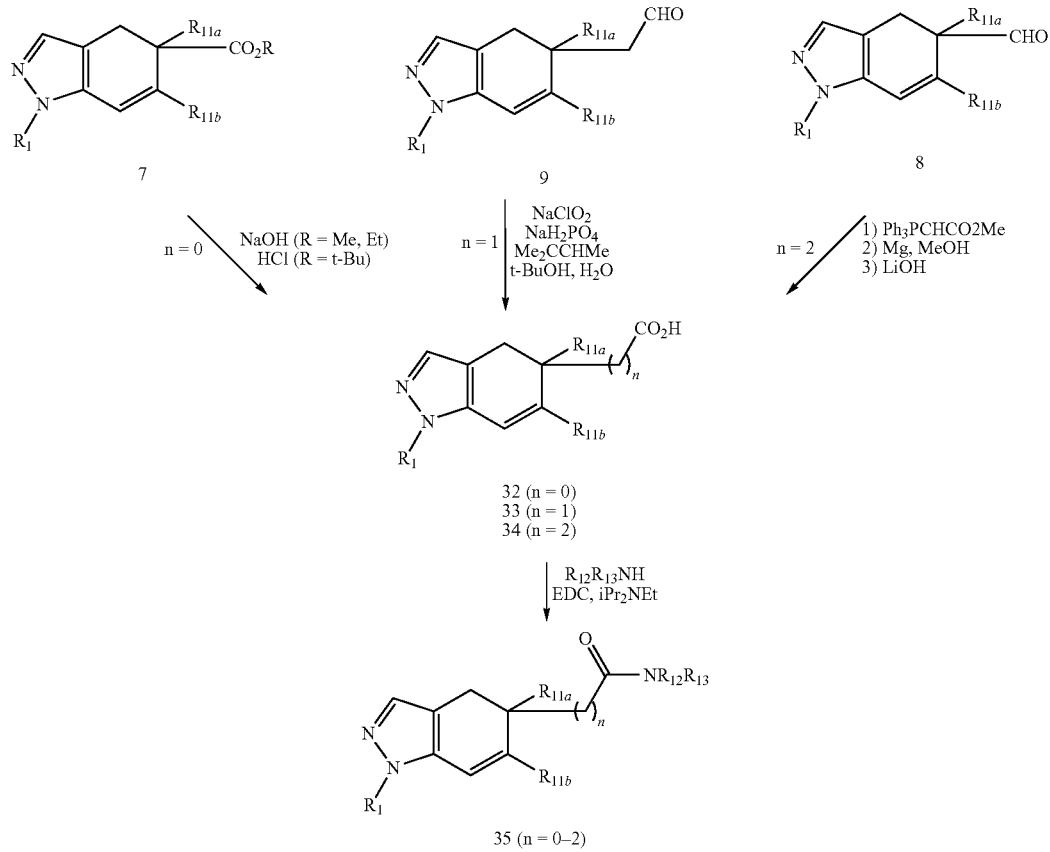

Definition of Terms

The following are definitions of terms used in this specification and appended claims. The initial definition provided for a group or term herein applies to that group or term throughout the specification and claims, individually or as part of another group, unless otherwise indicated.

The term "alkyl" refers to straight or branched chain hydrocarbon groups having 1 to 12 carbon atoms, preferably 1 to 6 carbon atoms. Lower alkyl groups, that is, alkyl groups of 1 to 4 carbon atoms, are most preferred. When numbers appear in a subscript after the symbol "C", the subscript defines with more specificity the number of carbon atoms that a particular group may contain. For example, "$C_{1-6}$alkyl" refers to straight and branched chain alkyl groups with one to six carbon atoms, such as methyl, ethyl, n-propyl, isopropyl, n-butyl, t-butyl, n-pentyl, and so forth. The subscript "0" refers to a bond. Thus, the term hydroxy($C_{0-2}$)alkyl or ($C_{0-2}$) hydroxyalkyl includes hydroxy, hydroxymethyl and hydroxyethyl.

The term "substituted alkyl" refers to an alkyl group as defined above having one, two, or three substituents selected from the group consisting of halo (e.g., trifluoromethyl), alk- $(SO_2)R_b$, $-CO_2(C_{1-4}alkylene)NR_aR_b$, $-NR_aC(=O)R_b$, $-NR_aCO_2R_b$, $-NR_a(C_{1-4}alkylene)CO_2R_b$, =N-OH, =N-O-alkyl, aryl, cycloalkyl, heterocyclo, and/or heteroaryl, wherein $R_a$ and $R_b$ are selected from hydrogen, alkyl, alkenyl, $CO_2H$, $CO_2(alkyl)$, $C_{3-7}$cycloalkyl, phenyl, benzyl, phenylethyl, napthyl, a four to seven membered heterocyclo, or a five to six membered heteroaryl, or when attached to the same nitrogen atom may join to form a heterocyclo or heteroaryl, and $R_c$ is selected from same groups as $R_a$ and $R_b$ but is not hydrogen. Each group $R_a$ and $R_b$ when other than hydrogen, and each $R_c$ group optionally has up to three further substituents attached at any available carbon or nitrogen atom of $R_a$, $R_b$, and/or $R_c$, said substituent(s) being selected from the group consisting of ($C_{1-6}$)alkyl, ($C_{2-6}$)alkenyl, hydroxy, halogen, cyano, nitro, $CF_3$, $O(C_{1-6}alkyl)$, $OCF_3$, $C(=O)H$, $C(=O)(C_{1-6}alkyl)$, $CO_2H$, $CO_2(C_{1-6}alkyl)$, $NHCO_2(C_{1-6}$ alkyl), $-S(C_{1-6}alkyl)$, $-NH_2$, $NH(C_{1-6}alkyl)$, $N(C_{1-6}$ alkyl)$_2$, $N(CH_3)_3^+$, $SO_2(C_{1-6}alkyl)$, $C(=O)(C_{1-4}alkylene)$ $NH_2$, $C(=O)(C_{1-4}alkylene)NH(alkyl)$, $C(=O)(C_{1-4}alkylene)N(C_{1-4}alkyl)_2$, $C_{3-7}$cycloalkyl, phenyl, benzyl, phenylethyl, phenyloxy, benzyloxy, napthyl, a four to seven membered heterocyclo, or a five to six membered heteroaryl. When a substituted alkyl is substituted with an aryl, heterocyclo, cycloalkyl, or heteroaryl group, said ringed systems are as defined below and thus may have zero, one, two, or three substituents, also as defined below.

One skilled in the field will understand that, when the designation "CO$_2$" is used herein, this is intended to refer to the group

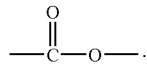

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl $(C_{0-4})$alkyl includes a substituted lower alkyl having at least one aryl substituent and also includes an aryl directly bonded to another group, i.e., aryl($C_0$)alkyl.

The term "alkenyl" refers to straight or branched chain hydrocarbon groups having 2 to 12 carbon atoms and at least one double bond. Alkenyl groups of 2 to 6 carbon atoms and having one double bond are most preferred.

The term "alkynyl" refers to straight or branched chain hydrocarbon groups having 2 to 12 carbon atoms and at least one triple bond. Alkynyl groups of 2 to 6 carbon atoms and having one triple bond are most preferred.

The term "alkylene" refers to bivalent straight or branched chain hydrocarbon groups having 1 to 12 carbon atoms, preferably 1 to 6 carbon atoms, e.g., $\{-CH_2-\}_n$, wherein n is 1 to 12, preferably 1-6. Lower alkylene groups, that is, alkylene groups of 1 to 4 carbon atoms, are most preferred. The terms "alkenylene" and "alkynylene" refer to bivalent radicals of alkenyl and alkynyl groups, respectively, as defined above.

When reference is made to a substituted alkenyl, alkynyl, alkylene, alkenylene, or alkynylene group, these groups are substituted with one to three substitutents as defined above for substituted alkyl groups.

The term "heteroalkylene" is used herein to refer to saturated and unsaturated bivalent straight or branched chain hydrocarbon groups having 2 to 12 carbon atoms, preferably 2 to 8 carbon atoms, wherein one or two carbon atoms in the straight chain are replaced by heteroatom(s) selected from —O—, —S—, —S(=O)—, —SO$_2$—, —NH—, and —NHSO$_2$—. Thus, the term "heteroalkylene" includes bivalent alkoxy, thioalkyl, and aminoalkyl groups, as defined below, as well as alkylene and alkenylene groups having a combination of heteroatoms in the alkyl chain. As an illustration, a "heteroalkylene" herein may comprise groups such as —S—(CH$_2$)$_{1-5}$NH—CH$_2$—, —O—(CH$_2$)$_{1-5}$S(=O)—CH$_2$—, —NHSO$_2$—CH$_2$—, —CH$_2$—NH—, and so forth. Preferably, a heteroalkylene does not have two adjacent atoms simultaneously selected from —O— and —S—. When a subscript is used with the term heteroalkylene, e.g., as in |C$_{2-3}$heteroalkylene, the subscript refers to the number of carbon atoms in the group in addition to heteroatoms. Thus, for example, a C$_{1-2}$ heteroalkylene may include groups such as —NH—CH$_2$—, —CH$_2$—NH—CH$_2$—, —CH$_2$—CH$_2$—NH—, —S—CH$_2$—, —CH$_2$—S—CH$_2$—, —O—CH$_2$—NH—CH$_2$—, CH$_2$—O—CH$_2$ and so forth.

The term "substituted heteroalkylene" refers to a heteroalkylene group as defined above wherein at least one of the nitrogen or carbon atoms in the heteroalkylene chain is bonded to (or substituted with) a group other than hydrogen. Carbon atoms in the heteroalkylene chain may be substituted with a group selected from those recited above for substituted alkyl groups, or with a further alkyl or substituted alkyl group. Nitrogen atoms of the heteroalkylene chain may be substituted with a group selected from alkyl, alkenyl, alkynyl, cyano, or A$_1$-Q-A$_2$-R$_h$, wherein A$_1$ is a bond, C$_{1-2}$alkylene, or C$_{2-3}$alkenylene; Q is a bond, —C(=O)—, —C(=O)NR$_d$—, —C(=S)NR$_d$—, —SO$_2$—, —SO$_2$NR$_d$—, —CO$_2$—, or —NR$_d$CO$_2$—; A$_2$ is a bond, C$_{1-3}$alkylene, C$_{2-3}$alkenylene, —C$_{1-4}$alkylene-NR$_d$—, —C$_{1-4}$alkylene-NR$_d$C(=O)—, —C$_{1-4}$alkylene-S—, —C$_{1-4}$alkylene-SO$_2$—, or —C$_{1-4}$alkylene-O—, wherein said A$_2$ alkylene groups are branched or straight chain and optionally substituted as defined herein for substituted alkylene; R$_h$ is hydrogen, alkyl, substituted alkyl, alkenyl, substituted alkenyl, aryl, heteroaryl, heterocyclo, or cycloalkyl; and R$_d$ is selected from hydrogen, alkyl, and substituted alkyl, as defined herein, provided, however, that for a substituted heteralkylene R$_h$ is not hydrogen when A$_1$, Q and A$_2$ are each bonds. When R$_h$ is aryl, heteroaryl, cycloalkyl, or heterocyclo, these rings are, in turn, optionally substituted with one to three groups as defined below in the definitions for these terms.

The term "alkoxy" refers to an alkyl or substituted alkyl group as defined above having one or two oxygen atoms (—O—) in the alkyl chain. For example, the term "alkoxy" includes the groups —O—C$_{1-2}$alkyl, —C$_{1-6}$alkylene)-O—C$_{1-6}$alkyl, —C$_{1-4}$alkylene-O—C$_{1-4}$alkylene)-O—C$_{1-4}$alkyl, and so forth.

The term "thioalkyl" or "alkylthio" refers to an alkyl or substituted alkyl group as defined having one or two sulfur atoms in the alkyl chain. For example, the term "thioalkyl" or "alkylthio" includes the groups —S—C$_{1-12}$alkyl, —(S—C$_{1-6}$alkylene)-S—C$_{1-6}$alkyl, and so forth.

The terms "aminoalkyl" or "alkylamino" refer to an alkyl or substituted alkyl group as defined above having one or two nitrogen (—NR—) atoms in the alkyl chain. For example, the term "aminoalkyl" includes the groups —NR—C$_{1-12}$alkyl, —NR—C$_{1-6}$alkylene-NR—C$_{1-6}$alkyl, etc. (where R is preferably hydrogen but may include alkyl or substituted alkyl as defined above.) When a subscript is used with reference to an alkoxy, thioalkyl or aminoalkyl, the subscript refers to the number of carbon atoms that the group may contain in addition to heteroatoms. Thus, for example, monovalent C$_{1-2}$aminoalkyl includes the groups —CH$_2$—NH$_2$, —NH—CH$_3$, —(CH$_2$)$_2$—NH$_2$, —NH—CH$_2$—CH$_3$, —CH$_2$—NH$_2$—CH$_3$, and —N—(CH$_3$)$_2$. A lower aminoalkyl comprises an aminoalkyl having one to four carbon atoms. "Amino" refers to the group NH$_2$. The alkoxy, thioalkyl, or aminoalkyl groups may be monovalent or bivalent. By "monovalent" it is meant that the group has a valency (i.e., ability to combine with another group), of one, and by "bivalent" it is meant that the group has a valency of two. Thus, for example, a monovalent alkoxy includes groups such as —O—C$_{1-12}$alkyl, —C$_{1-6}$alkylene-O—C$_{1-6}$alkyl, —C$_4$alkylene-O—C$_{1-4}$alkylene-O—C$_{1-4}$alkyl, whereas a bivalent alkoxy includes groups such as —O—C$_{1-12}$alkylene-, —C$_{1-6}$alkylene-O—C$_{1-6}$alkylene-, —C$_{1-4}$alkylene-O—C$_{1-4}$alkylene-O—C$_{1-4}$alkylene-, and so forth. Where a bivalent group is specified, attachment may occur at either end of the bivalent group. For example bivalent groups such as —Oalkylene-, —N(R$_{14}$)—C(O)—, —N(R$_{14}$)—C(O)O—, and —NR$_{15}$C(O)NR$_{16}$—, are also intended to include -alkyleneO—, —C(O)—N(R$_{14}$)—, —OC(O)N(R$_{14}$)—, and —NR$_{16}$C(O)NR$_{15}$—. Accordingly a compound having an asymmetric bivalent group indicates two compounds having differing attachment.

It should be understood that the selections for alkoxy, thioalkyl, and aminoalkyl will be made by one skilled in the field to provide stable compounds. Thus, for example, in compounds of formula (I), when G is attached to a nitrogen atom (N*) of ring A and is selected from an alkoxy or alkylthio group, the alkoxy and alkylthio groups will have at least one carbon atom bonded directly to ring A (at N*), with the oxygen or sulfur atoms being at least one atom away from said nitrogen atom.

The term "acyl" refers to a carbonyl group linked to an organic radical, more particularly, the group C(=O)$R_e$, as well as the bivalent groups —C(=O)— or —C(=O)$R_e$—, which are linked to organic radicals or ring A in compounds of formula (I). The group $R_e$ can be selected from alkyl, alkenyl, alkynyl, aminoalkyl, substituted alkyl, substituted alkenyl, or substituted alkynyl, as defined herein, or when appropriate, the corresponding bivalent group, e.g., alkylene, alkenylene, etc. Accordingly, in compounds of formula (I), the groups —C(=O)$R_e$— or —$R_e$C(=O)—, wherein in this instance, the group $R_e$ will be selected from bivalent groups, e.g., alkylene, alkenylene, alkynylene, bivalent aminoalkyl, substituted alkylene, substituted alkenylene, or substituted alkynylene.

The term "alkoxycarbonyl" refers to a carboxy group

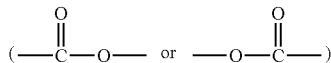

linked to an organic radical (CO$_2$$R_e$), as well as the bivalent groups —CO$_2$—, —CO$_2$$R_e$— which are linked to organic radicals in compounds of formula (I), wherein $R_e$ is as defined above for acyl. The organic radical to which the carboxy group is attached may be monovalent (e.g., —CO$_2$-alkyl or —OC(=O)alkyl), or bivalent (e.g., —CO$_2$-alkylene, —OC(=O)alkylene, etc.) Accordingly, in compounds of formula (I), when it is recited that G can be "alkoxycarbonyl," this is intended to encompass a selection for G of —CO$_2$— and also the groups —CO$_2$$R_e$— or —$R_e$CO$_2$—, wherein in this instance, the group $R_e$ will be selected from bivalent groups, e.g., alkylene, alkenylene, alkynylene, bivalent aminoalkyl, substituted alkylene, substituted alkenylene, or substituted alkynylene.

The term "amide" or "amidyl" refers to the group C(=O)N$R_a$$R_b$, wherein the groups $R_a$ and $R_b$ are defined as recited above in the definition for substituted alkyl groups.

The term "sulfonyl" refers to a sulphoxide group linked to an organic radical in compounds of formula (I), more particularly, the monovalent group S(O)$_{1-2}$—$R_e$, or the bivalent group —S(O)$_{1-2}$— linked to organic radicals in compounds of formula (I). Accordingly, in compounds of formula (I), when it is recited that G can be "sulfonyl," this is intended to encompass a selection for G of —S(=O)— or —SO$_2$— as well as the groups —S(=O)$R_e$—, —$R_e$S(=O)—, —SO$_2$$R_e$—, or —$R_e$SO$_2$—, wherein in this instance, the group $R_e$ will be selected from those recited above for acyl and alkoxycarbonyl groups.

The term "sulfonamidyl" refers to the group —S(O)$_2$N$R_a$$R_b$, wherein $R_a$ and $R_b$ are as defined above for substituted alkyl groups. Additionally, the sulfonamidyl group may be bivalent, in which case one of the groups $R_a$ and $R_b$ will be a bond. Thus, in compounds of formula (I), when it is stated that G may be sulfonamidyl, it is intended to mean that G is a group —S(O)$_2$N$R_a$—.

The term "cycloalkyl" refers to fully saturated and partially unsaturated hydrocarbon rings of 3 to 9, preferably 3 to 7 carbon atoms. The term "cycloalkyl" includes such rings having zero, one, two, or three substituents selected from the group consisting of halogen, trifluoromethyl, trifluoromethoxy, alkyl, substituted alkyl, alkenyl, substituted alkenyl, alkynyl, nitro, cyano, oxo (=O), OR$_a$, SR$_a$, (=S), —NR$_a$R$_b$, —N(alkyl)$_3$+, —NR$_a$SO$_2$, —NR$_a$SO$_2$R$_c$, —SO$_2$R$_e$ —SO$_2$NR$_a$R$_b$, —SO$_2$NR$_a$C(=O)R$_b$, SO$_3$H, —PO(OH)$_2$, —C(=O)R$_a$, —CO$_2$R$_a$, —C(=O)NR$_a$R$_b$, —C(=O)(C$_{1-4}$alkylene)NR$_a$R$_b$, —C(=O)NR$_a$(SO$_2$)R$_b$, —CO$_2$(C$_{1-4}$alkylene)NR$_a$R$_b$, —NR$_a$C(=O)R$_b$, —NR$_a$CO$_2$R$_b$, —NR$_a$(C$_{1-4}$alkylene)CO$_2$R$_b$, =N—OH, =N—O-alkyl, aryl, cycloalkyl, heterocyclo, and/or heteroaryl, wherein R$_a$, R$_b$ and R$_e$ are as defined above for substituted alkyl groups, and are also in turn optionally substituted as recited above in the definition for substituted alkyl groups. The term "cycloalkyl" also includes such rings having a second ring fused thereto (e.g., including benzo, heterocyclo, or heteroaryl rings) or having a carbon-carbon bridge of 3 to 4 carbon atoms. When a cycloalkyl is substituted with a further ring (or has a second ring fused thereto), said ring in turn is optionally substituted with one to two of (C$_{1-4}$)alkyl, (C$_{2-4}$)alkenyl, halogen, hydroxy, cyano, nitro, CF$_3$, O(C$_{1-4}$alkyl), OCF$_3$, C(=O)H, C(=O)(C$_{1-4}$alkyl), CO$_2$H, CO$_2$(C$_{1-4}$alkyl), NHCO$_2$(C$_{1-4}$alkyl), —S(C$_{1-4}$alkyl), —NH$_2$, NH(C$_{1-4}$alkyl), N(C$_{1-4}$alkyl)$_2$, N(C$_{1-4}$alkyl)$_3$$^+$, SO$_2$(C$_{1-4}$alkyl), C(=O)(C$_{1-4}$alkylene)NH$_2$, C(=O)(C$_{1-4}$alkylene)NH(alkyl), and/or C(=O)(C$_{1-4}$ alkylene)N(C$_{1-4}$alkyl)$_2$.

Accordingly, in compounds of formula (I), the term "cycloalkyl" includes cyclopropyl, cyclobutyl, cyclopentyl, cyclopentenyl, cyclohexyl, cyclohexenyl, cycloheptyl, cyclooctyl, etc., as well as the following ring systems,

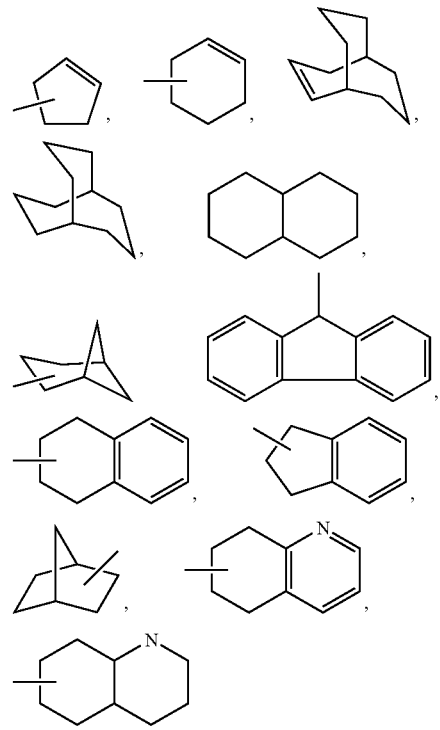

and the like, which optionally may be substituted at any available atoms of the ring(s). Preferred cycloalkyl groups include cyclopropyl, cyclobutyl, cyclopentyl, cyclohexyl,

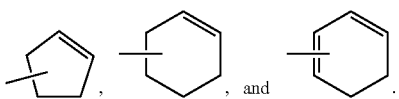

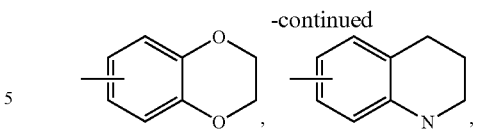

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes $OCF_3$.

The term "aryl" refers to phenyl, biphenyl, 1-naphthyl and 2-naphthyl. The term "aryl" includes such rings having zero, one, two or three substituents selected from the group consisting of halogen, trifluoromethyl, trifluoromethoxy, alkyl, substituted alkyl, alkenyl, substituted alkenyl, alkynyl, nitro, cyano, $OR_a$, $SR_a$, (=S), $-NR_aR_b$, $-N(alkyl)_3^+$, $-NR_aSO_2$, $-NR_aSO_2R_c$, $-SO_2R_c$, $-SO_2NR_aR_b$, $-SO_2NR_aC(=O)R_b$, $SO_3H$, $-PO(OH)_2$, $-C(=O)R_a$, $-CO_2R_a$, $-C(=O)NR_aR_b$, $-C(=O)(C_{1-4}alkylene)NR_aR_b$, $-C(=O)NR_a(SO_2)R_b$, $-CO_2(C_{1-4}alkylene)NR_aR_b$, $NR_aC(=O)R_b$, $-NR_aCO_2R_b$, $-NR_a(C_{1-4}alkylene)CO_2R_b$, aryl, cycloalkyl, heterocyclo, and/or heteroaryl, wherein $R_a$, $R_b$ and $R_c$ are as defined above for substituted alkyl groups, and are also in turn optionally substituted as recited above. Additionally, two substituents attached to an aryl, particularly a phenyl group, may join to form a further ring such as a fused or spiro-ring, e.g., cyclopentyl or cyclohexyl, or fused heterocyclo or heteroaryl. When an aryl is substituted with a further ring (or has a second ring fused thereto), said ring in turn is optionally substituted with one to two of $(C_{1-4})$alkyl, $(C_{2-4})$alkenyl, halogen, hydroxy, cyano, nitro, $CF_3$, $O(C_{1-4}alkyl)$, $OCF_3$, $C(=O)H$, $C(=O)(C_{1-4}alkyl)$, $CO_2H$, $CO_2(C_{1-4}alkyl)$, $NHCO_2(C_{1-4}alkyl)$, $-S(C_{1-4}alkyl)$, $-NH_2$, $NH(C_{1-4}alkyl)$, $N(C_{1-4}alkyl)_2$, $N(C_{1-4}alkyl)_3^+$, $SO_2(C_{1-4}alkyl)$, $C(=O)(C_{1-4}alkylene)NH_2$, $C(=O)(C_{1-4}alkylene)NH(alkyl)$, and/or $C(=O)(C_{1-4}alkylene)N(C_{1-4}alkyl)_2$.

Thus, examples of aryl groups include:

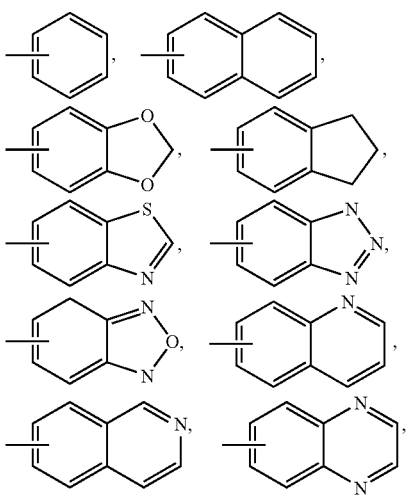

and the like, which optionally may be substituted at any available carbon or nitrogen atom. A preferred aryl group is optionally-substituted phenyl.

The terms "heterocyclo" or "heterocyclic" refers to substituted and unsubstituted non-aromatic 3 to 7 membered monocyclic groups, 7 to 11 membered bicyclic groups, and 10 to 15 membered tricyclic groups, in which at least one of the rings has at least one heteroatom (O, S or N). Each ring of the heterocyclo group containing a heteroatom can contain one or two oxygen or sulfur atoms and/or from one to four nitrogen atoms provided that the total number of heteroatoms in each ring is four or less, and further provided that the ring contains at least one carbon atom. The fused rings completing bicyclic and tricyclic groups may contain only carbon atoms and may be saturated, partially saturated, or unsaturated. The nitrogen and sulfur atoms may optionally be oxidized and the nitrogen atoms may optionally be quaternized. The heterocyclo group may be attached at any available nitrogen or carbon atom. The heterocyclo ring may contain zero, one, two or three substituents selected from the group consisting of halogen, trifluoromethyl, trifluoromethoxy, alkyl, substituted alkyl, alkenyl, substituted alkenyl, alkynyl, nitro, cyano, oxo (=O), $OR_a$, $SR_a$, (=S), $NR_aR_b$, $-N(alkyl)_3^+$, $-NR_aSO_2$, $NR_aSO_2R_c$, $-SO_2R_c$ $-SO_2NR_aR_b$, $-SO_2NR_aC(=O)R_b$, $SO_3H$, $-PO(OH)_2$, $-C(=O)R_a$, $CO_2R_a$, $-C(=O)NR_aR_b$, $-C(=O)(C_{1-4}alkylene)NR_aR_b$, $-C(=O)NR_a(SO_2)R_b$, $-CO_2(C_{1-4}alkylene)NR_aR_b$, $-NR_aC(=O)R_b$, $-NR_aCO_2R_b$, $-NR_a(C_{1-4}alkylene)CO_2R_b$, =N—OH, =N—O-alkyl, aryl, cycloalkyl, heterocyclo, and/or heteroaryl, wherein $R_a$, $R_b$ and $R_c$ are as defined above for substituted alkyl groups, and are also in turn optionally substituted as recited above. When a heterocyclo is substituted with a further ring, said ring in turn is optionally substituted with one to two of $(C_{1-4})$alkyl, $(C_{2-4})$alkenyl, halogen, hydroxy, cyano, nitro, $CF_3$, $O(C_{1-4}alkyl)$, $OCF_3$, $C(=O)H$, $C(=O)(C_{1-4}alkyl)$, $CO_2H$, $CO_2(C_{1-4}alkyl)$, $NHCO_2(C_{1-4}alkyl)$, $-S(C_{1-4}alkyl)$, $-NH_2$, $NH(C_{1-4}alkyl)$, $N(C_4alkyl)_2$, $N(C_{1-4}alkyl)_3^+$, $SO_2(C_{1-4}alkyl)$, $C(=O)(C_{1-4}alkylene)NH_2$, $C(=O)(C_{1-4}alkylene)NH(alkyl)$, and/or $C(=O)(C_{1-4}alkylene)N(C_{1-4}alkyl)_2$.

Exemplary monocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl.

Preferred heterocyclo groups in compounds of formula (I) include

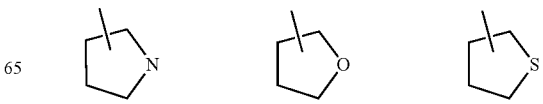

-continued

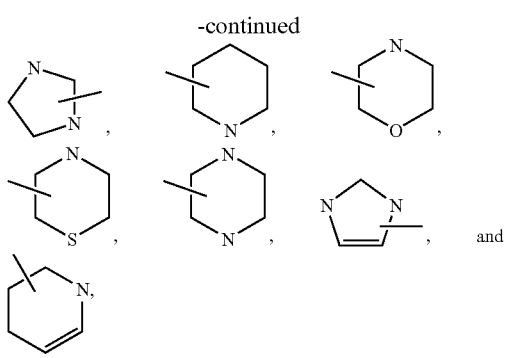

which optionally may be substituted.

The term "heteroaryl" refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents selected from the group consisting of halogen, trifluoromethyl, trifluoromethoxy, alkyl, substituted alkyl, alkenyl, substituted alkenyl, alkynyl, nitro, cyano, $OR_a$, $SR_a$, (=S), —$NR_aR_b$, —$N(alkyl)_3^+$, —$NR_aSO_2$, —$NR_aSO_2R_c$, —$SO_2R_c$, —$SO_2NR_aR_b$, —$SO_2NR_aC(=O)R_b$, $SO_3H$, —$PO(OH)_2$, $C(=O)R_a$, —$CO_2R_a$, —$C(=O)NR_aR_b$, —$C(=O)(C_{1-4}alkylene)NR_aR_b$, —$C(=O)NR_a(SO_2)R_b$, —$CO_2(C_{1-4}alkylene)NR_aR_b$, —$NR_aC(=O)R_b$, $NR_aCO_2R_b$, —$NR_a(C_{1-4}alkylene)CO_2R_b$, aryl, cycloalkyl, heterocyclo, and/or heteroaryl, wherein $R_a$, $R_b$ and $R_c$ are as defined above for substituted alkyl groups, and are also in turn optionally substituted as recited above. When a heteroaryl is substituted with a further ring, said ring in turn is optionally substituted with one to two of $(C_{1-4})$alkyl, $(C_{2-4})$alkenyl, halogen, hydroxy, cyano, nitro, $CF_3$, $O(C_{1-4}alkyl)$, $OCF_3$, $C(=O)H$, $C(=O)(C_{1-4}alkyl)$, $CO_2H$, $CO_2(C_{1-4}alkyl)$, $NHCO_2(C_{1-4}alkyl)$, —$S(C_{1-4}alkyl)$, —$NH_2$, $NH(C_{1-4}alkyl)$, $N(C_{1-4}alkyl)_2$, $N(C_{1-4}alkyl)_3^+$, $SO_2(C_{1-4}alkyl)$, $C(=O)(C_{1-4}alkylene)NH_2$, $C(=O)(C_{1-4}alkylene)NH(alkyl)$, and/or $C(=O)(C_{1-4}alkylene)N(C_{1-4}alkyl)_2$.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

In compounds of formula (I), preferred heteroaryl groups include

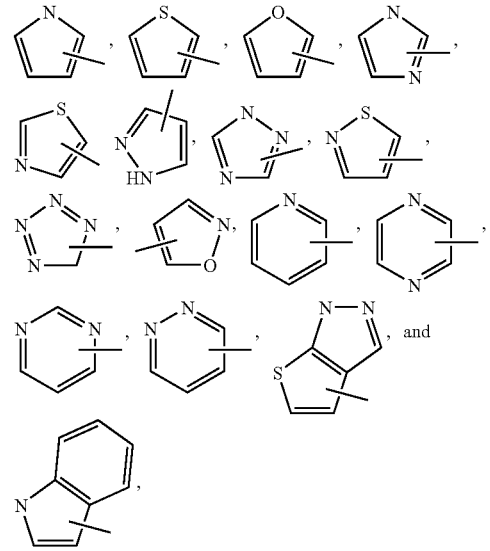

and the like, which optionally may be substituted at any available carbon or nitrogen atom.

CAS Registry Number refers to the unique identifier number assigned to chemical compounds by the Chemical Abstracts Service, a division of the American Chemical Society.

Unless otherwise indicated, when reference is made to a specifically-named aryl (e.g., phenyl), cycloalkyl (e.g., cyclohexyl), heterocyclo (e.g., pyrrolidinyl) or heteroaryl (e.g., imidazolyl), unless otherwise specifically indicated the reference is intended to include rings having 0 to 3, preferably 0-2, substituents selected from those recited above for the aryl, cycloalkyl, heterocyclo and/or heteroaryl groups, as appropriate.

The term "heteroatoms" shall include oxygen, sulfur and nitrogen.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

The term "optionally substituted" is intended to include both unsubstituted and substituted groups.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The term "prodrug" denotes a compound which, upon administration to a subject, undergoes chemical conversion by metabolic or chemical processes to yield a compound of the formula (I), and/or a salt and/or solvate thereof. For example, compounds containing a carboxy group can form physiologically hydrolyzable esters which serve as prodrugs by being hydrolyzed in the body to yield formula (I) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula (I) include $C_{1-6}$alkylbenzyl, 4-methoxybenzyl, indanyl, phthalyl, methoxymethyl, $C_{1-6}$alkanoyloxy-$C_{1-6}$alkyl, e.g. acetoxymethyl, pivaloyloxymethyl or propionyloxymethyl, $C_{1-6}$alkoxycarbonyloxy-$C_{1-6}$alkyl, e.g. methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Prodrug ester examples include the following groups: (1-alkanoyloxy)alkyl such as,

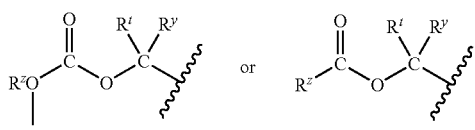

wherein $R^z$, $R^t$ and $R^y$ are H, alkyl, aryl or arylalkyl; however, $R^zO$ cannot be HO.

Examples of such prodrug esters include

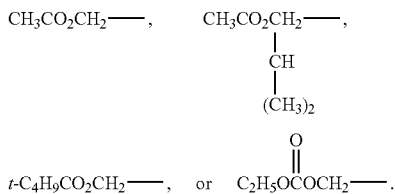

Other examples of suitable prodrug esters include

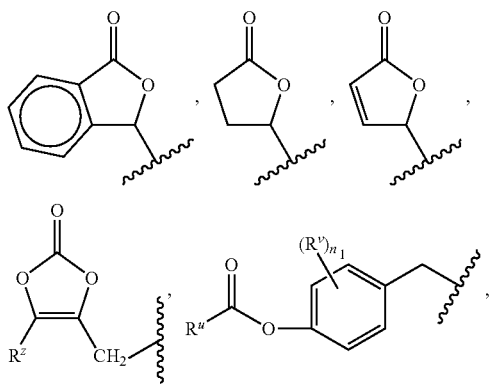

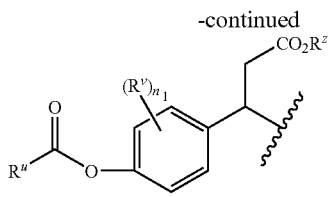

wherein $R_z$ can be H, alkyl (such as methyl or t-butyl), arylalkyl (such as benzyl) or aryl (such as phenyl); $R^v$ is H, alkyl, halogen or alkoxy, $R^u$ is alkyl, aryl, arylalkyl or alkoxyl, and $n_1$ is 0, 1 or 2.

For further examples of prodrug derivatives, see:

a) *Design of Prodrugs*, edited by H. Bundgaard, (Elsevier, 1985) and *Methods in Enzymology*, Vol. 112, pp. 309-396, edited by K. Widder, et al. (Academic Press, 1985);

b) *A Textbook of Drug Design and Development*, edited by Krosgaard-Larsen and H. Bundgaard, Chapter 5, "Design and Application of Prodrugs," by H. Bundgaard, pp. 113-191 (1991); and c) H. Bundgaard, *Advanced Drug Delivery Reviews*, 8, pp. 1-38 (1992).

The term tautomer refers to compounds of the formula (I) and salts thereof that may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention.

The terms pharmaceutically acceptable "salt" and "salts" refer to basic salts formed with inorganic and organic bases. Such salts include ammonium salts; alkali metal salts, such as lithium, sodium and potassium salts (which are preferred); alkaline earth metal salts, such as calcium and magnesium salts; salts with organic bases, such as amine like salts (e.g., dicyclohexylamine salt, benzathine, N-methyl-D-glucamine, and hydrabamine salts); and salts with amino acids like arginine, lysine and the like; and zwitterions, the so-called "inner salts". Nontoxic, pharmaceutically acceptable salts are preferred, although other salts are also useful, e.g., in isolating or purifying the product.

The term pharmaceutically acceptable "salt" and "salts" also includes acid addition salts. These are formed, for example, with strong inorganic acids, such as mineral acids, for example sulfuric acid, phosphoric acid or a hydrohalic acid such as HCl or HBr, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methanesulfonic acid or p-toluenesulfonic acid.

All stereoisomers of the compounds of the instant invention are contemplated, either in admixture or in pure or substantially pure form. The compounds of the present invention can have asymmetric centers at any of the carbon atoms including any one or the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

The inventive compounds may be in the free or solvate (e.g. hydrate) form.

Combinations

Where desired, the compounds of structure I may be used in combination with one or more other types of therapeutic agents such as immunosuppressants, anticancer agents, antiviral agents, anti-inflammatory agents, anti-fungal agents, antibiotics, anti-vascular hyperproliferation agents, anti-depressive agents, hypolipidemic agents or lipid-lowering agents or lipid modulating agents, antidiabetic agents, antiobesity agents, antihypertensive agents, platelet aggregation inhibitors, and/or anti-osteoporosis agents, which may be administered orally in the same dosage form, in a separate oral dosage form or by injection.

The immunosuppressants which may be optionally employed in combination with compounds of formula I of the invention include cyclosporins, for example cyclosporin A, mycophenolate, interferon-beta, deoxyspergolin, FK-506 or Ant.-IL-2.

The anti-cancer agents which may be optionally employed in combination with compounds of formula I of the invention include azathiprine, 5-fluorouracil, cyclophosphamide, cisplatin, methotrexate, thiotepa, carboplatin, and the like.

The anti-viral agents which may be optionally employed in combination with compounds of formula I of the invention include abacavir, aciclovir, ganciclovir, zidanocin, vidarabine, and the like.

The anti-inflammatory agents which may be optionally employed in combination with compounds of formula I of the invention include non-steroidal anti-inflammatory drugs (NSAIDs) such as ibuprofen, cox-2 inhibitors such as celecoxib, rofecoxib, aspirin, naproxen, ketoprofen, diclofenac sodium, indomethacin, piroxicam, steroids such as prednisone, dexamethasone, hydrocortisone, triamcinolone diacetate, gold compounds, such as gold sodium thiomalate, TNF-α inhibitors such as tenidap, anti-TNF antibodies or soluble TNF receptor, and rapamycin (sirolimus or Rapamune) or derivatives thereof, infliximab (Remicade® Centocor, Inc.). CTLA-4Ig, LEA29Y, antibodies such as anti-ICAM-3, anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and CD154 (a.k.a. "gp39"), such as antibodies specific for CD40 and/or CD154, fusion proteins such as etanercept, fusion proteins constructed from CD40 and/or CD154gp39 (e.g. CD401g and CD8gp39), inhibitors, such as nuclear translocation inhibitors, of NF-kappa B function, such as deoxyspergualin (DSG).

The anti-fungal agents which may be optionally employed in combination with compounds of formula I of the invention include fluconazole, miconazole, amphotericin B, and the like.

The antibiotics which may be optionally employed in combination with compounds of formula I of the invention include penicillin, tetracycline, amoxicillin, ampicillin, erythromycin, doxycycline, vancomycin, minocycline, clindamycin or cefalexin.

The anti-vascular hyperproliferation agents which may be optionally employed with compounds of formula I of the invention include methotrexate, leflunomide, FK506 (tacrolimus, Prograf), The hypolipidemic agent or lipid-lowering agent or lipid modulating agents which may be optionally employed in combination with the compounds of formula I of the invention may include 1, 2, 3 or more MTP inhibitors, HMG CoA reductase inhibitors, squalene synthetase inhibitors, fibric acid derivatives, ACAT inhibitors, lipoxygenase inhibitors, cholesterol absorption inhibitors, ileal $Na^+$/bile acid cotransporter inhibitors, upregulators of LDL receptor activity, bile acid sequestrants, and/or nicotinic acid and derivatives thereof.

MTP inhibitors employed herein include MTP inhibitors disclosed in U.S. Pat. Nos. 5,595,872, 5,739,135, 5,712,279, 5,760,246, 5,827,875, 5,885,983 and U.S. application Ser. No. 09/175,180 filed Oct. 20, 1998, now U.S. Pat. No. 5,962,440. Preferred are each of the preferred MTP inhibitors disclosed in each of the above patents and applications.

All of the above U.S. Patents and applications are incorporated herein by reference.

Most preferred MTP inhibitors to be employed in accordance with the present invention include preferred MTP inhibitors as set out in U.S. Pat. Nos. 5,739,135 and 5,712,279, and 5,760,246.

The most preferred MTP inhibitor is 9-[4-[4-[[2-(2,2,2-trifluoroethoxy)benzoyl]amino]-1-piperidinyl]butyl]-N-(2,2,2-trifluoroethyl)-9H-fluorene-9-carboxamide

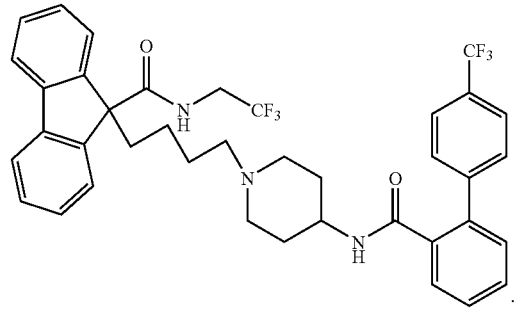

The hypolipidemic agent may be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, itavastatin (Nissan/Sankyo's nisvastatin (NK-104)) disclosed in U.S. Pat. No. 5,011,930, Shionogi-Astra/Zeneca visastatin (ZD-4522) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0,142,146 A2, and quinoline and pyridine derivatives disclosed in U.S. Pat. Nos. 5,506,219 and 5,691,322.

In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al, *J. Med. Chem., Vol.* 31, No. 10, pp 1869-1871 (1988), including isoprenoid (phosphinyl-methyl)phosphonates as well as other known squalene synthetase inhibitors, for example, as disclosed in U.S. Pat. No. 4,871,721 and 4,924,024 and in Biller, S. A., Neuenschwander, K., Ponpipom, M. M., and Poulter, C. D., *Current Pharmaceutical Design*, 2, 1-40 (1996).

In addition, other squalene synthetase inhibitors suitable for use herein include the terpenoid pyrophosphates disclosed by P. Ortiz de Montellano et al, J. Med. Chem., 1977, 20, 243-249, the farnesyl diphosphate analog A and presqualene pyrophosphate (PSQ-PP) analogs as disclosed by Corey and Volante, *J. Am. Chem. Soc.,* 98, 1291-1293 (1976), phosphinylphosphonates reported by McClard, R. W. et al, *J. Am. Chem. Soc.,* 1987, 109, 5544 (1987), and cyclopropanes reported by Capson, T. L., PhD dissertation, Dept. Med. Chem. U of Utah, Abstract, Table of Contents, pp 16, 17, 40-43, 48-51, Summary (June, 1987).

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex®, Policexide®V) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The hypolipidemic agent may be an ACAT inhibitor such as disclosed in, Drugs of the Future 24, 9-15 (1999), (Avasimibe); "The ACAT inhibitor, Cl-1011 is effective in the prevention and regression of aortic fatty streak area in hamsters", Nicolosi et al, *Atherosclerosis* (Shannon, Irel). 137(1), 77-85 (1998) "The pharmacological profile of FCE 27677: a novel ACAT inhibitor with potent hypolipidemic activity mediated by selective suppression of the hepatic secretion of ApoB100-containing lipoprotein", Ghiselli, Giancarlo, *Cardiovasc. Drug Rev.* (1998), 16(1), 16-30; "RP 73163: a bioavailable alkylsulfinyl-diphenylimidazole ACAT inhibitor", Smith, C., et al, *Bioorg. Med. Chem. Lett.* 6(1), 47-50 (1996); "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., *Inflammation: Mediators Pathways* 173-98 (1995), Publisher: CRC, Boca Raton, Fla.; "ACAT inhibitors: potential anti-atherosclerotic agents", Sliskovic et al, *Curr. Med. Chem.* 1(3), 204-25 1994); "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl] ureas with enhanced hypocholesterolemic activity", Stout et al, *Chemtracts: Org. Chem.* 8(6), 359-62 (1995), or TS-962 (Taisho Pharmaceutical Co. Ltd).

The hypolipidemic agent may be an upregulator of LD2 receptor activity such as MD-700 (Taisho Pharmaceutical Co. Ltd) and LY295427 (Eli Lilly).

The hypolipidemic agent may be a cholesterol absorption inhibitor preferably Schering-Plough's ezetimibe (SCH58235) and SCH48461 as well as those disclosed in *Atherosclerosis* 115, 45-63 (1995) and *J. Med. Chem.* 41, 973 (1998).

The hypolipidemic agent may be an ileal $Na^+$/bile acid cotransporter inhibitor such as disclosed in *Drugs of the Future,* 24, 425-430 (1999).

The lipid-modulating agent may be a cholesteryl ester transfer protein (CETP) inhibitor such as Pfizer's CP 529,414 (WO/0038722 and EP 818448) and Pharmacia's SC-744 and SC-795.

The ATP citrate lyase inhibitor which may be employed in the combination of the invention may include, for example, those disclosed in U.S. Pat. No. 5,447,954.

Preferred hypolipidemic agents are pravastatin, lovastatin, simvastatin, atorvastatin, fluvastatin, cerivastatin, itavastatin and visastatin and ZD-4522.

The above-mentioned U.S. patents are incorporated herein by reference. The amounts and dosages employed will be as indicated in the Physician's Desk Reference and/or in the patents set out above.

The compounds of formula I of the invention will be employed in a weight ratio to the hypolipidemic agent (were present), within the range from about 500:1 to about 1:500, preferably from about 100:1 to about 1:100.

The dose administered must be carefully adjusted according to age, weight and condition of the patient, as well as the route of administration, dosage form and regimen and the desired result.

The dosages and formulations for the hypolipidemic agent will be as disclosed in the various patents and applications discussed above.

The dosages and formulations for the other hypolipidemic agent to be employed, where applicable, will be as set out in the latest edition of the Physicians' Desk Reference.

For oral administration, a satisfactory result may be obtained employing the MTP inhibitor in an amount within the range of from about 0.01 mg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor, for example, pravastatin, lovastatin, simvastatin, atorvastatin, fluvastatin or cerivastatin in dosages employed as indicated in the Physician's Desk Reference, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 100 mg, preferably from about 0.5 to about 80 mg, and more preferably from about 1 to about 40 mg.

A preferred oral dosage form, such as tablets or capsules will contain the squalene synthetase inhibitor in an amount of from about 10 to about 500 mg, preferably from about 25 to about 200 mg.

The hypolipidemic agent may also be a lipoxygenase inhibitor including a 15-lipoxygenase (15-LO) inhibitor such as benzimidazole derivatives as disclosed in WO 97/12615, 15-LO inhibitors as disclosed in WO 97/12613, isothiazolones as disclosed in WO 96/38144, and 15-LO inhibitors as disclosed by Sendobry et al "Attenuation of diet-induced atherosclerosis in rabbits with a highly selective 15-lipoxygenase inhibitor lacking significant antioxidant properties", *Brit. J Pharmacology* 120, 1199-1206 (1997), and Cornicelli et al, "15-Lipoxygenase and its Inhibition: A Novel Therapeutic Target for Vascular Disease", *Current Pharmaceutical Design*, 5, 11-20 (1999).

The compounds of formula I and the hypolipidemic agent may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

The preferred hypolipidemic agent is pravastatin, simvastatin, lovastatin, atorvastatin, fluvastatin or cerivastatin as well as niacin and/or cholestagel.

The other antidiabetic agent which may be optionally employed in combination with the compound of formula I may be 1,2,3 or more antidiabetic agents or antihyperglycemic agents including insulin secretagogues or insulin sensitizers, or other antidiabetic agents preferably having a mechanism of action different from the compounds of formula I of the invention, which may include biguanides, sulfonyl ureas, glucosidase inhibitors, PPAR γ agonists, such as thiazolidinediones, aP2 inhibitors, dipeptidyl peptidase IV (DP4) inhibitors, SGLT2 inhibitors, and/or meglitinides, as well as insulin, and/or glucagon-like peptide-1 (GLP-1).

The other antidiabetic agent may be an oral antihyperglycemic agent preferably a biguanide such as metformin or phenformin or salts thereof, preferably metformin HCl.

Where the antidiabetic agent is a biguanide, the compounds of structure I will be employed in a weight ratio to biguanide within the range from about 0.001:1 to about 10:1, preferably from about 0.01:1 to about 5:1.

The other antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the □-cells, with glyburide and glipizide being preferred, which may be administered in the same or in separate oral dosage forms.

The compounds of structure I will be employed in a weight ratio to the sulfonyl urea in the range from about 0.01:1 to about 100:1, preferably from about 0.02:1 to about 5:1.

The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of structure I will be employed in a weight ratio to the glucosidase inhibitor within the range from about 0.01:1 to about 100:1, preferably from about 0.05:1 to about 10:1.

The compounds of structure I may be employed in combination with a PPAR Y agonist such as a thiazolidinedione oral anti-diabetic agent or other insulin sensitizers (which has an insulin sensitivity effect in NIDDM patients) such as troglitazone (Warner-Lambert's Rezulino, disclosed in U.S. Pat. No. 4,572,912), rosiglitazone (SKB), pioglitazone (Takeda), Mitsubishi's MCC-555 (disclosed in U.S. Pat. No. 5,594,016), Glaxo-Welcome's GL-262570, englitazone (CP-68722, Pfizer) or darglitazone (CP-86325, Pfizer, isaglitazone (MIT/J&J), JTT-501 (JPNT/P&U), L-895645 (Merck), R-1 19702 (Sankyo/WL), NN-2344 (Dr. Reddy/NN), or YM-440 (Yamanouchi), preferably rosiglitazone and pioglitazone.

The compounds of structure I will be employed in a weight ratio to the thiazolidinedione in an amount within the range from about 0.01:1 to about 100:1, preferably from about 0.05 to about 10:1.

The sulfonyl urea and thiazolidinedione in amounts of less than about 150 mg oral antidiabetic agent may be incorporated in a single tablet with the compounds of structure I.

The compounds of structure I may also be employed in combination with a antihyperglycemic agent such as insulin or with glucagon-like peptide-1 (GLP-1) such as GLP-1(1-36) amide, GLP-1(7-36) amide, GLP-1(7-37) (as disclosed in U.S. Pat. No. 5,614,492 to Habener, the disclosure of which is incorporated herein by reference), as well as AC2993 (Amylin) and LY-315902 (Lilly), which may be administered via injection, intranasal, inhalation or by transdermal or buccal devices.

Where present, metformin, the sulfonyl ureas, such as glyburide, glimepiride, glipyride, glipizide, chlorpropamide and gliclazide and the glucosidase inhibitors acarbose or miglitol or insulin (injectable, pulmonary, buccal, or oral) may be employed in formulations as described above and in amounts and dosing as indicated in the Physician's Desk Reference (PDR).

Where present, metformin or salt thereof may be employed in amounts within the range from about 500 to about 2000 mg per day which may be administered in single or divided doses one to four times daily.

Where present, the thiazolidinedione anti-diabetic agent may be employed in amounts within the range from about 0.01 to about 2000 mg/day which may be administered in single or divided doses one to four times per day.

Where present insulin may be employed in formulations, amounts and dosing as indicated by the Physician's Desk Reference.

Where present GLP-1 peptides may be administered in oral buccal formulations, by nasal administration or parenterally as described in U.S. Pat. Nos. 5,346,701 (TheraTech), 5,614,492 and 5,631,224 which are incorporated herein by reference.

The other antidiabetic agent may also be a PPAR α/γ dual agonist such as AR-HO39242 (Astra/Zeneca), GW-409544 (Glaxo-Wellcome), KRP297 (Kyorin Merck) as well as those disclosed by Murakami et al, "A Novel Insulin Sensitizer Acts As a Coligand for Peroxisome Proliferation-Activated Receptor Alpha (PPAR alpha) and PPAR gamma. Effect on PPAR alpha Activation on Abnormal Lipid Metabolism in Liver of Zucker Fatty Rats", *Diabetes* 47, 1841-1847 (1998).

The antidiabetic agent may be an SGLT2 inhibitor such as disclosed in U.S. application Ser. No. 09/679,027, filed Oct. 4, 2000 employing dosages as set out therein. Preferred are the compounds designated as preferred in the above application.

The antidiabetic agent may be an aP2 inhibitor such as disclosed in U.S. application Ser. No. 09/391,053, filed Sep. 7, 1999, and in U.S. application Ser. No. 09/519,079, filed Mar. 6, 2000 employing dosages as set out herein. Preferred are the compounds designated as preferred in the above application.

The antidiabetic agent may be a DP4 inhibitor such as disclosed in U.S. application Ser. No. 09/788,173 filed Feb. 16, 2001, WO99/38501, WO99/46272, WO99/67279 (PROBIODRUG), WO99/67278 (PROBIODRUG), WO99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) (preferred) as disclosed by Hughes et al, Biochemistry, 38(36), 11597-11603, (1999), TSL-225 (tryptophyl-1,2,3,4-tetrahydro-isoquinoline-3-carboxylic acid (disclosed by Yamada et al, *Bioorg. & Med. Chem. Lett.* 8 1537-1540 (1998), 2-cyanopyrrolidides and 4-cyanopyrrolidides as disclosed by Ashworth et al, *Bioorg. & Med. Chem. Lett.*, Vol. 6, No. 22, pp 1163-1166 and 2745-2748 (1996) employing dosages as set out in the above references.

The meglitinide which may optionally be employed in combination with the compound of formula I of the invention may be repaglinide, nateglinide (Novartis) or KAD1229 (PF/Kissei), with repaglinide being preferred.

The compound of formula I will be employed in a weight ratio to the meglitinide, PPAR γ agonist, PPAR α/γ dual agonist, aP2 inhibitor, DP4 inhibitor or SGLT2 inhibitor within the range from about 0.01:1 to about 100:1, preferably from about 0.05 to about 10:1.

The other type of therapeutic agent which may be optionally employed with a compound of formula I may be 1, 2, 3 or more of an anti-obesity agent including a beta 3 adrenergic agonist, a lipase inhibitor, a serotonin (and dopamine) reuptake inhibitor, an aP2 inhibitor, a thyroid receptor agonist and/or an anorectic agent.

The beta 3 adrenergic agonist which may be optionally employed in combination with a compound of formula I may be AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, with AJ9677, L750,355 and CP331648 being preferred.

The lipase inhibitor which may optionally be employed in combination with a compound of formula I may be orlistat or ATL-962 (Alizyme), with orlistat being preferred.

The serotonin (and dopoamine) reuptake inhibitor which may be optionally employed in combination with a compound of formula I may be sibutramine, topiramate (Johnson & Johnson) or axokine (Regeneron), with sibutramine and topiramate being preferred.

The thyroid receptor agonist which may be optionally employed in combination with a compound of formula I may be a thyroid receptor ligand as disclosed in WO97/21993 (U. Cal SF), WO99/00353 (KaroBio), GB98/284425 (KaroBio), and U.S. Provisional Application 60/183,223 filed Feb. 17, 2000, with compounds of the KaroBio applications and the above U.S. provisional application being preferred.

The anorectic agent which may be optionally employed in combination with a compound of formula I may be dexamphetamine, phentermine, phenylpropanolamine or mazindol, with dexamphetamine being preferred.

The various anti-obesity agents described above may be employed in the same dosage form with the compound of formula I or in different dosage forms, in dosages and regimens as generally known in the art or in the PDR.

The antihypertensive agents which may be employed in combination with the compound of formula I of the invention include ACE inhibitors, angiotensin II receptor antagonists, NEP/ACE inhibitors, as well as calcium channel blockers, β-adrenergic blockers and other types of antihypertensive agents including diuretics.

The angiotensin converting enzyme inhibitor which may be employed herein includes those containing a mercapto (—S—) moiety such as substituted proline derivatives, such as any of those disclosed in U.S. Pat. No. 4,046,889 to Ondetti et al mentioned above, with captopril, that is, 1-[(2S)-3-mercapto-2-methylpropionyl]-L-proline, being preferred, and mercaptoacyl derivatives of substituted prolines such as any of those disclosed in U.S. Pat. No. 4,316,906 with zofenopril being preferred.

Other examples of mercapto containing ACE inhibitors that may be employed herein include rentiapril (fentiapril, Santen) disclosed in Clin. Exp. Pharmacol. Physiol. 10:131 (1983); as well as pivopril and YS980.

Other examples of angiotensin converting enzyme inhibitors which may be employed herein include any of those disclosed in U.S. Pat. No. 4,374,829 mentioned above, with N-(1-ethoxycarbonyl-3-phenylpropyl)-L-alanyl-L-proline, that is, enalapril, being preferred, any of the phosphonate substituted amino or imino acids or salts disclosed in U.S. Pat. No. 4,452,790 with (S)-1-[6-amino-2-[[hydroxy-(4-phenylbutyl)phosphinyl]oxy]-1-oxohexyl]-L-proline or (ceronapril) being preferred, phosphinylalkanoyl prolines disclosed in U.S. Pat. No. 4,168,267 mentioned above with fosinopril being preferred, any of the phosphinylalkanoyl substituted prolines disclosed in U.S. Pat. No. 4,337,201, and the phosphonamidates disclosed in U.S. Pat. No. 4,432,971 discussed above.

Other examples of ACE inhibitors that may be employed herein include Beecham's BRL 36,378 as disclosed in European Patent Application Nos. 80822 and 60668; Chugai's MC-838 disclosed in C.A. 102:72588v and *Jap. J. Pharmacol.* 40:373 (1986); Ciba-Geigy's CGS 14824 (3-([1-ethoxycarbonyl-3-phenyl-(1S)-propyl]amino)-2,3,4,5-tetrahydro-2-oxo-1-(3S)-benzazepine-1 acetic acid HCl) disclosed in U.K. Patent No. 2103614 and CGS 16,617 (3(S)-[[(1S)-5-amino-1-carboxypentyl]amino]-2,3,4,5-tetrahydro-2-oxo-1H-1-benzazepine-1-ethanoic acid) disclosed in U.S. Pat. No. 4,473,575; cetapril (alacepril, Dainippon) disclosed in Eur. Therap. Res. 39:671 (1986); 40:543 (1986); ramipril (Hoechsst) disclosed in Euro. Patent No. 79-022 and *Curr. Ther. Res.* 40:74 (1986); Ru 44570 (Hoechst) disclosed in *Arzneimittelforschung* 34:1254 (1985), cilazapril (Hoffman-LaRoche) disclosed in *J. Cardiovasc. Pharmacol.* 9:39 (1987); R 31-2201 (Hoffman-LaRoche) disclosed in *FEBS Lett.* 165:201 (1984); lisinopril (Merck), indalapril (delapril) disclosed in U.S. Pat. No. 4,385,051; indolapril (Schering) disclosed in *J. Cardiovasc. Pharmacol.* 5:643, 655 (1983), spirapril (Schering) disclosed in *Acta. Pharmacol. Toxicol.* 59 (Supp. 5): 173 (1986); perindopril (Servier) disclosed in *Eur. J. clin. Pharmacol.* 31:519 (1987); quinapril (Warner- Lambert) disclosed in U.S. Pat. No. 4,344,949 and CI925 (Warner-Lambert) ([3S-[2[R(*)R(*)]]3R(*)]-2-[2-[[1-(ethoxy-carbonyl)-3-phenylpropyl]amino]-1-oxopropyl]-1, 2,3,4-tetrahydro-6,7-dimethoxy-3-isoquinolinecarboxylic acid HCl) disclosed in *Pharmacologist* 26:243, 266 (1984), WY-44221 (Wyeth) disclosed in *J. Med. Chem.* 26:394 (1983).

Preferred ACE inhibitors are captopril, fosinopril, enalapril, lisinopril, quinapril, benazepril, fentiapril, ramipril and moexipril.

NEP/ACE inhibitors may also be employed herein in that they possess neutral endopeptidase (NEP) inhibitory activity and angiotensin converting enzyme (ACE) inhibitory activity. Examples of NEP/ACE inhibitors suitable for use herein include those disclosed in U.S. Pat. Nos. 5,362,727, 5,366, 973, 5,225,401, 4,722,810, 5,223,516, 4,749,688, 5,552,397, 5,504,080, 5,612,359, 5,525,723, European Patent Application 0599,444, 0481,522, 0599,444, 0595,610, European Patent Application 0534363A2, 534,396 and 534,492, and European Patent Application 0629627A2.

Preferred are those NEP/ACE inhibitors and dosages thereof which are designated as preferred in the above patents/applications which U.S. patents are incorporated herein by reference; most preferred are omapatrilat, BMS 189,921 ([S(R*,R*)]-hexahydro-6-[(2-mercapto-1-oxo-3-phenylpropyl)amino]-2,2-dimethyl-7-oxo-1H-azepine-1-acetic acid (gemopatrilat)) and CGS 30440.

The angiotensin II receptor antagonist (also referred to herein as angiotensin II antagonist or AII antagonist) suitable for use herein includes, but is not limited to, irbesartan, losartan, valsartan, candesartan, telmisartan, tasosartan or eprosartan, with irbesartan, losartan or valsartan being preferred.

A preferred oral dosage form, such as tablets or capsules, will contain the ACE inhibitor or AII antagonist in an amount within the range from abut 0.1 to about 500 mg, preferably from about 5 to about 200 mg and more preferably from about 10 to about 150 mg.

For parenteral administration, the ACE inhibitor, angiotensin II antagonist or NEP/ACE inhibitor will be employed in an amount within the range from about 0.005 mg/kg to about 10 mg/kg and preferably from about 0.01 mg/kg to about 1 mg/kg.

Where a drug is to be administered intravenously, it will be formulated in conventional vehicles, such as distilled water, saline, Ringer's solution or other conventional carriers.

It will be appreciated that preferred dosages of ACE inhibitor and AII antagonist as well as other antihypertensives disclosed herein will be as set out in the latest edition of the Physician's Desk Reference (PDR).

Other examples of preferred antihypertensive agents suitable for use herein include omapatrilat (Vanlev®) amlodipine besylate (Norvasc®), prazosin HCl (Minipress®), verapamil, nifedipine, nadolol, diltiazem, felodipine, nisoldipine, isradipine, nicardipine, atenolol, carvedilol, sotalol, terazosin, doxazosin, propranolol, and clonidine HCl (Catapres®).

Diuretics which may be employed in combination with compounds of formula I include hydrochlorothiazide, torasemide, furosemide, spironolactono, and indapamide.

Antiplatelet agents which may be employed in combination with compounds of formula I of the invention include aspirin, clopidogrel, ticlopidine, dipyridamole, abciximab, tirofiban, eptifibatide, anagrelide, and ifetroban, with clopidogrel and aspirin being preferred.

The antiplatelet drugs may be employed in amounts as indicated in the PDR. Ifetroban may be employed in amounts as set out in U.S. Pat. No. 5,100,889.

Antiosteoporosis agents suitable for use herein in combination with the compounds of formula I of the invention include parathyroid hormone or bisphosphonates, such as MK-217 (alendronate) (Fosamax®).

Dosages employed for the above drugs will be as set out in the Physician's Desk Reference.

Pharmaceutical Formulations

The pharmaceutical composition of the invention includes a pharmaceutically acceptable carrier, adjuvant or vehicle that may be administered to a subject, together with a compound of the present invention, and which does not destroy the pharmacological activity thereof. Pharmaceutically acceptable carriers, adjuvants and vehicles that may be used in the pharmaceutical compositions of the present invention include, but are not limited to, the following: ion exchangers, alumina, aluminum stearate, lecithin, self-emulsifying drug delivery systems ("SEDDS") such as d(-tocopherol polyethyleneglycol 1000 succinate), surfactants used in pharmaceutical dosage forms such as Tweens or other similar polymeric delivery matrices, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β- and γ-cyclodextrin, or chemically modified derivatives such as hydroxyalkylcyclodextrins, including 2- and 3-hydroxypropyl-β-cyclodextrins, or other solubilized derivatives may also be used to enhance delivery of the modulators of the present invention.

The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the invention may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The compounds of the invention may, for example, be administered in a form suitable for immediate release or extended release. Immediate release or extended release may be achieved by the use of suitable pharmaceutical compositions including the compounds of the invention, or, particularly in the case of extended release, by the use of devices such as subcutaneous implants or osmotic pumps. The compounds of the invention may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or favoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compounds may also be delivered through the oral cavity by sublingual and/or buccal administration. Molded tablets, compressed tablets or freeze-dried tablets are exemplary forms which may be used. Exemplary compositions include those formulating the compound(s) of the invention with fast dissolving diluents such as mannitol, lactose, sucrose and/or cyclodextrins. Also included in such formulations may be high molecular weight excipients such as celluloses (Avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

Exemplary compositions for rectal administration include suppositories which may contain, for example, a suitable non-irritating excipient, such as cocoa butter, synthetic glyceride esters or polyethylene glycols, which are solid at ordinary temperatures, but liquefy and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.1 to 500 mg/kg of body weight of active compound per day, or between 5 and 2000 mg per day which may be administered in a single dose or in the form of individual divided doses, such as from 1 to 5 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like.

A typical capsule for oral administration contains compounds of structure I (250 mg), lactose (75 mg) and magnesium stearate (15 mg). The mixture is passed through a 60 mesh sieve and packed into a No. 1 gelatin capsule.

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

The compounds of formula (I) of the invention are glucocorticoid receptor modulators as shown either by their ability to bind glucocorticoid receptors in GR binding assays, or by their ability to inhibit AP-1 activity as indicated in cellular transrespressional assays, and cause none to minimal transactivation as indicated in cellular transcriptional assays.

Examples of the invention have been tested in at least one of the assays described below and have glucocorticoid receptor (GR)/Dexamethasone (Dex) inhibition activity (>25%, preferably >95% at 10 µM) and/or AP-1 inhibition activity ($EC_{50}$ less than 15 µM).

Identical and/or similar assays are described in copending provisional application No. 60/396,907, filed Jul. 18, 2002 which is incorporated in its entirety herein by reference.

GR (Dex) Binding Assay

In order to measure the binding of compounds to Site I on the glucocorticoid receptor a commercially available kit was used (Glucocorticoid receptor competitor assay kit, Panvera Co., Madison, Wis.). Briefly, a cell lysate containing recombinantly expressed human full-length glucocorticoid receptor was mixed with a fluorescently labeled glucocorticoid (4 nM FITC-dexamethasone) plus or minus test molecule. After one hour at room temperature, the fluorescence polarization (FP) of the samples were measured. The FP of a mixture of receptor, fluorescent probe (i.e. FITC-dexamethasone) and 11 mM dexamethasone represented background fluorescence or 100% inhibition, whereas, the FP of the mixture without dexamethasone was taken to be 100% binding. The percentage inhibition of test molecules were then compared to the sample with 1 mM dexamethasone and expressed as % relative binding activity with dexamethasone being 100% and no inhibition is 0%. Test molecules were analyzed in the concentration range from 0.1 nM to 40 µM.

Site I binding assays for any NHR (Nuclear Hormone Receptor) are conducted similarly to the above. An appropriate cell lysate or purified NHR is used as the source of the NHR. The fluorescent probe and unlabeled competitor are appropriate for the specific NHR, i.e. are ligands for the specific NHR.

Cellular Transrepressional Assay

To measure the ability of test molecules to inhibit AP-1 induced transcriptional activity we utilized an A549 cell which was stably transfected with a plasmid containing 7×AP-1 DNA binding sites (pAP-1-Luc plasmid, Stratagene Co. La Jolla, Calif.) followed by the gene for luciferase. Cells were activated with 10 ng/ml of phorbol myristic acid (PMA) plus or minus test molecules for 7 hours. After 7 hours a luciferase reagent was added to measure luciferase enzymatic activity in the cell. After a 10 minute incubation of luciferase reagent with cells, luminescence was measured in a TopCount luminescence counter. Repression of AP-1 activity was calculated as the percentage decrease in the signal induced by PMA alone. Test molecules were analyzed in the concentration range from 0.1 nM to 40 µM. EC50s were determined by using standard curve fitting methods such as Excel fit (Microsoft Co.). An EC50 is the test molecule concentration at which there is a 50% repression of the maximal inhibition of transcription, i.e. a 50% reduction of AP-1 activity.

Other reporters and cell lines also may be used in a cellular transrepressional assay. A similar assay may be performed in which NF-κB activity can be measured. A plasmid containing NF-κB DNA binding sites, such as pNF-κB-Luc, (Stratagene, LaJolla Calif.), and PMA, or another stimulus, such as TNF-α or lipopolysaccharide, is used to activate the NF-κB pathway. NF-κB assays similar to that described in Yamamoto K., et al., *J Biol Chem* December 29; 270(52):31315-20 (1995) may be used.

The cellular transrepressional assays described above may be used to measure transrepression by any NHR. One of skill in the art will understand that assays may require the addition of components, such as a stimulus (eg. PMA, lipopolysaccharide, TNF-α, etc) which will induce transcription mediated by AP-1 or NF-κB. Additionally, AR mediated transrepression may be measured by the assay described in Palvimo J J, et al. *J Biol Chem* September 27; 271(39):24151-6 (1996), and PR mediated transrepression may be measured by the assay described in Kalkhoven E., et al. *J Biol Chem* March 15; 271(11):6217-24 (1996).

Abbreviations

The following abbreviations are employed in the following Preparations and Examples:
Ph=phenyl
Bn=benzyl
t-Bu=tertiary butyl
Me=methyl
Et=ethyl
TMS=trimethylsilyl
TMSN$_3$=trimethylsilyl azide
TBS=tert-butyldimethylsilyl
FMOC=fluorenylmethoxycarbonyl
Boc=tert-butoxycarbonyl
Cbz=carbobenzyloxy or carbobenzoxy or benzyloxycarbonyl
THF=tetrahydrofuran
Et$_2$O=diethyl ether
hex=hexanes
EtOAc=ethyl acetate
DMF=dimethyl formamide
MeOH=methanol
EtOH=ethanol
i-PrOH=isopropanol
DMSO=dimethyl sulfoxide
DME=1,2 dimethoxyethane
DCE=1,2 dichloroethane
HMPA=hexamethyl phosphoric triamide
HOAc or AcOH=acetic acid
TFA=trifluoroacetic acid
TFAA=trifluoroacetic anhydride
i-Pr$_2$NEt=diisopropylethylamine
Et$_3$N=triethylamine
NMM=N-methyl morpholine
DMAP=4-dimethylaminopyridine
NaBH$_4$=sodium borohydride
NaBH(OAc)$_3$=sodium triacetoxyborohydride
DIBALH=diisobutyl aluminum hydride
LAH or LiAlH$_4$=lithium aluminum hydride
n-BuLi=n-butyllithium
LDA=lithium diisopropylamide
Pd/C=palladium on carbon
PtO$_2$=platinum oxide
KOH=potassium hydroxide
NaOH=sodium hydroxide
LiOH=lithium hydroxide
K$_2$CO$_3$=potassium carbonate
NaHCO$_3$=sodium bicarbonate
DBU=1,8-diazabicyclo[5.4.0]undec-7-ene
EDC (or EDC.HCl) or EDCI (or EDCI.HCl) or EDAC=3-ethyl-3'-(dimethylamino) propyl- carbodiimide hydrochloride (or 1-(3-dimethylaminopropyl)-3-ethylcarbodiimide hydrochloride)
HOBT or HOBT.H$_2$O=1-hydroxybenzotriazole hydrate
HOAT=1-Hydroxy-7-azabenzotriazole
BOP reagent=benzotriazol-1-yloxy-tris(dimethylamino) phosphonium hexafluorophosphate
NaN(TMS)$_2$=sodium hexamethyldisilazide or sodium bis(trimethylsilyl)amide
Ph$_3$P=triphenylphosphine
Pd(OAc)$_2$=Palladium acetate
(Ph$_3$P)$_4$Pd$^o$=tetrakis triphenylphosphine palladium
DEAD=diethyl azodicarboxylate
DIAD=diisopropyl azodicarboxylate
Cbz-Cl=benzyl chloroformate
CAN=ceric ammonium nitrate
SAX=Strong Anion Exchanger
SCX=Strong Cation Exchanger
Ar=argon
N$_2$=nitrogen
min=minute(s)
h or hr=hour(s)
L=liter
mL=milliliter
μL=microliter
g=gram(s)
mg=milligram(s)
mol=moles
mmol=millimole(s)
meq=milliequivalent
RT=room temperature
sat or sat'd=saturated
aq.=aqueous
TLC=thin layer chromatography
HPLC=high performance liquid chromatography
Reverse phase HPLC=reverse phase high performance liquid chromatography, using a YMC ODS S5 column and a binary solvent A/solvent B eluents
Solvent A=10% MeOH-90% H$_2$O-0.1% TFA
Solvent B=90% MeOH-10% H$_2$O-0.1% TFA
LC/MS=high performance liquid chromatography/mass spectrometry
MS or Mass Spec=mass spectrometry
NMR=nuclear magnetic resonance
NMR spectral data: s=singlet; d=doublet; m=multiplet; br=broad; t=triplet
mp=melting point

EXAMPLES

The following Examples illustrate embodiments of the inventive compounds and starting materials, and are not intended to limit the scope of the claims.

Examples 1 and 2

2-[(5R)-1-(4-fluorophenyl)-5,6-dimethyl-4,5-dihydro-1H-indazol-5-yl]-1-phenylethanol Isomers A and B (1a) p-Toluenesulfonic acid monohydrate (285 mg, 0.015 eq) was added to a solution of ethyl 2-methylacetoacetate (14.4 g, 100 mmol) and (S)-(−)-α-methylbenzylamine (13.3 g, 1.1 eq) in toluene (200 mL). The resultant mixture was heated to reflux with a Dean-Stark trap for 6 h, cooled to room temperature and concentrated in vacuo. The residue was purified by distillation under vacuum to afford the desired enamine (19.3 g, 78%). MS found: (M+H)$^+$=248.

(1b) Methyl vinyl ketone (5.93 g, 1.1 eq) was added to a solution of zinc chloride (525 mg, 0.05 eq) in toluene (200 mL) at 0° C. and the mixture was stirred at that temperature for 1 h. A solution of the enamine from reaction 1a (19.0 g, 76.9 mmol) in toluene (50 mL) was added to the above mixture dropwise over 1h at 0° C. The resultant mixture was stirred at 0° C. for 1 h, treated with 10% acetic acid in water (50 mL) and warmed to room temperature for 2 h. After addition of ethyl acetate (600 mL), the mixture was washed with water (100 mL), followed by brine (100 mL). The organic layer was dried over MgSO$_4$ and concentrated in vacuo. The residue was chromatographed over silica gel (ethyl acetate-hexane, 0 to 50%) to yield the desired ketoester (5.20 g, 34%).

(1c) Piperidine (1.01 g, 0.8 eq) and acetic acid (942 mg, 0.95 eq) were added to the ketoester from reaction 1b (3.20 g, 14.9 mmol) at room temperature. The resultant mixture was heated to 80° C. for 2 h, cooled to room temperature, diluted with ethyl acetate (300 mL), washed with water (20 mL), followed by brine (20 mL), dried over MgSO$_4$ and concentrated in vacuo. The residue was chromatographed over silica gel (ethyl acetate-hexane, 0 to 50%) to yield the desired Hagemann's ester (2.30 g, 79%), which was found to be 70% e.e. based on chiral HPLC analysis (AS column). MS found: (M+H)$^+$=197.

(1d) Ethanol (0.1 mL) was added to a mixture of the ester from reaction 1c (2.00 g, 10.2 mmol), ethyl formate (1.21 g, 1.6 eq), sodium (282 mg, 1.2 eq) in dry ether (50 mL) at room temperature. After 2 h at room temperature, additional ethanol (0.3 mL) was added and the mixture stirred at room temperature for additional 3 h. Following addition of water (20 mL), the ether layer was separated and washed with water (3×10 mL). The combined aqueous layer was adjusted pH=2~3 with 1N HCl and extracted with ethyl acetate (3×80 mL). The combined organic phase was washed with water (30 mL), followed by brine (30 mL), dried over MgSO$_4$ and concentrated in vacuo. The residue was chromatographed over silica gel (ethyl acetate-hexane, 0 to 50%) to yield the desired aldehyde (1.70 g, 74%). MS found: (M+H)$^+$=225.

(1e) Sodium acetate (685 mg, 1.1 eq) was added to a solution of the aldehyde from reaction 1d (1.70 g, 7.59 mmol) and 4-fluorophenylhydrazine hydrochloride (1.36 g, 1.1 eq) in acetic acid (20 mL) at room temperature. After 4 h at rt, the mixture was carefully quenched with saturated sodium carbonate (300 mL) and extracted with ethyl acetate (3×200 mL). The combined organic phase was washed with brine (100 mL), dried over MgSO$_4$ and concentrated in vacuo. The residue was chromatographed over silica gel (ethyl acetate-hexane, 0 to 50%) yielded the desired ester (2.05 g, 86%). MS found: (M+H)$^+$=315.

(1f) A 1.5 M solution of DIBAL in toluene (7.64 mL, 1.8 eq) was added dropwise to a solution of the ester from reaction 1e (2.00 g, 6.37 mmol) in dichloromethane (80 mL) at −78° C. over 0.5 h. After 0.5 h at −78° C., the mixture was quenched with methanol (10 mL), warmed to room temperature, diluted with ethyl acetate (500 mL), washed with water (2×80 mL), followed by brine (80 mL), dried over MgSO$_4$ and concentrated in vacuo. The residue was chromatographed over silica gel (ethyl acetate-hexane, 0 to 50%) to yield the desired aldehyde (1.15 g, 67%). MS found: (M+H)$^+$=271.

(1g) A 1.0 M THF solution of sodium bis(trimethylsilyl) amide (10.7 mL, 2.9 eq) was added dropwise to a solution of (methoxymethyl)triphenylphosphonium chloride (3.81 g, 3.0 eq) in THF (50 mL) at −78° C. After 1 h at −78° C., a solution of the aldehyde from reaction 1f (1.00 g, 3.70 mmol) in THF (5 mL) was added dropwise. After 2 h −78° C., the mixture was quenched with water (20 mL), diluted with ether (300 mL), washed with water (50 mL), followed by brine (50 mL), dried over MgSO$_4$ and concentrated in vacuo. The residue was chromatographed over silica gel (ethyl acetate-hexane, 0 to 50%) to yield the desired enol ether (760 mg, 61%). MS found: (M+H)$^+$=298.

(1h) Pyridinium p-toluenesulfonate (1.23 g, 2.0 eq) was added to a solution of the enol ether from reaction 1g (730 mg, 2.45 mmol) in THF/H$_2$O (25 mL, 10:1). After 12 h at reflux, the mixture was cooled to room temperature, diluted with ether (300 mL), washed with water (50 mL), followed by brine (50 mL), dried over MgSO$_4$ and concentrated in vacuo. The residue was chromatographed over silica gel (ethyl acetate-hexane, 0 to 50%) to yield the aldehyde (630 mg, 91%), which was purified using chiral OJ column (isocratic, i-PrOH/heptane, 20%) to provide the major enantiomer as the desired aldehyde (400 mg, >98% ee). MS found: (M+H)$^+$=285.

(1i) A solution of the homochiral aldehyde from reaction 1h (30 mg, 0.106 mmol) in THF (2 mL) was added to 1.0 M solution of phenylmagnesium bromide in THF (1.06 mL, 10 eq) at room temperature. After 0.5 h, the mixture was quenched with water (1 mL), diluted with ethyl acetate (60 mL), washed with water (5 mL), followed by brine (5 mL), dried over MgSO$_4$ and concentrated in vacuo. The residue was chromatographed over silica gel (ethyl acetate-hexane, 0 to 60%) to yield the desired alcohol as a mixture of two diastereomers (30 mg), which was separated by chiral AD column (isocratic, i-PrOH/heptane, 20%) to yield Example 1 (12 mg, 31%, isomer A, faster eluent) and Example 2 (11 mg, 29%, isomer B, slower eluent). MS found: (M+H)$^+$=263.

Examples 3 and 4

1-(4-fluorophenyl)-2-[(5R)-1-(4-fluorophenyl)-5,6-dimethyl-4,5-dihydro-1H-indazol-5-yl]ethanol Isomers A and B In an analogous procedure to reaction 1i, with appropriate starting materials, the homochiral aldehyde from reaction 1h (30 mg, 0.106 mmol) was converted to Example 3 (7 mg, 17%, isomer A, faster eluent on chiral AD column) and Example 4 (15 mg, 37%, isomer B, slower eluent). MS found: (M+H)$^+$=338 1.

Examples 5 and 6

2-[(5R)-1-(4-fluorophenyl)-5,6-dimethyl-4,5-dihydro-1H-indazol-5-yl]-1-[4-(methyloxy) phenyl]ethanol Isomers A and B In an analogous procedure to reaction 1i, with appropriate starting materials, the homochiral aldehyde from reaction 1h (30 mg, 0.106 mmol) was converted to Example 5 (13 mg, 31%, isomer A, faster eluent on chiral AD column) and Example 6 (12 mg, 29%, isomer B, slower eluent). MS found: (M+H)$^+$=393.

Examples 7 and 8

1-(4-fluorophenyl)-3-[(5R)-1-(4-fluorophenyl)-5,6-dimethyl-4,5-dihydro-1H-indazol-5-yl]propan-2-ol Isomers A and B In an analogous procedure to reaction 1i, with appropriate starting materials, the homochiral aldehyde from reaction 1h (30 mg, 0.106 mmol) was converted to Example 7 (10 mg, 24%, isomer A, faster eluent on chiral AD column) and Example 8 (10 mg, 24%, isomer B, slower eluent). MS found: (M+H)$^+$=395.

Examples 9 and 10

1-[(5R)-1-(4-fluorophenyl)-5,6-dimethyl-4,5-dihydro-1H-indazol-5-yl]hex-5-en-2-ol Isomers A and B In an analogous procedure to reaction 1i, with appropriate starting materials, the homochiral aldehyde from reaction 1h (30 mg, 0.106 mmol) was converted to Example 9 (7 mg, 19%, isomer A, faster eluent on chiral AD column) and Example 10 (9 mg, 25%, isomer B, slower eluent). MS found: (M+H)$^+$=341.

Examples 11 and 12

2-[(5R)-1-(4-fluorophenyl)-5,6-dimethyl-4,5-dihydro-1H-indazol-5-yl]-1-naphthalen-1-ylethanol Isomers A and B In an analogous procedure to reaction 1i with appropriate starting materials, the homochiral aldehyde from reaction 1h (30 mg, 0.106 mmol) was converted to Example 11 (12 mg, 27%, isomer A, faster eluent on chiral OD column) and Example 12 (15 mg, 27%, isomer B, slower eluent). MS found: (M+H)$^+$=413.

Examples 13 and 14

2-[(5R)-1-(4-fluorophenyl)-5,6-dimethyl-4,5-dihydro-1H-indazol-5-yl]-1-naphthalen-2-ylethanol Isomers A and B In an analogous procedure to reaction 1i, with appropriate starting materials, the homochiral aldehyde from reaction 1h (30 mg, 0.106 mmol) was converted to Example 13 (11 mg, 25%, isomer A, faster eluent on chiral OD column) and Example 14 (11 mg, 25%, isomer B, slower eluent). MS found: (M+H)$^+$=413.

Examples 15 and 16

1-biphenyl-2-yl-2-[(5R)-1-(4-fluorophenyl)-5,6-dimethyl-4,5-dihydro-1H-indazol-5-yl]ethanol Isomers A and B A 1.7 M hexane solution of tert-butyllithium (1.24 mL, 20 eq) was added to a solution of 2-bromobiphenyl (247 mg, 10 eq) in ether (10 ml) at 0° C. and the mixture was stirred at room temperature for 0.5 h. A solution of the homochiral aldehyde from reaction 1h (30 mg, 0.106 mmol) in ether (2 mL) was added. After 0.5 h at room temperature, the mixture was quenched with saturated NH$_4$Cl (2 mL), diluted with ethyl acetate (60 mL), washed with water (5 mL), followed by brine (5 mL), dried over MgSO$_4$ and concentrated in vacuo. The residue was chromatographed over silica gel (ethyl acetate-hexane, 0 to 60%) to yield the desired alcohol as a mixture of two diastereomers (29 mg), which was subsequently separated by chiral AD column (isocratic, i-PrOH/heptane, 15%) to yield Example 15 (10 mg, 22%, isomer A, faster eluent) and Example 16 (10 mg, 22%, isomer B, slower eluent). MS found: (M+H)$^+$=439.

Examples 17 and 18

2-[(5R)-1-(4-fluorophenyl)-5,6-dimethyl-4,5-dihydro-1H-indazol-5-yl]-1-(3-thienyl)ethanol Isomers A and B In an analogous procedure to reaction 1i, with appropriate starting materials, the homochiral aldehyde from reaction 1h (30 mg, 0.106 mmol) was converted to Example 17 (12 mg, 31%, isomer A, faster eluent on chiral OD column) and Example 18 (12 mg, 31%, isomer B, slower eluent). MS found: (M+H)$^+$=369.

Examples 19 and 20

2-[(5R)-1-(4-fluorophenyl)-5,6-dimethyl-4,5-dihydro-1H-indazol-5-yl]-1-(2-thienyl)ethanol Isomers A and B In an analogous procedure to reaction 1i, with appropriate starting materials, the homochiral aldehyde from reaction 1h (30 mg, 0.106 mmol) was converted to Example 19 (10 mg, 26%, isomer A, faster eluent on chiral AD column) and Example 20 (10 mg, 26%, isomer B, slower eluent). MS found: (M+H)$^+$=369.

Examples 21 and 22

1-(1-benzothien-3-yl)-2-[(5R)-1-(4-fluorophenyl)-5,6-dimethyl-4,5-dihydro-1H-indazol-5-yl]ethanol Isomers A and B In an analogous procedure to the synthesis of Examples 15 & 16, with appropriate starting materials, the homochiral aldehyde from reaction 1h (30 mg, 0.106 mmol) was converted to Example 21 (13 mg, 29%, isomer A, faster eluent on chiral OD column) and Example 22 (13 mg, 29%, isomer B, slower eluent). MS found: (M+H)$^+$=419.

Example 23

2-[(5R)-1-(4-fluorophenyl)-5,6-dimethyl-4,5-dihydro-1H-indazol-5-yl]ethanol

Sodium borohydride (5.3 mg, 4.0 eq) was added to a solution of the homochiral aldehyde from reaction 1h (10 mg, 0.035 mmol) in methanol (1 mL) at 0° C. After 0.5 h at 0° C., the mixture was quenched with saturated NH$_4$Cl (1 mL), diluted with ethyl acetate (60 mL), washed with water (5 mL), followed by brine (5 mL), dried over MgSO$_4$ and concentrated in vacuo. The residue was chromatographed over silica gel (ethyl acetate-hexane, 20 to 70%) to yield Example 23 (8.0 mg, 79%). MS found: (M+H)$^+$=287.

Example 24

2-[(5R)-1-(4-fluorophenyl)-5,6-dimethyl-4,5-dihydro-1H-indazol-5-yl]-1-phenylethanone 4-Methylmorpholine (63 mg, 1.5 eq) was added to a solution of the diastereomeric mixture of the alcohol from reaction 1i (150 mg, 0.414 mmol) in dichloromethane (5 mL) at 0° C. After 5 minutes, TPAP (145 mg, 1.0 eq) was added. The mixture was stirred at 0° C. for 1 h, diluted with ethyl acetate (100 mL), washed with water (10 mL), followed by brine (10 mL), dried over MgSO$_4$ and concentrated in vacuo. The residue was chromatographed over silica gel (ethyl acetate-hexane, 10 to 50%) to yield Example 24 (125 mg, 84%). MS found: (M+H)$^+$=361.

Examples 25 and 26

1-[(5R)-1-(4-fluorophenyl)-5,6-dimethyl-4,5-dihydro-1H-indazol-5-yl]-2-phenylpropan-2-ol Isomers A and B A 1.5 M ether solution of methyllithium (1.0 mL, 15 eq) was added to a solution of the ketone from Example 24 (36 mg, 0.100 mmol) in THF (2 mL) at 0° C. After 0.5 h at 0° C., the mixture was quenched with water (1 mL), diluted with ethyl acetate (60 mL), washed with water (5 mL), followed by brine (5 mL), dried over MgSO$_4$ and concentrated in vacuo. The residue was chromatographed over silica gel (ethyl acetate-hexane, 10 to 60%) to yield the desired alcohol as a mixture of two diastereomers (24 mg), which was subsequently separated by chiral OD column (isocratic, i-PrOH/heptane, 15%) to yield Example 25 (10 mg, 27%, isomer A, faster eluent) and Example 26 (3.5 mg, 9%, isomer B, slower eluent). MS found: (M+H)$^+$=377.

Examples 27 and 28

1,1,1-trifluoro-3-[(5R)-1-(4-fluorophenyl)-5,6-dimethyl-4,5-dihydro-1H-indazol-5-yl]-2-phenylpropan-2-ol Isomers A and B (Trifluoromethyl)trimethylsilane (142 mg, 10 eq) and tetramethylammonium fluoride (1 mg, 0.1 eq) were added to a solution of the ketone from Example 24 (36 mg, 0.100 mmol) in THF (2 mL) at room temperature. After 12 h at room temperature, 40% aqueous HF (1 mL) was added. The mixture heated to 50° C. for 4 h, cooled to room temperature, diluted with ethyl acetate (60 mL), washed with water (5 mL), followed by brine (5 mL), dried over MgSO$_4$ and concentrated in vacuo. The residue was chromatographed over silica gel (ethyl acetate-hexane, 10 to 60%) to yield the desired alcohol as a mixture of two diastereomers (10 mg), which was subsequently separated by chiral AD column (isocratic, i-PrOH/heptane, 8%) to yield Example 27 (3.5 mg, 8%, isomer A, faster eluent) and Example 28 (3.5 mg, 8%, isomer B, slower eluent). MS found: (M+H)$^+$=431.

Examples 29 and 30

2-[(5R)-6-cyclopropyl-1-(4-fluorophenyl)-5-methyl-4,5-dihydro-1H-indazol-5-yl]-1-phenylethanol Isomers A and B (29a) Potassium carbonate (9.11 g, 1.1 eq) was added to a mixture of ethyl 3-cyclopropyl-3-oxopropanoate (9.36 g, 60.0 mmol) and iodomethane (8.95 g, 1.05 eq) in acetone (200 mL) at room temperature. The mixture was stirred at room temperature for 24 h, then filtered and the filtrate was concentrated. The residue was dissolved in ether (300 mL), washed with water (30 mL), followed by brine (30 mL), dried over MgSO$_4$ and concentrated to yield the desired the ester as crude oil (9.80 g). MS found: (M+Na)$^+$=193.

(29b) The ester from reaction 29a (9.80 g, 60.0 mmol) and methyl vinyl ketone (4.63 g, 1.1 eq) were added to a suspension of sodium hydride (72 mg, 0.03 eq, 60%) in benzene (50 mL) at room temperature. After 3 h at room temperature, the mixture was quenched with water (10 mL), diluted with ethyl acetate (300 mL), washed with water (30 mL), followed by brine (5 mL), dried over MgSO$_4$ and concentrated. The residue was dissolved in acetic acid (3.0 mL) and piperidine (4.0 mL) and the solution was heated to 80° C. for 5 h. After cooling to room temperature, the mixture was diluted with ethyl acetate (600 mL), washed with water (50 mL), followed by brine (50 mL), dried over MgSO$_4$ and concentrated. The residue was purified by distillation under reduced pressure to yield the desired Hagemann's ester (7.20 g, 54%). MS found: (M+H)$^+$=223.

(29c) Using a procedure analogous to reaction 1d with appropriate starting materials, the ester from reaction 29b (7.00 g, 31.5 mmol) was converted to the desired aldehyde as a crude oil (7.70 g). MS found: (M+H)$^+$=251.

(29d) Using a procedure analogous to reaction J, with appropriate starting materials, the aldehyde from reaction 29c (7.70 g, 31.5 mmol) was converted to the desired ester (7.50 g, 70%). MS found: (M+H)$^+$=341.

(29e) Using a procedure analogous to reaction 1f, with appropriate starting materials, the ester from reaction 29d (7.00 g, 20.6 mmol) was converted to the desired aldehyde (4.30 g, 70%). MS found: (M+H)$^+$=297.

(29f) Using a procedure analogous to reaction 1g, with appropriate starting materials, the aldehyde from reaction 29e (2.00 g, 6.75 mmol) was converted to the desired enol ether (2.00 g, 91%). MS found: (M+H)$^+$=325.

(29g) Using a procedure analogous to reaction 1h, with appropriate starting materials, the enol ether from reaction 29f (2.00 g, 6.17 mmol) was converted to the desired aldehyde (1.20 g, 62%). MS found: (M+H)$^+$=311. A portion of the racemic aldehyde (500 mg) was subsequently separated by chiral OJ column (isocratic, i-PrOH/heptane, 10%) to yield enantiomer A (200 mg, 40% yield, >98% ee, faster eluent) and enantiomer B (200 mg, 40% yield, >95% ee, slower eluent).

(29h) Using a procedure analogous to reaction 1i, with appropriate starting materials, the enantiomer A of the aldehyde from reaction 29g (30 mg, 0.097 mmol) was converted to the desired alcohol as a mixture of two diastereomers (25 mg), which was subsequently separated by chiral OD column (isocratic, i-PrOH/heptane, 15%) to yield Example 29 (9.0 mg, 24%, faster eluent) and Example 30 (8.0 mg, 21%, slower eluent). MS found: (M+H)$^+$=389.

Examples 31 and 32

2-[(5S)-6-cyclopropyl-1-(4-fluorophenyl)-5-methyl-4,5-dihydro-1H-indazol-5-yl]-1-phenylethanol

Isomers A and B

Using a procedure analogous to reaction 1i with appropriate starting materials, the enantiomer B of the aldehyde from reaction 29g (30 mg, 0.097 mmol) was converted to the desired alcohol as a mixture of two diastereomers (25 mg), which was subsequently separated by chiral AD column (isocratic, i-PrOH/heptane, 15%) to yield Example 31 (10.0 mg, 27%, faster eluent) and Example 32 (9.0 mg, 24%, slower eluent). MS found: (M+H)$^+$=389.

Examples 33 and 34

2-[(5R)-6-cyclopropyl-1-(4-fluorophenyl)-5-methyl-4,5-dihydro-1H-indazol-5-yl]-1-(2-thienyl)ethanol

Isomers A and B

Using a procedure analogous to reaction 1i, with appropriate starting materials, the enantiomer A of the aldehyde from reaction 29g (30 mg, 0.097 mmol) was converted to the desired alcohol as a mixture of two diastereomers (25 mg), which was subsequently separated by chiral OD column (isocratic, i-PrOH/heptane, 10%) to yield Example 33 (10.0 mg, 26%, faster eluent) and Example 34 (10.0 mg, 26%, slower eluent). MS found: (M+H)$^+$=395.

Example 35

(5R)-1-(4-fluorophenyl)-5-(2-methoxy-2-phenyl-ethyl)-5,6-dimethyl-4,5-dihydro-1H-indazole Sodium hydride (5.0 mg, 3.0 eq, 60% in mineral oil) was added to the alcohol from Example 1 (15 mg, 0.041 mmol) and iodomethane (17.6 mg, 3.0 eq) in DMF (1 mL) at room temperature. The resultant mixture was heated to 45° C. for 1 h, cooled to room temperature, and carefully quenched with water (1 mL). After addition of EtOAc (60 mL), the mixture was washed with water (10 mL), brine (10 mL), dried (MgSO$_4$) and concentrated. Silica gel column chromatography (EtOAc-hexane, 0 to 30%) yielded Example 35 (11.0 mg, 71%). MS found: (M+H)$^+$=377.

Example 36

(5R)-5-(2-ethoxy-2-phenylethyl)-1-(4-fluorophenyl)-5,6-dimethyl-4,5-dihydro-1H-indazole Using a procedure analogous to Example 35, the alcohol from Example 1 (100 mg, 0.276 mmol) was reacted with iodoethane to give Example 36 (95.0 mg, 88%). MS found: (M+H)$^+$=391.

Example 37

(5R)-5-(2-(benzyloxy)-2-phenylethyl)-1-(4-fluorophenyl)-5,6-dimethyl-4,5-dihydro-1H-indazole Sodium hydride (20 mg, 60% in mineral oil) was added to the alcohol from Example 1 (19 mg, 0.0525 mmol) and benzyl bromide (42.8 mg, 5 eq) in DMF (1 mL) at room temperature. The resultant mixture was stirred at room temperature for 1 h, quenched with saturated NH$_4$Cl (5 mL) and water (5 mL), and extracted with 30% EtOAc/hexane (3×10 mL). The combined extracts were washed with brine (2 mL), dried (MgSO$_4$) and concentrated. Silica gel column chromatography (EtOAc-hexane, 0 to 20%) yielded Example 37 (22.4 mg, 94%). MS found: (M+H)$^+$=453.

Example 38

(5R)-1-(4-fluorophenyl)-5,6-dimethyl-5-(2-phenyl-2-propoxyethyl)-4,5-dihydro-1H-indazole In an analogous procedure to the synthesis of Examples 35, Example 1 (8.6 mg, 0.024 mmol) was reacted with 1-bromopropane to give Example 38 (1.8 mg, 19%). MS found: (M+H)$^+$=405.

Example 39

(5R)-5-(2-(allyloxy)-2-phenylethyl)-1-(4-fluorophenyl)-5,6-dimethyl-4,5-dihydro-1H-indazole In an analogous procedure to the synthesis of Examples 35, Example 1 (8.0 mg, 0.022 mmol) was reacted with allyl bromide to give Example 39 (5.4 mg, 61%). MS found: (M+H)$^+$=403.

Example 40

2-((R)-1-(4-fluorophenyl)-5,6-dimethyl-4,5-dihydro-1H-indazol-5-yl)-1-phenylethyl methylcarbamate A CH$_2$Cl$_2$ (0.5 mL) solution of Example 1 (5 mg, 0.014 mmol), methyl isocyanate (0.103 mL) and triethylamine (0.019 mL, 10 eq) was heated in a sealed tube at 80° C. for 6 h. The crude material was purified by flash column chromatography (0-55% EtOAc-hexanes) to give Example 40 (4.8 mg, 84%). MS found: (M+H)$^+$=420.

Example 41

(5R)-1-(4-fluorophenyl)-5-(2-isopropoxy-2-phenyl-ethyl)-5,6-dimethyl-4,5-dihydro-1H-indazole Iron(III) perchlorate (6.0 mg, 0.2 eq) was added to the alcohol from Example 1 (30 mg, 0.083 mmol) in 2-propanol (2 mL). The resultant mixture was heated to 45° C. for 72 h and cooled to room temperature. After addition of EtOAc (100 mL), the mixture was washed with water (10 mL), brine (10 mL), dried (MgSO$_4$) and concentrated. Silica gel column chromatography (EtOAc-hexane, 0 to 30%) yielded Example 41 (20.0 mg, 60%). MS found: (M+H)$^+$=405.

Example 42

(5R)-5-(2-cyclobutoxy-2-phenylethyl)-1-(4-fluorophenyl)-5,6-dimethyl-4,5-dihydro-1H-indazole In an analogous procedure to the synthesis of Examples 41, Example 1 (8.5 mg, 0.023 mmol) was reacted with cyclobutanol to give Example 42 (5.6 mg, 58%). MS found: (M+H)+= 417.

Examples 43 and 44

(5R)-1-(4-fluorophenyl)-5-(2-methoxy-2-(naphthalen-1-yl)ethyl)-5,6-dimethyl-4,5-dihydro-1H-indazole In an analogous procedure to reaction 1i, the homochiral aldehyde from reaction 1h (30 mg, 0.106 mmol) was reacted with 1-naphthylmagnesium bromide to give a 1:1 mixture of alcohols (38.5 mg, 88%). Then using a procedure analogous to Example 35, the alcohols were converted to the desired ether as a mixture of two diastereomers (30 mg). Separation by chiral OD column (isocratic, i-PrOH/heptane, 5%) gave Examples 43 (9.0 mg, 24% isomer A, faster eluent) and 44 (10 mg, 27%, isomer B, slower eluent). MS found: (M+H)+=427.

Example 45

(5R)-1-(4-fluorophenyl)-5-(2-(4-fluorophenyl)-2-methoxyethyl)-5,6-dimethyl-4,5-dihydro-1H-indazole Using a procedure analogous to Example 35, the alcohol from Example 3 (25.0 mg, 0.066 mmol) was reacted with iodomethane to Example 45 (16.0 mg, 62%).
MS found: (M+H)+=395.

Example 46

(5R)-5-(2-ethoxy-2-(4-fluorophenyl)ethyl)-1-(4-fluorophenyl)-5,6-dimethyl-4,5-dihydro-1H-indazole Using a procedure analogous to Example 35, the alcohol from Example 3 (25.0 mg, 0.066 mmol) was reacted with iodoethane to give Example 46 (20.0 mg, 74%). MS found: (M+H)+=409.

Example 47

(5R)-6-cyclopropyl-1-(4-fluorophenyl)-5-(2-methoxy-2-phenylethyl)-5-methyl-4,5-dihydro-1H-indazole Using a procedure analogous to Example 35, the alcohol from Example 30 (20.0 mg, 0.052 mmol) was converted to Example 47 (6.0 mg, 29%). MS found: (M+H)+=403.

Examples 48 and 49

1-(biphenyl-3-yl)-2-((R)-1-(4-fluorophenyl)-5,6-dimethyl-4,5-dihydro-1H-indazol-5-yl)ethanol In an analogous procedure to Examples 15 and 16, the homochiral aldehyde from reaction 1h (30 mg, 0.106 mmol) was reacted with 3-bromobiphenyl to give Examples 48 (10 mg, 22%, isomer A, faster eluent on chiral AD column) and 49 (10 mg, 22%, isomer B, slower eluent). MS found: (M+H)+=439.

Examples 50 and 51

2-((R)-1-(4-fluorophenyl)-5,6-dimethyl-4,5-dihydro-1H-indazol-5-yl)-1-m-tolylethanol In an analogous procedure to reaction 1i, the homochiral aldehyde from reaction 1h (60 mg, 0.211 mmol) was reacted with 3-methylphenylmagnesium bromide to give Examples 50 (17 mg, 21%, isomer A, faster eluent on chiral OD column) and 51 (17 mg, 21%, isomer B, slower eluent). MS found: (M+H)+=377.

Example 52

(5R)-5-(2-ethoxy-2-m-tolylethyl)-1-(4-fluorophenyl)-5,6-dimethyl-4,5-dihydro-1H-indazole Using a procedure analogous to Example 35, the alcohol from Example 51 (12.0 mg, 0.032 mmol) was converted reacted with iodoethane to give Example 52 (8.0 mg, 62%). MS found: (M+H)+=405.

Examples 53 and 54

1-(3-fluorophenyl)-2-((R)-1-(4-fluorophenyl)-5,6-dimethyl-4,5-dihydro-1H-indazol-5-yl)ethanol In an analogous procedure to reaction 1i, the homochiral aldehyde from reaction 1h (40 mg, 0.141 mmol) was reacted with 3-fluorophenylmagnesium bromide to give Examples 53 (14 mg, 26%, isomer A, faster eluent on chiral OD column) and 54 (11 mg, 21%, isomer B, slower eluent). MS found: (M+H)+=338 1.

Example 55

(5R)-5-(2-ethoxy-2-(3-fluorophenyl)ethyl)-1-(4-fluorophenyl)-5,6-dimethyl-4,5-dihydro-1H-indazole Using a procedure analogous to Example 35, the alcohol from Example 54 (5.0 mg, 0.013 mmol) was reacted with iodoethane to give Example 55 (4.0 mg, 75%). MS found: (M+H)+=409.

Examples 56 and 57

2-((R)-1-(4-fluorophenyl)-5,6-dimethyl-4,5-dihydro-1H-indazol-5-yl)-1-(2-methoxyphenyl) ethanol In an analogous procedure to reaction 1i, the homochiral aldehyde from reaction 1h (40 mg, 0.141 mmol) was reacted with 2-methoxyphenylmagnesium bromide to give Examples 56 (14 mg, 25%, isomer A, faster eluent on chiral OD column) and 57 (9.0 mg, 16%, isomer B, slower eluent). MS found: (M+H)+=393.

Example 58

(5R)-1-(4-fluorophenyl)-5-(2-methoxy-2-(2-methoxyphenyl)ethyl)-5,6-dimethyl-4,5-dihydro-1H-indazole Using a procedure analogous to Example 35, the alcohol from Example 57 (15 mg, 0.038 mmol) was reacted with iodomethane to give Example 58 (9.0 mg, 58%). MS found: (M+H)+=407.

Examples 59 and 60

2-((R)-1-(4-fluorophenyl)-5,6-dimethyl-4,5-dihydro-1H-indazol-5-yl)-1-o-tolylethanol In an analogous procedure to reaction 1i, the homochiral aldehyde from reaction 1h (40 mg, 0.141 mmol) was reacted with 2-methylphenylmagnesium bromide to give Examples 59 (15 mg, 28%, isomer A, faster eluent on chiral AD column) and 60 (15 mg, 28%, isomer B, slower eluent). MS found: (M+H)⁺=377.

Example 61

(5R)-1-(4-fluorophenyl)-5-(2-methoxy-2-o-tolyl-ethyl)-5,6-dimethyl-4,5-dihydro-1H-indazole Using a procedure analogous to Example 35, the alcohol from Example 59 (8.0 mg, 0.021 mmol) was reacted with iodomethane to give Examples 61 (3.0 mg, 37%). MS found: (M+H)⁺=391.

Example 62

(5R)-1-(4-fluorophenyl)-5-(2-methoxy-2-o-tolyl-ethyl)-5,6-dimethyl-4,5-dihydro-1H-indazole Using a procedure analogous to Example 35, the alcohol from Example 60 (5.0 mg, 0.013 mmol) was reacted with iodomethane to give Examples 62 (3.0 mg, 59%). MS found: (M+H)⁺=391.

Example 63

(5R)-5-(2-ethoxy-2-o-tolylethyl)-1-(4-fluorophenyl)-5,6-dimethyl-4,5-dihydro-1H-indazole Using a procedure analogous to Example 35, the alcohol from Example 59 (22 mg, 0.059 mmol) was reacted with iodoethane to give Examples 63 (8.0 mg, 34%). MS found: (M+H)⁺=405.

Example 64

(5R)-1-(4-fluorophenyl)-5-(2-methoxy-2-o-tolyl-ethyl)-5,6-dimethyl-4,5,6,7-tetrahydro-1H-indazole A mixture of the ether from Example 61 (20 mg, 0.051 mmol) and palladium on carbon (5 mg) in methanol (4 mL) was stirred under $H_2$ balloon at room temperature for 4 h. The mixture was filtered and the filtrate was concentrated to yield Example 64 as a 5:1 mixture of two diastereomers (14 mg, 70%). MS found: (M+H)⁺=393.

Examples 65 and 66

2-((R)-1-(4-fluorophenyl)-5,6-dimethyl-4,5-dihydro-1H-indazol-5-yl)-1-(3-methoxyphenyl) ethanol In an analogous procedure to reaction 1i, the homochiral aldehyde from reaction 1h (40 mg, 0.141 mmol) was reacted with 3-methoxyphenylmagnesium bromide to give Examples 65 (15 mg, 27%, isomer A, faster eluent on chiral OD column) and 66 (15 mg, 27%, isomer B, slower eluent). MS found: (M+H)⁺=393.

Examples 67 and 68

2-((R)-1-(4-fluorophenyl)-5,6-dimethyl-4,5-dihydro-1H-indazol-5-yl)-1-(3-methylthiophen-2-yl)ethanol In an analogous procedure to reaction 1i the homochiral aldehyde from reaction 1h (40 mg, 0.141 mmol) was reacted with 3-methyl-2-thienylmagnesium bromide to give Examples 67 (12 mg, 22%, isomer A, faster eluent on chiral AD column) and 68 (14 mg, 26%, isomer B, slower eluent). MS found: (M+H)⁺=383.

Examples 69 and 70

2-((R)-1-(4-fluorophenyl)-5,6-dimethyl-4,5-dihydro-1H-indazol-5-yl)-1-(5-methylthiophen-2-yl)ethanol In an analogous procedure to reaction 1i the homochiral aldehyde from reaction 1h (40 mg, 0.141 mmol) was reacted with 5-methyl-2-thienylmagnesium bromide to give Examples 69 (14 mg, 26%, isomer A, faster eluent on chiral OD column) and 70 (10 mg, 19%, isomer B, slower eluent). MS found: (M+H)⁺=383.

Examples 71 and 72

2-((R)-1-(4-fluorophenyl)-5,6-dimethyl-4,5-dihydro-1H-indazol-5-yl)-1-(thiazol-2-yl)ethanol A 1.6 M hexane solution of butyllithium (0.78 mL, 11 eq) was added to a solution of thiazole (120 mg, 10 eq) in ether (5 ml) at −78° C. After 0.5 h at −78° C., a solution of the homochiral aldehyde from reaction 1h (40 mg, 0.141 mmol) in ether (1 mL) was added. The mixture was stirred at ambient temperature for 0.5 h, quenched with saturated $NH_4Cl$ (2 mL), diluted with EtOAc (60 mL), washed with water (5 mL), brine (5 mL), dried ($MgSO_4$) and concentrated. Silica gel column chromatography (EtOAc-hexane, 30 to 100%) yielded the desired alcohol as a mixture of two diastereomers (14 mg), which was separated by chiral AD column (isocratic, i-PrOH/heptane/Diethylamine, 10/90/0.1) to give Examples 71 (7.0 mg, 13%, isomer A, faster eluent) and 72 (3.5 mg, 6.5%, isomer B, slower eluent). MS found: (M+H)⁺=370.

Examples 73 and 74

1-((R)-1-(4-fluorophenyl)-5,6-dimethyl-4,5-dihydro-1H-indazol-5-yl)but-3-yn-2-ol In an analogous procedure to reaction 1i, the homochiral aldehyde from reaction 1h (40 mg, 0.141 mmol) was reacted with ethynylmagnesium bromide to give Examples 73 (10 mg, 23%, isomer A, faster eluent on chiral OD column) and 74 (6 mg, 13%, isomer B, slower eluent). MS found: (M+H)⁺=311.

Examples 75 and 76

2-((R)-1-(4-fluorophenyl)-5,6-dimethyl-4,5-dihydro-1H-indazol-5-yl)-1-(pyridin-2-yl)ethanol A 2.0 M THF solution of iso-PrMgCl (0.70 mL, 10 eq) was added to a solution of 2-bromopyridine (223 mg, 10 eq) in THF (2 ml) at room temperature. After 2 h, a solution of the homochiral aldehyde from reaction 1h (40 mg, 0.141 mmol) in THF (1 mL) was added. The mixture was stirred at room temperature for 24 h, quenched with saturated $NH_4Cl$ (2 mL), diluted with EtOAc (60 mL), washed with water (5 mL), brine (5 mL), dried ($MgSO_4$) and concentrated. Silica gel column chromatography (EtOAc-hexane, 0 to 50%) yielded the desired alcohol as a mixture of two diastereomers (14 mg), which was separated by chiral OD column (isocratic, i-PrOH/heptane, 20%) to give Examples 75 (6.0 mg, 12%, isomer A, faster eluent) and 76 (5.0 mg, 10%, isomer B, slower eluent). MS found: (M+H)⁺=364.

Example 77

(R)-5-(2-ethoxy-2-(pyridin-2-yl)ethyl)-1-(4-fluorophenyl)-5,6-dimethyl-4,5-dihydro-1H-indazole Using a procedure analogous to Example 35, the diastereomer mixture of the alcohols from Examples 75 and 76 (53 mg, 0.146 mmol) was reacted with iodoethane to give Example 77 as a 1:2 mixture of two diastereomers (20 mg, 35%).
MS found: $(M+H)^+=392$.

Examples 78 and 79

2-(2-((R)-1-(4-fluorophenyl)-5,6-dimethyl-4,5-dihydro-1H-indazol-5-yl)-1-hydroxyethyl) pyridine 1-oxide 3-chloroperoxybenzoic acid (28 mg, 1.5 eq) was added to a solution of the diastereomer mixture of the alcohols from Examples 75 and 76 in chloroform (3 mL) at room temperature. After 3 h, the mixture was quenched with saturated NaHCO$_3$ (1 mL), diluted with EtOAc (60 mL), washed with water (5 mL), brine (5 mL), dried (MgSO$_4$) and concentrated. Reverse phase HPLC purification (MeOH-water, 50 to 100%) yielded the desired N-oxide as a mixture of two diastereomers (5 mg), which was separated by chiral OD column (isocratic, i-PrOH/heptane, 15%) to give Examples 78 (1.3 mg, 3%, isomer A, faster eluent) and 79 (1.5 mg, 4%, isomer B, slower eluent). MS found: $(M+H)^+=380$.

Examples 80 and 81

2-((R)-1-(4-fluorophenyl)-5,6-dimethyl-4,5-dihydro-1H-indazol-5-yl)-1-(pyridin-3-yl)ethanol In an analogous procedure to Examples 75 and 76, the homochiral aldehyde from reaction 1h (40 mg, 0.141 mmol) was reacted with 3-bromopyridine to give Examples 80 (4 mg, 8%, isomer A, faster eluent on chiral AD column) and 81 (6 mg, 12%, isomer B, slower eluent). MS found: $(M+H)^+=364$.

Examples 82 and 83

1-(2,6-dimethylphenyl)-2-((R)-1-(4-fluorophenyl)-5,6-dimethyl-4,5-dihydro-1H-indazol-5-yl)ethanol In an analogous procedure to reaction 1the homochiral aldehyde from reaction 1h (40 mg, 0.141 mmol) was reacted with 2,6-dimethylphenylmagnesium bromide to give Examples 82 (15 mg, 27%, isomer A, faster eluent on chiral OD column) and 83 (15 mg, 27%, isomer B, slower eluent). MS found: $(M+H)^+=391$.

Examples 84 and 85

2-((R)-1-(4-fluorophenyl)-5,6-dimethyl-4,5-dihydro-1H-indazol-5-yl)-1-(2-methylnaphthalen-1-yl)ethanol In an analogous procedure to reaction 1i the homochiral aldehyde from reaction 1h (40 mg, 0.141 mmol) was reacted with 2-methyl-1-naphthylmagnesium bromide to give Examples 84 (15 mg, 25%, isomer A, faster eluent on silica gel column) and 85 (15 mg, 25%, isomer B, slower eluent). MS found: $(M+H)^+=427$.

Examples 86 and 87

2-((R)-1-(4-fluorophenyl)-5,6-dimethyl-4,5-dihydro-1H-indazol-5-yl)-1-(2-methoxynaphthalen-1-yl)ethanol In an analogous procedure to reaction 1i, the homochiral aldehyde from reaction 1h (40 mg, 0.141 mmol) was reacted with 2-methoxy-1-naphthylmagnesium bromide to give Examples 86 (12 mg, 19%, isomer A, faster eluent on chiral OD column) and 87 (12 mg, 19%, isomer B, slower eluent). MS found: $(M+H)^+=443$.

Examples 88 and 89

1-(2,6-dimethoxyphenyl)-2-((R)-1-(4-fluorophenyl)-5,6-dimethyl-4,5-dihydro-1H-indazol-5-yl)ethanol In an analogous procedure to Example 71 and 72, the homochiral aldehyde from reaction 1h (40 mg, 0.141 mmol) was reacted with 2,6-dimethoxy-phenyllithium to give Examples 88 (3 mg, 5%, isomer A, faster eluent on chiral AD column) and 89 (4 mg, 7%, isomer B, slower eluent). MS found: $(M+H)^+=423$.

Examples 90 and 91

1-cyclopentyl-2-((R)-1-(4-fluorophenyl)-5,6-dimethyl-4,5-dihydro-1H-indazol-5-yl) ethanol In an analogous procedure to reaction 1i, the homochiral aldehyde from reaction 1h (40 mg, 0.141 mmol) was reacted with cyclopentylmagnesium bromide to give Examples 90 (13 mg, 26%, isomer A, faster eluent on chiral AD column) and 91 (13 mg, 26%, isomer B, slower eluent). MS found: $(M+H)^+=355$.

Examples 92 and 93

2-((R)-1-(4-fluorophenyl)-5,6-dimethyl-4,5-dihydro-1H-indazol-5-yl)-1-(2-(pyrrolidin-1-ylmethyl)phenyl)ethanol In an analogous procedure to reaction 1i, the homochiral aldehyde from reaction 1h (40 mg, 0.141 mmol) was reacted with (2-(1-pyrrolidinylmethyl) phenyl)magnesium bromide to give Examples 92 (9.0 mg, 14%, isomer A, faster eluent on chiral AD column) and 93 (5.0 mg, 8%, isomer B, slower eluent). MS found: $(M+H)^+=446$.

Examples 94 and 95

2-((R)-1-(4-fluorophenyl)-5,6-dimethyl-4,5-dihydro-1H-indazol-5-yl)-1-(2-(morpholinomethyl) phenyl) ethanol In an analogous procedure to reaction 1i, the homochiral aldehyde from reaction 1h (40 mg, 0.141 mmol) was reacted with (2-(4-morpholinomethyl) phenyl)magnesium bromide to give Examples 94 (14 mg, 22%, isomer A, faster eluent on chiral AD column) and 95 (8 mg, 12%, isomer B, slower eluent). MS found: $(M+H)^+=462$.

Examples 96 and 97

1-(2-chlorophenyl)-2-((R)-1-(4-fluorophenyl)-5,6-dimethyl-4,5-dihydro-1H-indazol-5-yl)ethanol In an analogous procedure to Examples 71 and 72, the homochiral aldehyde from reaction 1h (40 mg, 0.141 mmol) was reacted with 2-chloro-1-bromobenzene to give Examples 96 (3.0 mg, 5%, isomer A, faster eluent on chiral AD column) and 97 (6.0 mg, 11%, isomer B, slower eluent). MS found: $(M+H)^+=397$.

Example 98

(5R)-5-(2-(2-chlorophenyl)-2-ethoxyethyl)-1-(4-fluorophenyl)-5,6-dimethyl-4,5-dihydro-1H-indazole Using a procedure analogous to Example 35, the alcohol from Example 96 (6.0 mg, 0.015 mmol) was reacted with iodoethane to give Example 98 (3.5 mg, 55%). MS found: $(M+H)^+=425$.

Examples 99 and 100

(5R)-5-((1,3-dihydroisobenzofuran-1-yl)methyl)-1-(4-fluorophenyl)-5,6-dimethyl-4,5-dihydro-1H-indazole (99a) In an analogous procedure to reaction 1i, the homochiral aldehyde from reaction 1h (80 mg, 0.281 mmol) was treated with 2-(1,3-dioxan-2-yl) phenylmagnesium bromide to provide the desired alcohols as mixture of two diastereomers (100 mg, 79%). MS found: $(M+H)^+=449$.

(99b) Triethylsilane (0.2 mL) and trifluoroacetic acid (0.2 mL) were added to a solution of the alcohols from reaction 99a (80 mg, 0.241 mmol) in dichloromethane (2 mL) at room temperature. After 1 h at room temperature, the mixture was concentrated and purified by silica gel column chromatography (EtOAc-hexane, 0 to 30%) to provide the desired compound as a mixture of two diastereomers (50 mg), which was separated by chiral AD column (isocratic, i-PrOH/heptane, 15%) to give Examples 99 (30 mg, 37%, isomer A, faster eluent) and 100 (15 mg, 19%, isomer B, slower eluent). MS found: $(M+H)^+=375$.

Examples 101 and 102

2-((R)-1-(4-fluorophenyl)-5,6-dimethyl-4,5-dihydro-1H-indazol-5-yl)-1-(4-methylthiazol-2-yl)ethanol In an analogous procedure to Examples 71 and 72, the homochiral aldehyde from reaction 1h (60 mg, 0.211 mmol) was reacted with 4-methylthiazole to give Examples 101 (38 mg, 47%, isomer A, faster eluent on chiral AD column) and 102 (38 mg, 47%, isomer B, slower eluent). MS found: $(M+H)^+=384$.

Examples 103

2-(1-ethoxy-2-((R)-1-(4-fluorophenyl)-5,6-dimethyl-4,5-dihydro-1H-indazol-5-yl) ethyl)-4-methylthiazole Using a procedure analogous to Example 35, the alcohol from Example 101 (23.0 mg, 0.060 mmol) was reacted with iodoethane to give Example 103 (17.0 mg, 69%). MS found: $(M+H)^+=412$.

Example 104

2-(1-ethoxy-2-((R)-1-(4-fluorophenyl)-5,6-dimethyl-4,5-dihydro-1H-indazol-5-yl) ethyl)-4-methylthiazole Using a procedure analogous to Example 35, the alcohol from Example 102 (23.0 mg, 0.060 mmol) was reacted with iodoethane to give Example 104 (22.0 mg, 89%). MS found: $(M+H)^+=412$.

Examples 105 and 106

1-cyclohexyl-2-((R)-1-(4-fluorophenyl)-5,6-dimethyl-4,5-dihydro-1H-indazol-5-yl) ethanol In an analogous procedure to reaction 1i, the homochiral aldehyde from reaction 1h (60 mg, 0.211 mmol) was reacted with cyclohexylmagnesium bromide to give Examples 105 (23 mg, 30%, isomer A, faster eluent on chiral AD column) and 106 (32 mg, 41%, isomer B, slower eluent). MS found: $(M+H)^+=369$.

Example 107

(5R)-5-(2-cyclohexyl-2-ethoxyethyl)-(-(4-fluorophenyl)-5,6-dimethyl-4,5-dihydro-1H-indazole Using a procedure analogous to Example 35, the alcohol from Example 105 (13.0 mg, 0.033 mmol) was reacted with iodoethane to give Example 107 (4.0 mg, 30%). MS found: $(M+H)^+=397$.

Example 108

(5R)-5-(2-cyclohexyl-2-ethoxyethyl)-1-(4-fluorophenyl)-5,6-dimethyl-4,5-dihydro-1H-indazole Using a procedure analogous to Example 35, the alcohol from Example 106 (18.0 mg, 0.049 mmol) was reacted with iodoethane to give Example 108 (4.0 mg, 20%). MS found: $(M+H)^+=397$.

Example 109

(R)-1-(1-(4-fluorophenyl)-5,6-dimethyl-4,5-dihydro-1H-indazol-5-yl)-2-phenylpentan-2-ol Using a procedure analogous to reaction 1i, the ketone from Example 24 (70.0 mg, 0.194 mmol) was reacted with n-propylmagnesium bromide to give Example 109 as a 3:2 mixture of two diastereomers (30.0 mg, 38%). MS found: $(M+H)^+=405$.

Example 110

(R)-2-(1-(4-fluorophenyl)-5,6-dimethyl-4,5-dihydro-1H-indazol-5-yl)-1-phenylethanamine (110a) A benzene (10 mL) solution of Example 24 (82 mg, 0.228 mmol) and O-benzylhydroxylamine (500 μL, 8 eq) was heated to reflux for 22 h, concentrated and purified by flash column chromatography (0-20% EtOAc-hexanes) to give the desired oxime (80 mg, 75%). MS found: $(M+H)^+=466$.

(110b) To a formic acid (16 mL) solution of the oxime (75 mg, 0.161 mmol) from reaction 110a was added zinc powder (1 g, 96 eq). The resulting suspension was heated to reflux for 1 h, cooled to room temperature, diluted with EtOAc and filtered through celite. The filtrate was concentrated and purified by reverse-phase preparative HPLC (50-90% solvent B gradient) to give Example 110 (73.9 mg, 97%). MS found: (M+H)$^+$=362.

Example 111

(R)-N-(2-(1-(4-fluorophenyl)-5,6-dimethyl-4,5-dihydro-1H-indazol-5-yl)-1-phenylethyl) acetamide A CH$_2$Cl$_2$ (0.6 mL) solution of Example 110 (15 mg, 0.032 mmol), acetic anhydride (4.5 µL, 1.5 eq) and TEA (44 µL, 10 eq) was stirred at room temperature for 1 h. The crude material was purified by flash column chromatography (40-100% EtOAc-hexanes) to give Example 111 (11.7 mg, 92%). MS found: (M+H)$^+$=404.

Example 112

(R)-N,N-diethyl-2-(1-(4-fluorophenyl)-5,6-dimethyl-4,5-dihydro-1H-indazol-5-yl)-1-phenylethanamine A ClCH$_2$CH$_2$Cl (0.6 mL) solution of Example 110 (22.6 mg, 0.048 mmol), acetal aldehyde (32.5 mg, 15 eq) and NaBH(OAc)$_3$ (21.9 mg, 2.2 eq) was stirred at room temperature for 22 h. The crude material was purified by reverse-phase preparative HPLC (50-90% solvent B gradient) to give Example 112 (3.2 mg, 13%) as a 1:1 mixture of two diastereomers. MS found: (M+H)$^+$=418.

Examples 113 and 114

N-ethyl-2-((R)-1-(4-fluorophenyl)-5,6-dimethyl-4,5-dihydro-1H-indazol-5-yl)-1-phenylethanamine In the preparation of Example 112, Example 113 was obtained by preparative chiral HPLC (Chiralpak AD column, 20% iPrOH-heptane) as the fast diastereomer (2.3 mg, 12%) and Example 114 was obtained as the slow diastereomer (1.3 mg, 7%). MS found: (M+H)$^+$=390.

Example 115

2-((5R)-1-(4-fluorophenyl)-5,6-dimethyl-4,5,6,7-tetrahydro-1H-indazol-5-yl)-1-phenylethanol A MeOH (1 mL) solution of Example 1 (100 mg, 0.276 mmol) and palladium on carbon (24 mg) was hydrogenated using a hydrogen balloon for 17 h at room temperature. The mixture was filtered, concentrated and purified by preparative chiral HPLC (Chiralpak AD column, 20% iPrOH-heptane) to give the fast eluting diastereomer as Example 115 (18.6 mg, 19%) and a slow eluting diastereomer (54.4 mg, 54%). MS found: (M+H)$^+$=365.

Example 116

(5R)-5-(2-ethoxy-2-phenylethyl)-1-(4-fluorophenyl)-5,6-dimethyl-4,5,6,7-tetrahydro-1H-indazole In an analogous procedure to the synthesis of Examples 35, Example 115 (8 mg, 0.022 mmol) was converted to Example 116 (4 mg, 47%). MS found: (M+H)$^+$=393.

Examples 117 and 118

2-(1-(4-fluorophenyl)-5-methyl-4,5,6,7-tetrahydro-1H-indazol-5-yl)-1-phenylethanol (117a) Sodium (2.76 g, 1.2 eq) and ethanol (4 mL) were added to ethyl 4-oxocyclohexanecarboxylate (17.02 g, 100 mmol) in ethyl ether (500 mL) at room temperature. After 20 h, water (200 mL) and 1 N HCl (200 mL) were added. The two layers were separated. The aqueous phase was extracted with ethyl ether (2×100 mL). The combined ether phase was dried (MgSO$_4$) and concentrated to give a yellow liquid. The crude ketoaldehyde was taken to next step without purification.

(117b) Sodium acetate (9.02 g, 1.1 eq) was added to a solution of the crude ketoaldehyde from reaction 117a (assumed 100 mmol) and 4-fluorophenylhydrazine hydrochloride (17.89 g, 1.1 eq) in acetic acid (200 mL) at room temperature. After 4 h at room temperature, the mixture was concentrated. The residue was carefully quenched with saturated NaHCO$_3$ (400 mL) and extracted with EtOAc-hexane (1:1, 3×200 mL). The combined extracts were washed with water (20 mL), brine (20 mL), dried (MgSO$_4$) and concentrated. Silica gel chromatography (EtOAc-hexane, 0 to 50%,+10% CH$_2$Cl$_2$) yielded the desired ethyl 1-(4-fluorophenyl)-4,5,6,7-tetrahydro-1H-indazole-5-carboxylate (7.37 g, 26% for 2 steps) and the undesired ethyl 2-(4-fluorophenyl)-4,5,6,7-tetrahydro-2H-indazole-5-carboxylate (4.94 g, 17% for 2 steps). MS found: (M+H)$^+$=289.

(117c) A 2 M solution of LDA (6.98 mL, 1.5 eq, from Aldrich) was added to the desired product from reaction 117b (2.68 g, 9.30 mmol) in THF (100 mL) at 0 °o. After 1 h at 0 °o, iodomethane (1.74 mL, 3 eq) was added. After an additional hour at 0 °o, saturated NH$_4$Cl (100 mL) was added. THF was evaporated in vacuo. The aqueous residue was extracted with EtOAc (3×100 mL). The extracts were washed with brine (10 mL), dried (MgSO$_4$) and concentrated. Silica gel chromatography (EtOAc-hexane, 5 to 25%) gave the desired methylated product (1.139 g, 41%). MS found: (M+H)$^+$=303.

(117d) A 1.5 M toluene solution of DIBAL (4.46 mL, 1.8 eq) was added over 15 min to a solution of the ester from reaction 117c (1.124 g, 3.72 mmol) in CH$_2$Cl$_2$ (50 mL) at −78° C. After 0.5 h at −78° C., the cold bath was removed and the mixture was immediately quenched with saturated Rochelle salt (100 mL). The mixture was stirred vigorously for 2 h and the two phases were separated. The aqueous phase was extracted with CH$_2$Cl$_2$ (2×50 mL). The combined organic phase was dried (MgSO$_4$) and concentrated. Silica gel chromatography (EtOAc-hexane, 10 to 50%) gave the desired aldehyde (356.6 mg, 37%) and over-reduced alcohol (485.2 mg, 50%). MS found: (M+H)$^+$=259.

(117e-g) Following conditions for reactions 1g-i, the aldehyde from reaction 117d was homologated and reacted with phenylmagnesium bromide. Silica gel chromatography (EtOAc-hexane, 10 to 30%) gave Example 117 as the fast eluting isomer (178 mg, 37% for 3 steps) and Example 118 as the slow eluting isomer (167.2 mg, 37% for 3 steps). MS found: (M+H)$^+$=335 1.

Examples 119 and 120

5-(2-ethoxy-2-phenylethyl)-1-(4-fluorophenyl)-5-methyl-4,5,6,7-tetrahydro-1H-indazole Using a procedure analogous to Example 35, the alcohols from Examples 117 and 118 were reacted with iodoethane to give Examples 119 and 120, respectively. MS found: (M+H)$^+$= 379.

Examples 121 and 122

2-(1-(4-fluorophenyl)-5-methyl-6-(trifluoromethyl)-4,5-dihydro-1H-indazol-5-yl)-1-phenylethanol (121a) 60% sodium hydride in mineral oil (105 mg, 0.05 eq) was added the solution of ethyl 4,4,4-trifluoro-2-methyl-3-oxobutanoate (10.39 g, 52.5 mmol) in benzene (50 mL) at room temperature. After 10 min, methyl vinyl ketone (4.73 mL, 1.1 eq) was added. The mixture was stirred for 4 h and filtered through a silica gel pad. The pad was rinsed with EtOAc until free of product. The filtrate was concentrated to give a colorless liquid (14.4 g, 96%). MS found: $(M+H)^+=269$.

(121b) p-Toluenesulfonic acid monohydrate (999 mg, 0.1 eq) was added to the crude material from reaction 121a (assumed 52.5 mmol) in benzene (200 mL). The mixture was heated to reflux for 2 h while a Dean-Stark trap was used to azeotropically remove water. Additional TsOH (1.98 g, 0.2 eq) was added. After 15 h at reflux, another batch of TsOH (4.95 g, 0.5 eq) was added. After another 5 h of reflux, the mixture was filtered through a silica gel pad. The pad was rinsed with EtOAc-hexane (1:1) until free of product. The filtrate was concentrated to give a mixture of the desired cyclohexenone product and unreacted starting material. Silica gel chromatography (EtOAc-hexane, 5 to 15%) yielded the desired cyclohexenone (4.69 g, 36% for 2 steps). MS found: $(M+H)^+=251$.

(121c) The cyclohexenone from reaction 121b (3.94 g, 15.8 mmol) in N,N-dimethylformamide dimethyl acetal (50 mL) was stirred at 110° C. for 15 h, and concentrated to give a brown solid. The crude enamine was taken to next step without purification. MS found: $(M+H)^+=306$.

(121d-h) Following conditions for reactions 1e-i, the enamine from reaction 121c was reacted with 4-fluorophenylhydrazine hydrochloride, reduced to aldehyde, homologated and reacted with phenylmagnesium bromide. Reverse phase HPLC (75 to 100% solvent B gradient) gave Example 121 as the fast eluting isomer and Example 122 as the slow eluting isomer. MS found: $(M+H)^+=417$.

Example 123

5-(2-ethoxy-2-phenylethyl)-1-(4-fluorophenyl)-5-methyl-6-(trifluoromethyl)-4,5-dihydro-1H-indazole Using a procedure analogous to Example 35, the alcohol from Example 122 was reacted with iodoethane to give Example 123. MS found: $(M+H)^+=445$.

Example 124

((5R)-5-(2-ethoxy-2-phenylethyl)-1-(4-fluorophenyl)-5-methyl-4,5-dihydro-1H-indazol-6-yl)methanol (124a) Selenium dioxide (62 mg, 2.0 eq) was added to a solution of the ether from Example 36 (110 mg, 0.282 mmol) in 1,4-dioxane (4 mL) at room temperature. The mixture was heated to reflux for 3 h, cooled to room temperature and diluted with EtOAc (100 mL), washed with water (10 mL), brine (10 mL), dried (MgSO$_4$) and concentrated. Silica gel chromatography (EtOAc-hexane, 0 to 50%) yielded the desired aldehyde (100 mg, 88%). MS found: $(M+H)^+=405$.

(124b) Sodium borohydride (14 mg, 3.0 eq) was added to a solution of the aldehyde from reaction 124a (50 mg, 0.124 mmol) in MeOH (1 mL). After 0.5 h at room temperature, the mixture was quenched with water (1 mL), diluted with EtOAc (60 mL), washed with water (5 mL), brine (5 mL), dried (MgSO$_4$) and concentrated. Silica gel chromatography (EtOAc-hexane, 0 to 50%) yielded Example 124 (32 mg, 64%). MS found: $(M+H)^+=407$.

Example 125

(5R)-5-(2-ethoxy-2-phenylethyl)-1-(4-fluorophenyl)-6-(methoxymethyl)-5-methyl-4,5-dihydro-1H-indazole Using a procedure analogous to Example 35, the alcohol from Example 124 (15.0 mg, 0.037 mmol) was converted to Example 125 (5.0 mg, 32%). MS found: $(M+H)^+=421$.

Example 126

((5R)-5-(2-ethoxy-2-phenylethyl)-1-(4-fluorophenyl)-5-methyl-4,5-dihydro-1H-indazol-6-yl)methyl pivalate Triethylamine (37.5 mg, 5.0 eq) and pivaloyl chloride (17.9 mg, 2.0 eq) were added to a solution of the alcohol from Example 124 (30 mg, 0.074 mmol) in CH$_2$Cl$_2$ (2 mL). After 24 h at room temperature, the mixture was quenched with water (1 mL), diluted with EtOAc (60 mL), washed with water (5 mL), brine (5 mL), dried (MgSO$_4$) and concentrated. Silica gel chromatography (EtOAc-hexane, 0 to 50%) yielded Example 126 (30 mg, 82%). MS found: $(M+H)^+=491$.

Example 127

(5R)-5-(2-ethoxy-2-phenylethyl)-6-ethyl-1-(4-fluorophenyl)-5-methyl-4,5-dihydro-1H-indazole A 3.0 M solution of methylmagnesium bromide (0.08 mL, 6.0 eq) and copper(I) chloride (2.0 mg, 0.6 eq) were added to a solution of the ester from Example 126 (20 mg, 0.041 mmol) in diethyl ether (2 mL) at −20° C. After 0.5 h at 0° C., the mixture was quenched with water (1 mL), diluted with EtOAc (60 mL), washed with water (5 mL), brine (5 mL), dried (MgSO$_4$) and concentrated. Silica gel chromatography (EtOAc-hexane, 0 to 50%) yielded Example 127 (10 mg, 60%). MS found: $(M+H)^+=405$.

Example 128

(5R)-6-(difluoromethyl)-5-(2-ethoxy-2-phenylethyl)-1-(4-fluorophenyl)-5-methyl-4,5-dihydro-1H-indazole A solution of DAST (12.0 mg, 1.5 eq) in CH$_2$Cl$_2$ (0.5 mL) was added to a solution of the aldehyde from reaction 124(a) (20 mg, 0.05 mmol) in CH$_2$Cl$_2$ (1 mL) at −78° C. After stirring at room temperature for 24 h, the mixture was quenched with water (1 mL), diluted with EtOAc (60 mL), washed with water (5 mL), brine (5 mL), dried (MgSO$_4$) and concentrated. Silica gel chromatography (EtOAc-hexane, 0 to 20%) yielded Example 128 (3.0 mg, 14%). MS found: $(M+H)^+=427$.

Example 129

2-(1-(4-fluorophenyl)-5-methyl-4,5-dihydro-1H-indazol-5-yl)-1-phenylethanol (129a) 60% sodium hydride in mineral oil (150 mg, 0.05 eq) was added to a solution of 2-formylpropionic acid ethyl ester (9.75 g, 75.0 mmol) and methyl vinyl ketone (5.76 g, 1.1 eq) in benzene (150 mL) at room temperature. After 24 h at room temperature, the mixture was quenched with acetic acid (0.4 mL) and filtered through a silica gel pad. The pad was washed with diethyl ether until free of product. The filtrate was concentrated to yield the desired compound (14.4 g, 96%).

(129b) Acetic acid (4.11 g, 0.95 eq) and piperidine (4.90 g, 0.8 eq) were added to a solution of the compound from reaction 129a (14.4 g, 72.0 mmol) in THF (100 mL) at room temperature. The mixture was heated to reflux for 24 h, cooled to room temperature and filtered through a silica gel pad. The pad was washed with diethyl ether until free of product. The filtrate was concentrated and purified by silica gel chromatography (EtOAc-hexane, 0 to 50%) to yield the desired cyclic ketone (9.25 g, 71%). MS found: $(M+H)^+=183$.

(129c-g) Using procedures analogous to reactions 1d-h the cyclic ketone from reaction 129b (11.4 g, 62.6 mmol) was converted to the desired aldehyde as a racemic material (5.87 g, 35% for 5 steps). MS found: $(M+H)^+=271$.

(129h) Using a procedure analogous to reaction 1i, the aldehyde from reaction 129g (200 mg, 0.741 mmol) was converted to Example 129 as a 1:1:1:1 mixture of four isomers (250 mg, 96%). MS found: $(M+H)^+=349$.

Example 130

2-(1-(4-fluorophenyl)-5-methyl-4,5-dihydro-1H-indazol-5-yl)-1-phenylethanol (130a) The racemic aldehyde from reaction 129g (2.3 g) was separated by chiral AS column ($CO_2$/IPA with 0.1% TFA) to provide enantiomer A (faster eluent, 650 mg, 28%) and enantiomer B (slower eluent, 650 mg, 28%). MS found: $(M+H)^+=271$.

(130b) Using a procedure analogous to reaction 1i, enantiomer B of the aldehyde from reaction 130a (500 mg, 1.85 mmol) was converted to Example 130 as a 1:1 mixture of two diastereomers (610 mg, 95%). MS found: $(M+H)^+=349$.

Example 131

2-(1-(4-fluorophenyl)-5-methyl-4,5-dihydro-1H-indazol-5-yl)-1-phenylethanol

Using a procedure analogous to reaction 1i, enantiomer A of the aldehyde from procedure 130a (500 mg, 1.85 mmol) was converted to Example 131 as a 1:1 mixture of two diastereomers (610 mg, 95%). MS found: $(M+H)^+=349$.

Example 132

5-(2-ethoxy-2-phenylethyl)-1-(4-fluorophenyl)-5-methyl-4,5-dihydro-1H-indazole Using a procedure analogous to Example 35, the alcohol from Example 129 (230 mg, 0.663 mmol) was converted to Example 132 as a 1:1:1:1 mixture of four isomers (160 mg, 64%). MS found: $(M+H)^+=377$.

Example 133

5-(2-ethoxy-2-phenylethyl)-1-(4-fluorophenyl)-5-methyl-4,5-dihydro-1H-indazole (133a) The diastereomer mixture of the alcohol from Example 130 (600 mg) was separated by chiral AD column (isocratic, i-PrOH/heptane, 20%) to give diastereomer A (290 mg, 48%, faster eluent) and diastereomer B (290 mg, 48%, slower eluent). MS found: $(M+H)^+=349$.

(133b) Using a procedure analogous to Example 35, diastereomer A of the alcohol from reaction 133a (270 mg, 0.776 mmol) was converted to Example 133 (200 mg, 69%). MS found: $(M+H)^+=377$.

Example 134

5-(2-ethoxy-2-phenylethyl)-1-(4-fluorophenyl)-5-methyl-4,5-dihydro-1H-indazole Using a procedure analogous to Example 35, diastereomer B of the alcohol from reaction 133a (270 mg, 0.776 mmol) was converted to Example 134 (150 mg, 51%). MS found: $(M+H)^+=377$.

Example 135

5-(2-ethoxy-2-phenylethyl)-1-(4-fluorophenyl)-5-methyl-4,5,6,7-tetrahydro-1H-indazol-6-ol (135a) 3-chloroperoxybezoic acid (24 mg, 2.0 eq) was added to a solution of the compound from Example 134 (20 mg, 0.053 mmol) in $CH_2Cl_2$ (2 mL) at 0° C. After 2 h to room temperature, the mixture was carefully quenched with saturated $NaHCO_3$ (1 mL) and diluted with EtOAc (80 mL), washed with water (5 mL), brine (5 mL), dried ($MgSO_4$) and concentrated. Silica gel chromatography (EtOAc-hexane, 0 to 30%) yielded the desired epoxide (16.0 mg, 77%). MS found: $(M+H)^+=393$.

(135b) A 1.0 M THF solution of lithium aluminum hydride (0.06 mL, 3.0 eq) was added to a solution of the epoxide from reaction 135a (8.0 mg, 0.020 mmol) in THF (1 mL) at 0° C. After stirring at room temperature for 3 h, the mixture was carefully quenched with EtOAc (60 mL), washed with water (5 mL), brine (5 mL), dried ($MgSO_4$) and concentrated. Silica gel chromatography (EtOAc-hexane, 0 to 40%) yielded Example 135 (3.0 mg, 38%, fast eluting isomer) and a slow eluting isomer (3.0 mg, 38%). MS found: $(M+H)^+=395$.

Example 136

5-(2-ethoxy-2-phenylethyl)-1-(4-fluorophenyl)-5-methyl-4,5,6,7-tetrahydro-1H-indazol-6-ol Using similar procedures to reaction 135a-b, the compound from Example 133 (40 mg, 0.106 mmol) was converted to Example 136 as a 1:1 mixture of two isomers (26 mg, 62% for 2 steps). MS found: $(M+H)^+=395$.

Example 137

(5R)-5-(2-ethoxy-2-phenylethyl)-1-(4-fluorophenyl)-6-methoxy-5-methyl-4,5-dihydro-1H-indazole (137a) Dess-Martin periodinane (151 mg, 2.0 eq) was added to a solution of the alcohols from Example 136 (70.0 mg, 0.178 mmol) in $CH_2Cl_2$ (5 mL) at room temperature.

After 3 h at room temperature, the mixture was diluted with EtOAc (80 mL), washed with water (5 mL), brine (5 mL), dried (MgSO$_4$) and concentrated. Silica gel chromatography (EtOAc-hexane, 0 to 30%) yielded the desired ketone (60 mg, 86%). MS found: (M+H)$^+$=393.

(137b) sodium hydride in mineral oil (3.0 mg, 3.0 eq) was added to a solution of the ketone from reaction 137a (10 mg, 0.025 mmol) in DMF (1 mL) at room temperature. The mixture was stirred for 10 min, then cooled to –10° C. Dimethyl sulfate (9.0 mg, 3.0 eq) in DMF (0.2 mL) was added. The resultant mixture was stirred at 0° C. for 1 h, quenched with saturated NaHCO$_3$ (1 mL), diluted with EtOAc (60 mL), washed with water (5 mL), brine (5 mL), dried (MgSO$_4$) and concentrated. Silica gel chromatography (EtOAc-hexane, 0 to 30%) yielded Example 137 (5.0 mg, 49%). MS found: (M+H)$^+$=407.

Example 138

2-(1-(4-fluorophenyl)-5-(hydroxymethyl)-4,5,6,7-tetrahydro-1H-indazol-5-yl)-1-phenylethanol (138a) A 2 M solution of LDA (6.00 mL, 1.2 eq, from Aldrich) was added dropwise to the desired product from reaction 117b (2.88 g, 10.0 mmol) in THF (100 mL) at –78 °o. After 1.5 h at –78 °o, allyl bromide (2.54 mL, 3 eq) was added. The mixture was stirred at –78 °o for 1.5 h and at ambient temperature for 30 min. After addition of saturated NH$_4$Cl (100 mL), THF was evaporated in vacuo. The aqueous residue was extracted with EtOAc (3×100 mL). The extracts were dried (MgSO$_4$) and concentrated. Silica gel chromatography (EtOAc-hexane, 10 to 25%) gave the desired product (2.28 g, 70%) as a colorless liquid. MS found: (M+H)$^+$=329.

(138b) Ozone was bubbled through a solution of the material from reaction 138a (2.20 g, 6.70 mmol) in MeOH (50 mL) and CH$_2$Cl$_2$ (50 mL) at –78 °o until the solution turned yellow. Polystyrene-supported PPh$_3$ (10.05 g, 1 mmol/g) was added and the mixture was stirred at ambient temperature for 20 h. The mixture was concentrated and filtered through a celite pad. The celite pad was rinsed with EtOAc. The filtrate was concentrated and purified by silica gel chromatography (EtOAc-hexane, 20 to 50%) to give the desired aldehyde (1.24 g, 56%). MS found: (M+MeOH+H)$^+$=363.

(138c) A 1.0 M THF solution of phenylmagnesium bromide (843 mL, 1.1 eq)) was added dropwise to the aldehyde from reaction 138b (252.8 mg, 0.766 mmol) in THF (5 mL) at 0 °o. After 1 h, the mixture was quenched with saturated NH$_4$Cl (20 mL). THF was evaporated in vacuo. The aqueous residue was extracted with diluted with EtOAc (2×20 mL). The extracts were dried (MgSO$_4$) and concentrated. Silica gel chromatography (EtOAc-hexane, 20 to 40%) followed by reverse phase HPLC (60 to 90% solvent B gradient) separated two spirolactone isomers: isomer A (47.8 mg, 17%, fast eluting isomer from RP HPLC), isomer B (63.1 mg, 23%, slow eluting isomer). MS found: (M+H)$^+$=363.

(138d) A 1.5 M toluene solution of DIBAL (0.130 mL, 1.5 eq) was added to isomer B from reaction 138c (47.1 mg, 0.130 mmol) in CH$_2$Cl$_2$ (5 mL) at –78° C. After 0.5 h at –78° C., additional DIBAL (0.130 mL, 1.5 eq) was added. After another 30 min, the cold bath was removed and the mixture was immediately quenched with saturated Rochelle salt (20 mL). The mixture was stirred overnight and extracted with CH$_2$Cl$_2$ (3×10 mL). The combined extracts were dried (MgSO$_4$) and concentrated. Silica gel chromatography (EtOAc-hexane, 20 to 40%) gave the desired lactol (41.6 mg, 88%). MS found: (M+H)$^+$=365.

(138e) Lithium aluminum hydride (100 mg) was added to the lactol from reaction 138d (19.1 mg, 0.0525 mmol) in THF. After 1 h at room temperature, the mixture was quenched with saturated NH$_4$Cl (15 mL) and extracted with EtOAc (3×10 mL). The combined extracts were dried (MgSO$_4$) and concentrated. Silica gel chromatography (EtOAc-hexane, 30 to 80%) gave Example 138 (14.0 mg, 73%). MS found: (M+H)$^+$= 367.

Example 139

(R)-N-(2-(1-(4-fluorophenyl)-5,6-dimethyl-4,5-dihydro-1H-indazol-5-yl)ethyl)-1,3,4-thiadiazol-2-amine Titanium(IV) isopropoxide (32.8 mg, 1.1 eq) and sodium triacetoxyborohydride (67 mg, 3.0 eq) were added to a mixture of the homochiral aldehyde from reaction 1h (30 mg, 0.105 mmol) and 2-amino-1,3,4-thiadiazole (21 mg, 2.0 eq) in 1,2-dichloroethane (2 mL) at room temperature. After 2 h at 80° C., the mixture was cooled to room temperature and saturated NaHCO$_3$ (2 mL) and EtOAc (60 mL) were added. The mixture was washed with water (5 mL), brine (5 mL), dried (MgSO$_4$) and concentrated. Silica gel chromatography (EtOAc-hexane, 80 to 100%) yielded Example 139 (18.0 mg, 46%). MS found: (M+H)$^+$=370.

Example 140

(R)-5-(2-(benzyloxy)ethyl)-1-(4-fluorophenyl)-5,6-dimethyl-4,5-dihydro-1H-indazole Using a procedure analogous to Example 35, the alcohol from Example 23 (20 mg, 0.070 mmol) was reacted with benzyl bromide to give Example 140 (10.0 mg, 38%). MS found: (M+H)$^+$=377.

Example 141

(R)-N-benzyl-2-(1-(4-fluorophenyl)-5,6-dimethyl-4,5-dihydro-1-indazol-5-yl) ethanamine Sodium triacetoxyborohydride (45 mg, 3.0 eq) was added to a mixture of the homochiral aldehyde from reaction 1h (20 mg, 0.704 mmol) and benzylamine (16 mg, 2.0 eq) in 1,2-dichloroethane (2 mL). After 24 h at room temperature, the mixture was quenched with saturated NaHCO$_3$ (2 mL). Following addition of EtOAc (60 mL), the mixture was washed with water (5 mL), brine (5 mL), dried (MgSO$_4$) and concentrated. Reverse phase HPLC purification (methanol-water, 20 to 100%) yielded Example 141 as a TFA salt (9.0 mg, 27%). MS found: (M+H)$^+$=376.

Example 142

(S)-1-(4-fluorophenyl)-5,6-dimethyl-5-(2-phenylallyl)-4,5-dihydro-1H-indazole

To a toluene (1.5 mL) solution of Example 24 (40.5 mg, 0.11 mmol), THF (50 μL) and pyridine (500 μL) was added Tebbe's reagent (0.5 M toluene solution, 0.35 mL, 1.6 eq) at –40° C. The mixture was allowed to warm to room temperature in 2 h then quenched by adding 1 N NaOH at –10° C. The mixture was diluted with ether (10 mL), EtOAc (10 mL) and water (10 mL) then filtered. The organic phase of the filtrate was washed with brine, dried (MgSO$_4$) and concentrated. The residue was purified by silica gel chromatography (0-20% EtOAc-hexanes) to give Example 142 (16.8 mg, 42%). MS found: (M+H)$^+$=359.

Example 143

(R,E)-1-(4-fluorophenyl)-5,6-dimethyl-5-(2-(naphthalen-1-yl)vinyl)-4,5-dihydro-1H-indazole p-Toluenesulfonic acid monohydrate (2 mg) was added to a solution of the alcohol mixture from Examples 11 and 12 (10 mg, 0.0243 mmol) in benzene (5 mL) at room temperature. After 1 h at reflux, the mixture was cooled to room temperature and concentrated. Silica gel chromatography (EtOAc-hexane, 0 to 30%) yielded Example 143 (8.0 mg, 84%). MS found: $(M+H)^+$=395.

Example 144

(R)-((S)-1-(4-fluorophenyl)-5,6-dimethyl-4,5-dihydro-1H-indazol-5-yl) (phenyl)methanol (144a) Methyl iodide (6.86 mL, 1.1 eq) and $K_2CO_3$ (17.97 g, 1.3 eq) were added to an acetone (400 mL) solution of tert-butyl 3-oxobutanoate (15.82 g, 100 mmol) at room temperature. After 15 h, the mixture was filtered and the filtrate was concentrated. The residue was dissolved in ethyl acetate (300 mL), washed with water (30 mL) and brine (300 mL), dried ($MgSO_4$) and concentrated. The crude residue was purified by silica gel chromatography (5-10% EtOAc-hexanes) to give tert-butyl 2-methyl-3-oxobutanoate as a colorless oil (9.56 g, 56%). MS found: $(M+Na)^+$=195.

(144b) A benzene (100 mL) suspension of (S)—BINAP (4.58 g, 1.02 eq) was added to a benzene (100 mL) solution of bis(acetonitrile)dichloropalladium(II) (1.86 g, 7.2 mmol) at room temperature. The mixture was stirred for 2 h. The yellow solid was collected by filtration to give $PdCl_2[(S)-$BINAP] (5.78 g, 100%).

(144c) Silver triflate (3.68 g, 2 eq) was added to a water (1 mL) and acetone (200 mL) solution of $PdCl_2[(S)-$BINAP] (5.72 g, 7.15 mmol) from 144b at room temperature. The mixture was stirred for 5 h then filtered through celite. The filtrate was concentrated. The residue was dissolved in $CH_2Cl_2$ (20 mL) and ether (20 mL). A yellow solid was formed after the solution was stored overnight. The solid was collected by filtration to give the active catalyst $[Pd((S)-$BINAP)$(H_2O)_2]^{2+}(OTf)_2^-$ (6.84 g, 90%).

(144d) The Pd catalyst (2.91 g, 0.1 eq) from reaction 144c was added to a THF (10 mL) solution of tert-butyl 2-methyl-3-oxobutanoate (4.71 g, 27.4 mmol) from 144a at room temperature. The solution was cooled to 0° C. and methyl vinyl ketone (6.74 mL, 3 eq) was added dropwise. The mixture was stirred at 0° C. for 36 h and allowed to slowly warm to room temperature overnight. The resultant solution was filtered through a silica gel pad to remove the catalyst. The filter cake was rinsed with 30% EtOAc-hexanes. The filtrate was concentrated and purified by silica gel chromatography (5-25% EtOAc-hexanes) to give the Michael adduct (4.89 g, 74%) as a colorless oil.

(144e) To a THF (25 mL) solution of the Michael adduct (5.58 g, 23.1 mmol) from reaction 144d was added piperidine (1.83 mL, 0.8 eq) and HOAc (1.26 mL, 0.95 eq). The resultant solution was heated to reflux for 20 h. The mixture was filtered through a silica gel pad and the filter cake was rinsed with 30% EtOAc-hexanes. The filtrate was concentrated and purified by silica gel chromatography (5-15% EtOAc-hexanes) to give the desired cyclohexenone (4.30 g, 83%) as a colorless oil. Analytical chiral HPLC (Chiralpak AS column, 5% EtOH-5% MeOH-90% heptane) determined the optical purity as 87-88% ee. MS found: $(M+H)^+$=225.

(144f) To a ether (100 mL) solution of the cyclohexenone (5.58 g, 23.1 mmol) from 144e and ethyl formate (2.07 g, 1.6 eq) was added sodium (483 mg, 1.2 eq) and ethanol (0.7 mL). The mixture was stirred at room temperature for 18 h, quenched with water (200 mL) and acidified to pH 2-3 with 1 N HCl. The mixture was extracted with EtOAc (3×50 mL). The extracts were washed with brine, dried ($MgSO_4$) and concentrated to give the desired ketoaldehyde (4.71 g) as a red oil. MS found: $(M+H)^+$=253.

(144g) To an acetic acid (50 mL) solution of the ketoaldehyde (4.71 g) from reaction 144f was added 4-fluorophenylhydrazine HCl salt (3.13 g, 1.1 eq) and sodium acetate (1.58 g, 1.1 eq). The exothermic mixture was stirred at room temperature for 2 h. The acetic acid was evaporated in vacuo. The residue was treated with saturated $NaHCO_3$ (100 mL) and extracted with EtOAc (3×50 mL). The extracts were washed with brine, dried ($MgSO_4$), concentrated and purified by silica gel chromatography (3-15% EtOAc-hexanes) to give the dihydroindazole tert-butyl ester (5.75 g, 96% for 2 steps) as an orange viscous oil. MS found: $(M+H)^+$=343.

(144h) To a THF (100 mL) solution of the ester (8.28 g, 24.18 mmol) from reaction 144g was added $LiAlH_4$ (3.02 g, 3.3 eq) at 0° C. under $N_2$. The mixture was allowed to slowly warm to room temperature and stirred for 5 h. The reaction was quenched by carefully adding 1 N NaOH (10 mL) dropwise and diluted with THF (100 mL) and stirred overnight until all the aluminum salt precipitated out. The resultant mixture was filtered through a celite pad and the filter cake was rinsed with 50% EtOAc-$CH_2Cl_2$. The combined filtrate was concentrated, dissolved in EtOAc (150 mL), washed with water (10 mL) and brine (10 mL), dried ($MgSO_4$) and concentrated. Silica gel chromatography (0-60% EtOAc-hexanes) followed by crystallization in ether gave the desired dihydroindazole alcohol (4.39 g, 67%) as white needles. Analytical chiral HPLC (Chiralcel OJ column, 10% isopropyl alcohol-90% heptane) determined the optical purity as >99% ee. MS found: $(M+H)^+$=273.

(144i) To a $CH_2Cl_2$ (15 mL) solution of the dihydroindazole alcohol (0.39 g, 1.44 mmol) from reaction 144h was added Dess-Martin periodinane (674 mg, 1.1 eq) at room temperature. The mixture was stirred for 1 h then quenched with saturated $NaHCO_3$ (10 mL) and saturated $NaHSO_3$ (10 mL). The resultant mixture was stirred for 2 h until it became a clear 2-layer solution. The $CH_2Cl_2$ layer was separated and washed with saturated $NaHCO_3$ (10 mL) and brine (10 mL), dried ($MgSO_4$) and concentrated. Silica gel chromatography (0-30% EtOAc-hexanes) gave the desired aldehyde (0.35 g, 90%) as a white solid. MS found: $(M+Na)^+$=303.

(144j) Using a procedure analogous to reaction 1i, the aldehyde (17.6 mg, 0.065 mmol) from 144i was reacted with phenylmagnesium bromide (5.5 eq) to give Example 144 (15.2 mg, 67%). MS found: $(M+H)^+$=349.

Example 145

(S)-1-(1-(4-fluorophenyl)-5,6-dimethyl-4,5-dihydro-1H-indazol-5-yl)-2-phenylethanol Using a procedure analogous to reaction 1i, the aldehyde (15.2 mg, 0.056 mmol) from reaction 144i was reacted with benzylmagnesium bromide (5.5 eq) to give Example 145 (14.8 mg, 73%). MS found: $(M+H)^+$=363.

Examples 146 and 147

(R)-1-((S)-1-(4-fluorophenyl)-5,6-dimethyl-4,5-dihydro-1H-indazol-5-yl)-3-phenylpropan-1-ol Using a procedure analogous to reaction 1, the aldehyde (43 mg, 0.159 mmol) from reaction 144i was reacted with phenethylmagnesium chloride (2 eq) to give a 2:1 mixture of the alcohols. The mixture was separated by preparative chiral HPLC (Chiralpak AD column, 10% iPrOH-Heptane) to give the fast eluting isomer as Example 146 (10.7 mg, 18%) and slow eluting isomer as Example 147 (21.8 mg, 36%). MS found: $(M+H)^+=377$.

Example 148

(S)-1-(4-fluorophenyl)-5-((R)-1-methoxy-3-phenylpropyl)-5,6-dimethyl-4,5-dihydro-1H-indazole In an analogous procedure to the synthesis of Examples 35, Example 146 (8.5 mg, 0.023 mmol) was converted to Example 148 (3.8 mg, 43%). MS found: $(M+H)^+=391$.

Example 149

(S)-1-(1-(4-fluorophenyl)-5,6-dimethyl-4,5-dihydro-1H-indazol-5-yl)-3-phenylpropan-1-one Using a procedure analogous to reaction 144i, Example 147 was converted to Example 149. MS found: $(M+H)^+=375$.

Examples 150 and 151

(R)-1-((S)-1-(4-fluorophenyl)-5,6-dimethyl-4,5-dihydro-1H-indazol-5-yl)-3-methyl-3-phenylbutan-1-ol Using a procedure analogous to reaction 1i, the aldehyde (82.5 mg, 0.306 mmol) from reaction 144i was reacted with (2-methyl-2-phenylpropyl)magnesium chloride. Silica gel chromatography (0-30% EtOAc-hexanes) gave Example 150 (45.2 mg, 37%, fast eluting isomer), Example 151 (12.2 mg, 10%, slow eluting isomer) and a 1:1 mixture of the two isomers (23.6 mg, 19%). MS found: $(M+H)^+=405$.

Example 152

(S)-1-(4-fluorophenyl)-5-((R)-1-methoxy-3-methyl-3-phenylbutyl)-5,6-dimethyl-4,5-dihydro-1H-indazole In an analogous procedure to the synthesis of Examples 35, Example 151 (10.5 mg, 0.026 mmol) was converted to Example 152 (6 mg, 55%). MS found: $(M+H)^+=419$.

Example 153

(S)-1-(1-(4-fluorophenyl)-5,6-dimethyl-4,5-dihydro-1H-indazol-5-yl)-3-methyl-3-phenylbutan-1-one Using a procedure analogous to reaction 144i, the mixture of Examples 150 and 151 (23.6 mg, 0.0583 mmol) was converted to Example 153 (0.20.5 mg, 87%). MS found: $(M+H)^+=403$.

Example 154

(S)-1-(4-fluorophenyl)-5,6-dimethyl-5-(phenylthiomethyl)-4,5-dihydro-1H-indazole A mixture of the alcohol (106.6 mg, 0.391 mmol) from reaction 144h diphenyl disulfide (511 mg, 6 eq) and tributylphosphine (0.771 mL, 8 eq) in THF (6 mL) was heated at 80° C. for 20 h and concentrated. Silica gel chromatography (5-25% EtOAc-hexanes) gave Example 154 (136.6 mg, 96%). MS found: $(M+H)^+=365$.

Example 155

(5S)-1-(4-fluorophenyl)-5,6-dimethyl-5-(phenylsulfinylmethyl)-4,5-dihydro-1H-indazole

Example 156

(S)-1-(4-fluorophenyl)-5,6-dimethyl-5-(phenylsulfonylmethyl)-4,5-dihydro-1H-indazole Oxone (296 mg, 1.5 eq) was added to the sulfide (116.8 mg, 0.320 mmol) from Example 154 in MeOH (5 mL) and water (5 mL) at 0° C. After 3 h at 0° C., the MeOH was evaporated in vacuo. The residue was diluted with EtOAc (30 mL), washed with NaHCO$_3$ (2×5 mL), brine (5 mL), dried (MgSO$_4$) and concentrated. Silica gel chromatography (10-50% EtOAc-hexanes) gave sulfoxide Example 155 (57.8 mg, 48%) and sulfone Example 156 (13.9 mg, 11%). MS found: $(M+H)^+=381$ for sulfoxide, 397 for sulfone.

Example 157

(S)-1-(4-fluorophenyl)-5,6-dimethyl-N-(2-phenylpropan-2-yl)-4,5-dihydro-1H-indazole-5-carboxamide (157a) A mixture of the ester from reaction 144g (580.4 mg, 1.70 mmol), trifluoroacetic acid (10 mL) and CH$_2$Cl$_2$ (10 mL) was stirred at room temperature for 15 h, then concentrated. Silica gel chromatography (0-10% MeOH—CH$_2$Cl$_2$) gave the desired acid (573 mg, 100%). MS found: $(M+H)^+=287$.

(157b) 2-Phenylpropan-2-amine (31.4 mg, 2 eq), HOBt monohydrate (23.5 mg, 1.5 eq), EDC hydrochloride (40 mg, 1.8 eq) and Hunig base (0.121 mL, 6 eq) were added to the acid from reaction 157a (31.9 mg, 0.116 mmol) in CH$_3$CN (2 mL) at room temperature. The resultant mixture was stirred at room temperature for 30 min and at 80° C. for 15 h. Following addition of EtOAc (30 mL), the mixture was washed with saturated NH$_4$Cl (5 mL), brine (5 mL), dried (MgSO$_4$) and concentrated. Silica gel chromatography (10-50% EtOAc-hexanes) gave Example 157 (25.5 mg, 55%). MS found: $(M+H)^+=404$.

Example 158

(S)-benzyl 1-(4-fluorophenyl)-5,6-dimethyl-4,5-dihydro-1H-indazol-5-ylcarbamate

Diphenylphosphoryl azide (669 mg, 1.3 eq) was added to the acid from reaction 157a (535 mg, 1.87 mmol) and triethylamine (0.65 mL, 2.5 eq) in benzene (20 mL). After 1 h at room temperature, benzyl alcohol (0.387 mL, 2 eq) was added. The mixture was heated to reflux for 18 h, then con-

Example 159

(S)-allyl 1-(4-fluorophenyl)-5,6-dimethyl-4,5-dihydro-1H-indazol-5-ylcarbamate

In an analogous procedure to the synthesis of Examples 158, the acid from reaction 157a was reacted with allylic alcohol to give Example 159. MS found: $(M+H)^+=342$.

Example 160

(S)-N-((1-(4-fluorophenyl)-5,6-dimethyl-4,5-dihydro-1H-indazol-5-yl)methyl)aniline To a $CH_2Cl_2$ (2 mL) solution of the aldehyde (65.8 mg, 0.24 mmol) from reaction 144i was added aniline (33.3 mg, 1.5 eq) and 4 A molecular sieve (28.5 mg). The mixture was heated at 60° C. for 16 h then cooled to room temperature. NaBH(OAc)$_3$ (172 mg, 3 eq) was added. The mixture was stirred at room temperature overnight then purified by silica gel chromatography (0-20% EtOAc-hexanes) to give Example 160 (83.5 mg, 99%) as a yellow oil. MS found: $(M+H)^+=348$.

Example 161

(S)-N-((1-(4-fluorophenyl)-5,6-dimethyl-4,5-dihydro-1H-indazol-5-yl)methyl)-N-phenylacetamide A $CH_2Cl_2$ (1 mL) solution of Example 160 (18.6 mg, 0.054 mmol), acetic anhydride (50.6 µL, 10 eq) and triethylamine (74.6 µL, 10 eq) was stirred at room temperature for 19 h. The mixture was purified by silica gel chromatography (0-55% EtOAc-hexanes) to give Example 161 (18.1 mg, 87%). MS found: $(M+H)^+=390$.

Example 162

(S)-N-ethyl-N-((1-(4-fluorophenyl)-5,6-dimethyl-4,5-dihydro-1H-indazol-5-yl)methyl)aniline To a THF (1 mL) solution of Example 161 (11.5 mg, 0.030 mmol) was added LiAlH$_4$ (12 mg, 10 eq). The suspension was stirred at room temperature for 2 h, then quenched by slowly adding 1 N NaOH and diluted with water. The mixture was extracted with EtOAc. The extract was concentrated and purified by silica gel chromatography (0-20% EtOAc-hexanes) to give Example 162 (5.6 mg, 50%). MS found: $(M+H)^+=376$.

Example 163

(S)-(1-(4-fluorophenyl)-5,6-dimethyl-4,5-dihydro-1H-indazol-5-yl)methyl tert-butylcarbamate A $ClCH_2CH_2Cl$ (1 mL) solution of the alcohol (14.7 mg, 0.054 mmol) from reaction 144h, tert-butyl isocyanate (50.8 µL, 8 eq) and triethylamine (76 µL, 10 eq) was heated at 120° C. for 15 h in a sealed tube. The crude material was purified by reverse-phase HPLC (85-100% solvent B gradient) to give Example 163 (11.2 mg, 56%). MS found: $(M+H)^+=372$.

Example 164

(S)-(1-(4-fluorophenyl)-5,6-dimethyl-4,5-dihydro-1H-indazol-5-yl)methyl phenyl carbonate A $ClCH_2CH_2Cl$ (1 mL) solution of the alcohol (16 mg, 0.059 mmol) from reaction 144h, phenyl chloroformate (29.6 µL, 4 eq) and triethylamine (41 µL, 5 eq) was heated at 60° C. for 2 h in a sealed tube. The crude mixture was purified by reverse-phase HPLC (85-100% solvent B gradient) to give Example 164 (4.8 mg, 21%). MS found: $(M+H)^+=393$.

Example 165

(S)-(1-(4-fluorophenyl)-5,6-dimethyl-4,5-dihydro-1H-indazol-5-yl)methyl phenylcarbamate A $ClCH_2CH_2Cl$ (1 mL) solution of the alcohol (13.6 mg, 0.050 mmol) from reaction 144h, phenyl isocyanate (21.9 µL, 4 eq) and triethylamine (35 µL, 5 eq) was heated at 60° C. for 2 h in a sealed tube. The crude mixture was purified by reverse-phase HPLC (85-100% solvent B gradient) to give Example 165 (15.5 mg, 79%). MS found: $(M+H)^+=392$.

Example 166

(S)-(1-(4-fluorophenyl)-5,6-dimethyl-4,5-dihydro-1H-indazol-5-yl)methyl phenylcarbamate (166a) A $ClCH_2CH_2Cl$ (2 mL) solution of the aldehyde (68 mg, 0.252 mmol) from reaction 144i and O-benzylhydroxylamine (110.4 mg, 4 eq) was stirred at room temperature for 4 h. The crude mixture was purified by silica gel chromatography (0-30% EtOAc-hexanes) to give the oxime (85.3 mg, 91%). MS found: $(M+H)^+=376$.

(166b) To a formic acid (10 mL) solution of the oxime (85.3 mg, 0.227 mmol) from reaction 166a was added zinc powder (1 g, 68 eq) and the suspension was heated to reflux for 1 h. The mixture was diluted with EtOAc and filtered through celite. The filtrate was concentrated. The residue was dissolved in EtOAc, washed with water and brine, dried (MgSO$_4$), and concentrated to give the crude amine (51.3 mg). MS found: $(M+H)^+=272$.

(166c) A $ClCH_2CH_2Cl$ (1.5 mL) solution of the amine (11.5 mg) from reaction 166b, phenyl chloroformate (12 µL, 2 eq) and triethylamine (17.5 PL, 3 eq) was stirred at room temperature for 19 h. The crude mixture was purified by reverse-phase HPLC (75-95% solvent B gradient) to give example 166 (5.7 mg, 34% 2-step). MS found: $(M+H)^+=392$.

Example 167

(S)-1-tert-butyl-3-((1-(4-fluorophenyl)-5,6-dimethyl-4,5-dihydro-1H-indazol-5-yl)methyl)urea A $ClCH_2CH_2Cl$ (1.5 mL) solution of the amine (14 mg) from reaction 166b and tert-butyl isocyanate (12 µL, 2 eq) was stirred at room temperature for 19 h. The crude mixture was purified by reverse-phase HPLC (75-95% solvent B gradient) to give example 167 (4.7 mg, 24% 2-step). MS found: $(M+H)^+=371$.

Example 168

(R,E)-1-(4-fluorophenyl)-5,6-dimethyl-5-styryl-4,5-dihydro-1H-indazole

A 1 M THF solution of NaHMDS (5.59 mL, 3 eq) was added to diethyl benzylphosphonate (1.48 g, 3.5 eq) in THF (50 mL) at −78° C. The mixture was stirred at 0° C. for 1 h, then cooled to −78° C. The aldehyde from reaction 144i (503 mg, 1.86 mmol) in THF (5 ml-L) was added dropwise. The mixture was stirred at −78° C. for 2 h, and quenched with saturated NH$_4$Cl (100 mL). THF was evaporated in vacuo. The residue was extracted with EtOAc (3×100 mL). The extracts were washed with brine (10 mL), dried (MgSO$_4$) and concentrated. Silica gel chromatography (0-15% EtOAc-hexanes) gave Example 168 (401.5 mg, 63%). MS found: (M+H)$^+$=345.

Example 169

(S)-5-(1,3-dioxolan-2-yl)-1-(4-fluorophenyl)-5,6-dimethyl-4,5-dihydro-1H-indazole To a CH$_2$Cl$_2$ (5 mL) solution of the aldehyde (27.9 mg, 0.103 mmol) from reaction 144i and bis(O-trimethylsilyl) ethylene glycol (350 µL, 14 eq) was added TMSOTf (50 µL, 2.7 eq) at room temperature. The mixture was stirred for 1 h then purified by silica gel chromatography (0-35% EtOAc-hexanes) to give Example 169 (30.9 mg, 95%). MS found: (M+H)$^+$=315.

Example 170

(5S)-5-(4H-benzo [d][1,3]dioxin-2-yl)-1-(4-fluorophenyl)-5,6-dimethyl-4,5-dihydro-1H-indazole A ClCH$_2$CH$_2$Cl (1 mL) solution of the aldehyde (17.8 mg, 0.066 mmol) from reaction 144i, 2-hydroxylbenzyl alcohol (11.7 mg, 1.4 eq), pTsOH.H$_2$O (3.4 mg, 0.27 eq) and anhydrous Na$_2$SO$_4$ (69 mg) was heated at 50° C. in a sealed tube for 24 h. The crude mixture was purified by silica gel chromatography (0-40% EtOAc-hexanes) to give Example 170 (6.1 mg, 25%). MS found: (M+H)$^+$=377.

Example 171

(S)-3-(1-(4-fluorophenyl)-5,6-dimethyl-4,5-dihydro-1H-indazol-5-yl)-N-(1,3,4-thiadiazol-2-yl)propanamide (171a) A mixture of the aldehyde 144i (109 mg, 0.40 mmol) and methyl (triphenylphosphoranylidene)acetate (337 mg, 1.00 mmol) in acetonitrile (3.3 mL) was heated at 80° C. for 24 h. The reaction mixture was concentrated under reduced pressure and purified by flash column chromatography (silica, 20% ethyl acetate in hexanes) to provide the intermediate alpha, beta unsaturated ester as an oil (108 mg, 83%). MS found: (M+H)$^+$=327. 1H NMR (400 MHz, chloroform-D) δ ppm 1.27 (s, 3 H) 1.81 (s, 3 H) 2.69 (d, J=16.00 Hz, 1 H) 2.80 (d, J=16.00 Hz, 1H) 3.70 (s, 2 H) 5.80 (d, J=15.77 Hz, 1 H) 6.32 (s, 1 H) 6.89 (d, J=15.77 Hz, 1 H) 7.12-7.19 (m, 2 H) 7.39 (s, 1 H) 7.44 (dd, J=9.16, 5.09 Hz, 1 H).

(171b) To a solution of the product of reaction 171a (108 mg, 0.33 mmol) in anhydrous methanol was added magnesium turnings (81 mg, 3.30 mmol) which had previously been dried at 120° C. overnight under vacuum. The mixture was stirred under nitrogen for 2.5 h, gradually giving a nearly homogenous solution. 3N aqueous HCl (8 mL) was then added dropwise to the reaction mixture, initially giving a gelatinous mixture which gradually became a free-flowing solution upon agitation, which was partitioned between ethyl acetate and water. The organic layer was washed sequentially with saturated aqueous sodium bicarbonate and brine, dried over sodium sulfate, and concentrated. Purification of the residue by flash column chromatography (silica, 20% ethyl acetate in hexanes to 50% ethyl acetate in hexanes) provided the ester as an oil (68 mg, 63%). MS found: (M+H)$^+$=329. 1H NMR (400 MHz, CHLOROFORM-D) δ ppm 1.10 (s, 3 H) 1.67-1.83 (m, 2 H) 1.86 (s, 3 H) 2.19-2.37 (m, 2 H) 2.54 (d, J=16.00 Hz, 1 H) 2.66 (d, J=16.00 Hz, 1 H) 3.62 (s, 3 H) 6.23 (s, 1 H) 7.14 (t, J=8.39 Hz, 2 H) 7.37 (s, 1 H) 7.39-7.49 (m, 2 H)

(171c) A cloudy mixture of the product of reaction 171b (68 mg, 0.21 mmol) in THF (4 mL) and 1N aqueous lithium hydroxide (2.07 mL) was stirred at room temperature for 16 h. The reaction mixture was partitioned between ethyl acetate and 1N aqueous HCl. The organic layer was dried over sodium sulfate and concentrate to give the carboxylic acid as an oil (64 mg, 99%). MS found: (M+H)$^+$=315

(171d) To a solution of the product of reaction 171c (64 mg, 0.20 mmol) in acetonitrile (2 mL) were sequentially added triethylamine (0.112 mL, 0.80 mmol), HATU (93 mg, 0.24 mmol), and 2-amino-1,3,4-thiadiazole (40 mg, 0.40 mmol). The mixture was heated at 45° C. for 3 h, then partitioned between ethyl acetate and 1N HCl. The organic layer was washed with saturated aqueous sodium bicarbonate and brine, dried over sodium sulfate, and concentrate. Purification by flash column chromatography (silica, 90% ethyl acetate in hexanes to 100% ethyl acetate) provided the title compound as a white solid (68 mg, 86%). MS found: (M+H)$^+$=398. 1H NMR (400 MHz, CHLOROFORM-D) δ ppm 1.20 (s, 3 H) 1.85-1.98 (m, 5 H) 2.54-2.74 (m, 3 H) 2.82 (d, J=15.77 Hz, 1 H) 6.21 (s, 1 H) 7.17 (dd, J=8.39 Hz, 2 H) 7.41 (dd, J=8.65, 4.58 Hz, 2H) 7.51 (s, 1H) 8.77 (s, 1H).

Example 172

(S)-3-(1-(4-fluorophenyl)-5,6-dimethyl-4,5-dihydro-1H-indazol-5-yl)-N-(thiazol-2-yl)propanamide)

The title compound was prepared in a manner analogous to the preparation of the title compound of Example 171, replacing and 2-amino-1,3,4-thiadiazole with 2-aminothiazole. MS found: (M+H)$^+$=397. 1H NMR (400 MHz, chloroform-D) δ ppm 1.20 (s, 3 H) 1.79-1.90 (m, 2 H) 1.91 (s, 3 H) 2.53-2.68 (m, 3 H) 2.79 (d, J=16.00 Hz, 1 H) 6.23 (s, 1 H) 7.06 (d, J=4.07 Hz, 1 H) 7.17 (t, J=8.65 Hz, 2 H) 7.39-7.50 (m, 4 H).

Example 173

(S)-N-(4,5-dimethylthiazol-2-yl)-3-(1-(4-fluorophenyl)-5,6-dimethyl-4,5-dihydro-1H-indazol-5-yl)propanamide The title compound was prepared in a manner analogous to the preparation of the title compound of Example 171, replacing 2-amino-1,3,4-thiadiazole with 4,5-dimethyl-2-aminothiazole. MS found: (M+H)$^+$=425. 1H NMR (400 MHz, chloroform-D) δ ppm 1.20 (s, 3 H) 1.75-1.86 (m, J=8.65, 6.10 Hz, 1 H) 1.87-1.97 (m, 1 H) 1.91 (s, 3 H) 2.29 (s, 6 H) 2.50-2.57 (m, 2 H) 2.62 (d, J=16.28 Hz, 1 H) 2.80 (d, J=16.00 Hz, 1 H) 6.20 (s, 1 H) 7.19 (t, J=8.65 Hz, 2 H) 7.44 (dd, J=9.16, 4.58 Hz, 1 H) 7.51 (s, 1 H).

Example 174

(S)-3-(1-(4-fluorophenyl)-5-methyl-4,5,6,7-tetrahydro-1H-indazol-5-yl)-N-(1,3,4-thiadiazol-2-yl)propanamide (174a) A mixture of the aldehyde of reaction 129e (207 mg, 0.81 mmol) and methyl(triphenylphosphoranylidene)acetate (555 mg, 1.66 mmol) in acetonitrile (7.0 mL) was heated at 80° C. for 22 h. The reaction mixture was concentrated under reduced pressure and purified by flash column chromatography (silica, 20% ethyl acetate in hexanes to 30% ethyl acetate in hexanes) to provide the intermediate alpha, beta unsaturated ester as an oil (234 mg, 93%). MS found: $(M+H)^+=313$. 1H NMR (400 MHz, chloroform-D) δ ppm 1.27 (s, 3 H) 2.72 (d, J=16.00 Hz, 1 H) 2.81 (d, J=16.00 Hz, 1 H) 3.67 (s, 3 H) 5.65 (d, J=9.66 Hz, 1 H) 5.81 (d, J=15.77 Hz, 1 H) 6.46 (d, J=10.68 Hz, 1 H) 6.93 (d, J=15.77 Hz, 1 H) 7.12 (t, J=8.00 Hz, 2H) 7.39 (s, 1 H) 7.39-7.45 (m, 2 H).

(174b) A solution of the product of reaction 174a (51 mg, 0.16 mmol) in ethyl acetate (2 mL) was treated with palladium on carbon catalyst (10% w/w, 5 mg). The atmosphere was exchanged for hydrogen gas (balloon) and stirred at room temperature for 16 h. The reaction mixture was purged with nitrogen gas, filtered through a 0.45 um filter, and concentrated to give the ester as an oil (54 mg, 99%). MS found: $(M+H)^+=317$. 1H NMR (400 MHz, chloroform-D) δ ppm 1.60 (t, J=6.36 Hz, 2 H) 1.66-1.74 (m, 2 H) 2.29-2.43 (m, 4 H) 2.68 (t, J=6.36 Hz, 2 H) 3.66 (s, 3 H) 7.08-7.15 (m, 2 H) 7.41 (s, 1 H) 7.46 (dd, J=9.16, 4.58 Hz, 2 H).

(174c) The intermediate carboxylic acid was prepared in a manner analogous to that described above for the preparation of the intermediate carboxylic acid 171c of Example 171. MS found: $(M+H)^+=313$.

(174d) The title compound was prepared in a manner analogous to that described above for the preparation of the title compound of Example 171 from the intermediate 174c. MS found: $(M+H)^+=386$. 1H NMR (400 MHz, chloroform-D) δ ppm 1.07 (s, 3 H) 1.70 (t, J=6.36 Hz, 2 H) 1.81-1.91 (m, 2 H) 2.42 (d, J=16.00 Hz, 1 H) 2.51 (d, J=16.00 Hz, 1 H) 2.68 (t, J=6.10 Hz, 2 H) 2.73-2.86 (m, 2 H) 7.08-7.21 (m, 2 H) 7.42 (dd, J=9.16, 4.58 Hz, 2 H) 7.56 (s, 1 H) 8.79 (s, 1 H).

Example 175

5-((R)-2-ethoxy-2-phenylethyl)-1-(4-fluorophenyl)-5-methyl-4,5-dihydro-1H-indazole (175a) NaH (3.52 g, 3.0 eq) was added to a solution of (R)-(+)-3-chloro-1-phenyl-1-propanol (5.00 g, 29.3 mmol) and ethyl iodide (14.6 g, 3.0 eq) in DMF (50 mL) at room temperature. After 1 h at room temperature, the mixture was carefully quenched with H$_2$O (10 mL), diluted with EtOAc (400 mL), washed with H$_2$O (50 mL), brine (50 mL), dried (MgSO$_4$) and concentrated. The crude ether was taken to the step without purification.

(175b) NaCN (4.31 g, 3.0 eq) was added to a solution of the crude ether from reaction 175a (6.30 g, 29.3 mmol) in DMSO (30 mL) at room temperature. The mixture was heated to 60° C. for 6 h then cooled to room temperature. After addition of H$_2$O (10 mL) and EtOAc (400 mL), the mixture was washed with H$_2$O (50 mL), brine (50 mL), dried (MgSO$_4$) and concentrated. Silica gel chromatography (EtOAc-hexane, 0 to 20%) yielded the desired nitrile (4.95 g, 89% for 2 steps).

(175c) A 1.6 M solution of n-BuLi in hexane (17.0 mL, 1.05 eq) was added to a solution of N,N-diisopropylamine (2.38 g, 1.1 eq) in THF (80 mL) at −78° C. The mixture was warmed to 0° C. for 0.5 h then cooled to −78° C. A solution of the nitrile from reaction 175b (4.90 g, 25.9 mmol) in THF (20 mL) was added over 20 minutes. After 1 h at −78° C., methyl iodide (4.05 g, 1.1 eq) was added. The mixture was stirred at 0° C. for 1 h, quenched with saturated NaHCO$_3$ (30 mL) and diluted with EtOAc (800 mL), washed with water (80 mL), brine (80 mL), dried (MgSO$_4$) and concentrated. Silica gel chromatography (EtOAc-hexane, 0 to 20%) gave the desired product (4.20 g, 80%). MS found: $(M+H)^+=204$.

(175d) A 1.6 M solution of n-BuLi in hexane (14.1 mL, 1.2 eq) was added to a solution of N,N-diisopropylamine (1.80 g, 1.2 eq) in THF (60 mL) at −78° C. The mixture was stirred at 0° C. for 0.5 h, then cooled to −78° C. A solution of the nitrile from reaction 175c (3.00 g, 14.8 mmol) in THF (10 mL) was added over 20 minutes. After 0.5 h at −78° C., HMPA (12 mL, 5 eq) was added. The mixture was stirred at −78° C. for 10 minutes. After addition of 4-bromo-1-butene (2.40 g, 1.2 eq), the mixture was warmed to 0° C. over 1h, quenched with saturated NaHCO$_3$ (30 mL) and diluted with EtOAc (600 mL). The mixture was washed with water (60 mL), brine (60 mL), dried (MgSO$_4$) and concentrated. Silica gel chromatography (EtOAc-hexane, 0 to 20%) yielded the desired product (3.40 g, 89%). MS found: $(M+H)^+=258$.

(175e) A 1.5 M solution of DIBAL in toluene (3.0 mL, 2.0 eq) was added dropwise to a solution of the product from reaction 175d (514 mg, 2.00 mmol) in toluene (5 mL) at −78° C. After 1 h −78° C., methanol (1 mL) and 1N HCl (2 mL) were added. The mixture was diluted with EtOAc (100 mL), washed with water (5 mL), saturated NaHCO$_3$ (5 mL), brine (5 mL), dried (MgSO$_4$) and concentrated. The residue was purified by silica gel chromatography (EtOAc-hexane, 0 to 10%) to yield the desired aldehyde (310 mg, 60%). MS found: $(M+Na)^+=283$.

(175f) PdCl$_2$ (20 mg, 0.1 eq) and Cu(OAc)$_2$ were added to a solution of the aldehyde from reaction 175e (300 mg, 1.15 mmol) in N,N-dimethylacetamide (4.2 mL) and H$_2$O (0.6 mL). The mixture was stirred under an oxygen balloon for 24 h, diluted with EtOAc (100 mL), washed with water (5 mL), brine (5 mL), dried (MgSO$_4$) and concentrated. The residue was purified by silica gel chromatography (EtOAc-hexane, 0 to 30%) to yield the desired ketone (212 mg, 67%). MS found: $(M+Na)^+=299$.

(175g) Using conditions analogous to reaction 1c, the ketone from reaction 175f (6.30 g, 22.8 mmol) was converted to the desired cyclic ketone as a 2:1 mixture of two diastereomers (4.80 g, 82%). Separation by chiral AS column (isocratic, i-PrOH/CO$_2$, 10/90) gave the major diastereomer A (2.40 g, faster eluent) and the minor diastereomer B (1.10 g, slower eluent). MS found: $(M+Na)^+=281$.

(175h) In analogous procedures to reactions 1d-1e, the major diastereomer A from reaction 175g (2.40 g, 9.30 mmol) was converted to Example 175 (2.95 g, 84% for 2 steps). MS found: $(M+H)^+=377$.

Example 176

5-((R)-2-ethoxy-2-phenylethyl)-1-(4-fluorophenyl)-5-methyl-6-(((trimethylsilyl)ethynyl)-4,5-dihydro-1H-indazole (176a) Using similar procedures to reaction 135a-b, the compound from Example 175 (1.00 g, 2.66 mmol) was converted to the desired alcohol as a 1:1 mixture of two isomers (870 mg, 83% for 2 steps). MS found: $(M+H)^+=395$.

(175b) Using a procedure analogous to reaction 137a the alcohol from reaction 176a (870 mg, 2.21 mmol) was converted to the desired ketone (600 mg, 69%). MS found: (M+H)$^+$=393.

(176c) NaH (24 mg, 3.0 eq, 60% in mineral oil) was added to a solution of the ketone from reaction 176b (78 mg, 0.200 mmol) in DMF (3 mL) at room temperature. After stirring for 10 minutes, the mixture was cooled to 0° C. A solution of N-phenyltrifluoromethanesulfonimide (78 mg, 1.1 eq) in DMF (1 mL) was added. The resultant mixture was stirred at 0° C. for 0.5 h, quenched with saturated NaHCO$_3$ (2 mL), diluted with EtOAc (80 mL), washed with water (5 mL), brine (5 mL), dried (MgSO$_4$) and concentrated. The residue was purified by silica gel chromatography (EtOAc-hexane, 0 to 30%) to yield the desired triflate (80 mg, 75%). MS found: (M+H)$^+$=525.

(176d) Copper (I) Iodide (2 mg, 0.1 eq), (trimethylsilyl)acetylene (10 mg, 1.4 eq) and dichlorobis(triphenylphosphine) palladium (11) (5 mg, 0.1 eq) were added to a solution of the triflate from reaction 176c (38 mg, 0.073 mmol) and triethylamine (22 mg, 3.0 eq) in THF (3 mL) at room temperature. The mixture was stirred under N$_2$ for 2 h, quenched with saturated NaHCO$_3$ (2 mL), diluted with EtOAc (80 mL), washed with water (5 mL), brine (5 mL), dried (MgSO$_4$) and concentrated. The residue was purified by silica gel chromatography (EtOAc-hexane, 0 to 20%) to yield Example 176 (24 mg, 70%). MS found: (M+H)$^+$=473.

Example 177

5-((R)-2-ethoxy-2-phenylethyl)-6-ethynyl-1-(4-fluorophenyl)-5-methyl-4,5-dihydro-1H-indazole A 1.0 M solution of tetrabutylammonium fluoride in THF (0.085 mL, 2.0 eq) was added to a solution of Example 176 (20 mg, 0.042 mmol) in THF (1 mL) at 0° C. The mixture was stirred for 1 h, quenched with saturated NaHCO$_3$ (2 mL), diluted with EtOAc (80 mL), washed with water (5 mL), brine (5 mL), dried (MgSO$_4$) and concentrated. The residue was purified by silica gel chromatography (EtOAc-hexane, 0 to 20%) to yield Example 177 (13 mg, 77%). MS found: (M+H)$^+$=401.

Example 178

5-((R)-2-ethoxy-2-phenylethyl)-1-(4-fluorophenyl)-5-methyl-6-phenyl-4,5-dihydro-1H-indazole A 0.5 M solution of phenylzinc bromide in THF (0.23 mL, 3.0 eq) and tetrakis(triphenylphosphine)palladium(0) (8.0 mg, 0.2 eq) were added to a solution of the triflate from reaction 176c (20 mg, 0.038 mmol) in THF (2 mL). The mixture was heated to reflux for 4 h, cooled to room temperature and quenched with saturated NH$_4$Cl (1 mL). After addition of EtOAc (60 mL), the mixture was washed with water (5 mL), brine (5 mL), dried (MgSO$_4$) and concentrated. The residue was purified by silica gel chromatography (EtOAc-hexane, 0 to 30%) to yield Example 178 (12 mg, 70%). MS found: (M+H)$^+$=453.

Example 179

5-((R)-2-ethoxy-2-phenylethyl)-1-(4-fluorophenyl)-5-methyl-4,5-dihydro-1H-indazole-6-carbonitrile Bis(dibenzylideneacetone)palladium (13 mg, 0.3 eq), diphenylphosphinoferrocene (25 mg, 0.6 eq), zinc (20 mg, 4.0 eq) and zinc cyanide (89 mg, 10 eq) were added to a solution of the triflate from reaction 176c (40 mg, 0.076 mmol) in N,N-dimethylformamide (2 mL). The mixture was heated to 100° C. under nitrogen for 2 h, cooled to room temperature and quenched with saturated NaHCO$_3$ (2 mL). After addition of EtOAc (80 mL), the mixture was washed with water (5 mL), brine (5 mL), dried (MgSO$_4$) and concentrated. The residue was purified by silica gel chromatography (EtOAc-hexane, 0 to 30%) to yield Example 179 (10 mg, 33%). MS found: (M+H)$^+$=402.

Example 180

6-chloro-5-((R)-2-ethoxy-2-phenylethyl)-1-(4-fluorophenyl)-5-methyl-4,5-dihydro-1H-indazole (180a) Lithium carbonate (12.7 mg, 1.0 eq) and lithium chloride (51 mg, 7.0 eq) were added to a solution of the triflate from reaction 176c (90 mg, 0.17 mmol) in THF (4 mL). After heating to reflux for 0.5 h, additional hexamethylditin (56 mg, 1.0 eq) in THF (2 mL) followed by tetrakis(triphenylphosphine)palladium(0) (40 mg, 0.2 eq) were added. The resultant mixture was kept at reflux for 3 h, cooled to room temperature and quenched with saturated NaHCO$_3$ (4 mL). After addition of EtOAc (80 mL), the mixture was washed with water (5 mL), brine (5 mL), dried (MgSO$_4$) and concentrated. The residue was purified by silica gel chromatography (EtOAc-hexane, 0 to 30%) to yield the desired tin compound (70 mg, 76%). MS found: (M+H)$^+$=539.

(180b) Copper(II) chloride (20 mg, 3.0 eq) was added to a solution of the tin compound from reaction 180a (27 mg, 0.050 mmol) in THF (2 mL) at 0° C. The mixture was stirred at room temperature for 4 h and quenched with saturated NaHCO$_3$ (2 mL). After addition of EtOAc (80 mL), the mixture was washed with water (5 mL), brine (5 mL), dried (MgSO$_4$) and concentrated. The residue was purified by reverse phase HPLC (methanol/water, 70% to 100%, 30 minutes) to yield Example 180 (8 mg, 39%). MS found: (M+H)$^+$=411.

Example 181

(S)-1-(1-(4-fluorophenyl)-5,6-dimethyl-4,5-dihydro-1H-indazol-5-yl)-2-phenylethane-1,2-dione (181a) A solution of Example 201 (360 mg, 1.00 mmol) in THF (2 mL) was added to a solution of sodium bis(trimethylsilyl)amide (1.5 mmol, 1.5 eq) in THF (6 mL) at −78° C. After 0.5 h at −78° C., a solution of (1S)-(+)-(10-camphorsulfonyl)oxaziridine (458 mg, 2.0 eq) in THF (2 mL) was added. The mixture was stirred at −78° C. for 1 h and quenched with saturated NH$_4$Cl (2 mL). After addition of EtOAc (200 mL), the mixture was washed with water (20 mL), brine (20 mL), dried (MgSO$_4$) and concentrated. The residue was purified by silica gel chromatography (EtOAc-hexane, 10 to 50%) to yield the desired alcohol as an 8:1 mixture of two diastereomers (360 mg, 96%). MS found: (M+H)$^+$=377.

(181b) Iron(III) perchlorate hydrate (30 mg, 0.25 eq) was added to a solution of the alcohol from reaction 181a (120 mg, 0.32 mmol) at room temperature. The mixture was heated to 45° C. for 3 h, cooled to room temperature and concentrated. The residue was purified by silica gel chromatography (EtOAc-hexane, 0 to 30%) to yield Example 181 (30 mg, 25%). MS found: $(M+H)^+=375$.

Examples 182 and 183

1-((S)-1-(4-fluorophenyl)-5,6-dimethyl-4,5-dihydro-1H-indazol-5-yl)-2-hydroxy-2-phenylethanone The alcohol mixture from reaction 181a (240 mg, 0.67 mmol) was purified by chiral OD column (isocratic, isopropanol/heptane, 15/85) to provide Example 182 (120 mg, faster eluent) and Example 183 (14 mg, slower eluent). MS found: $(M+H)^+=377$.

Examples 184 and 185

2-(benzo[b]thiophen-3-yl)-1-((R)-1-(4-fluorophenyl)-5,6-dimethyl-4,5-dihydro-1H-indazol-5-yl)propan-2-ol (184a) Using a procedure analogous to reaction 1i, the enantiomer A of the aldehyde from reaction 1h (60 mg, 0.212 mmol) was converted to the desired alcohol as a mixture of two diastereomers (80 mg, 90%). MS found: $(M+H)^+=419$.

(184b) Using a procedure analogous to reaction 144i the alcohol from reaction 184a (80 mg, 0.19 mmol) was converted to the desired ketone (60 mg, 76%). MS found: $(M+H)^+=417$.

(184c) In an analogous procedure to Examples 25 and 26, the ketone from reaction 184b (55 mg, 0.132 mmol) was converted to Examples 184 (10.0 mg, 18%, faster eluent on chiral OD column) and 185 (7.0 mg, 12%, slower eluent). MS found: $(M+H)^+=433$.

Example 186

1-(1-(4-fluorophenyl)-5-methyl-4,5-dihydro-1H-indazol-5-yl)-3-methyl-3-phenylbutan-1-ol A 0.5 M ether solution of 2-methyl-2-phenylpropylmagnesium chloride (5.16 mL, 10 eq) was added to a solution of the aldehyde from reaction 129e (66.1 mg, 0.258 mmol) in THF (10 mL). After 30 min at room temperature, the mixture was quenched with saturated NH$_4$Cl (10 mL) and water (10 mL). After evaporation of THF in vacuo, the residue was extracted with CH$_2$Cl$_2$ (3×10 mL). The combined extracts were dried (MgSO$_4$) and concentrated. Silica gel chromatography (EtOAc-hexanes, 10% to 30% gradient) gave Example 186 (67.4 mg, 67%) as a 5:3 mixture of isomers. MS found: $(M+H)^+=391$.

Examples 187 and 188

1-(1-(4-fluorophenyl)-5-methyl-4,5,6,7-tetrahydro-1H-indazol-5-yl)-3-methyl-3-phenylbutan-1-ol Using a procedure analogous to Example 186, the aldehyde (57.5 mg, 0.223 mmol) from reaction 117d was reacted with 2-methyl-2-phenylpropylmagnesium chloride to give Examples 187 (25.1 mg, 29%, fast eluting isomer from silica gel column) and 188 (17.8 mg, 20%, slow eluting isomer). MS found: $(M+H)^+=393$ for both isomers.

Examples 189 and 190

1-(1-(4-fluorophenyl)-5-methyl-4,5,6,7-tetrahydro-1H-indazol-5-yl)-3-phenylpropan-1-ol Using a procedure analogous to Example 186, the aldehyde (53.1 mg, 0.206 mmol) from reaction 117d was reacted with phenethylmagnesium chloride to give Examples 189 (35.3 mg, 47%, fast eluting isomer from silica gel column) and 190 (26.0 mg, 35%, slow eluting isomer). MS found: $(M+H)^+=365$ for both isomers.

Example 191

1-(1-(4-fluorophenyl)-5-methyl-4,5-dihydro-1H-indazol-5-yl)-3-phenylpropan-1-ol Using a procedure analogous to Example 186, the aldehyde (53.5 mg, 0.209 mmol) from reaction 129e was reacted with phenethylmagnesium chloride to give Example 191 (54.7 mg, 72%) as a 1:1 mixture of isomers. MS found: $(M+H)^+=363$.

Example 192

(R)-1-(1-(4-fluorophenyl)-5-methyl-4,5-dihydro-1H-indazol-5-yl)-4-phenylbutan-2-ol Using a procedure analogous to Example 186, the aldehyde enantiomer B (22.7 mg, 0.084 mmol) from reaction 130a was reacted with phenethylmagnesium chloride to give Example 192 (23.8 mg, 75%) as a 1:1 mixture of isomers. MS found: $(M+H)^+=377$.

Example 193

(R)-1-(1-(4-fluorophenyl)-5-methyl-4,5-dihydro-1H-indazol-5-yl)-4-methyl-4-phenylpentan-2-ol Using a procedure analogous to Example 186, the aldehyde enantiomer B (25.5 mg, 0.084 mmol) from reaction 130a was reacted with 2-methyl-2-phenylpropylmagnesium chloride to give Example 193 (18.9 mg, 50%) as a 1:1 mixture of isomers. MS found: $(M+H)^+=405$.

Example 194

(S)-5-((4S,6S)-4,6-dimethyl-1,3-dioxan-2-yl)-1-(4-fluorophenyl)-5,6-dimethyl-4,5-dihydro-1H-indazole (194a) TMSOTf (2.47 mL, 13.59 mmol) was added to a CH$_2$Cl$_2$ (15 mL) solution of pyridine (1.0753 g, 1 eq) at 0° C. under nitrogen atmosphere. The resulting cloudy mixture was allowed to warm to room temperature and stirred overnight. The resulting clear solution was concentrated to give the desired salt as white needle crystal (3.4 g, 83%).

(194b) To a CH$_2$Cl$_2$ (5 mL) solution of (2S,4S)-(+)-pentanediol (209 mg, 2 mmol) was added the salt (1.90 g, 3.1 eq) from reaction 194a at room temperature. The mixture was stirred for 19 h, filtered through a short bed of silica gel and concentrated to give the crude bis(O-trimethylsilyl)ether (0.40 g, 80%).

(194c) Using a procedure analogous to the preparation of Example 169, the aldehyde from reaction 144i (23 mg, 0.085 mmol) was reacted with the bis(O-trimethylsilyl)ether (0.24 g, 11 eq) from reaction 194b to give the title compound (25 mg, 83%). MS found: $(M+H)^+=357$.

Example 195

(S)-2,4-difluoro-N-((1-(4-fluorophenyl)-5,6-dimethyl-4,5-dihydro-1H-indazol-5-yl)methyl)benzamide The amine (22 mg, 0.081 mmol) from reaction 166b was mixed with 2,4-difluorobenzoic acid (17 mg, 1.3 eq), HOBt monohydrate (19 mg, 1.7 eq), EDCI hydrochloride (59 mg, 3.8 eq), DIPEA (100 μL, 7 eq) in MeCN (2 mL). The mixture was heated at 70° C. for 2.5 h, then purified by reverse-phase HPLC (70 to 100% solvent B gradient) to give the title compound (4.5 mg, 14%). MS found: $(M+H)^+=412$.

Example 196

(R)-5-((1,3-dioxolan-2-yl)methyl)-1-(4-fluorophenyl)-5,6-dimethyl-4,5-dihydro-1H-indazole Using a procedure analogous to the preparation of Example 169, the aldehyde from reaction 1h (22 mg, 0.077 mmol) was reacted with bis(O-trimethylsilyl)ethylene glycol (380 μL, 20 eq) to give the title compound (16.3 mg, 64%). MS found: $(M+H)^+=329$.

Example 197

(S)-5-((4R,5R)-4,5-dimethyl-1,3-dioxolan-2-yl)-1-(4-fluorophenyl)-5,6-dimethyl-4,5-dihydro-1H-indazole (197a) Using a procedure analogous to reaction 194b, (2R,3R)-(−)-2,3-butanediol (94 mg, 1 mmol) was converted to the bis(O-trimethylsilyl)ether (221 mg, 94%).

(197b) Using a procedure analogous to the preparation of Example 169, the aldehyde from reaction 144i (16 mg, 0.059 mmol) was reacted with the bis(O-trimethylsilyl)ether (120 mg, 13 eq) from reaction 197a to give the title compound (14.4 mg, 71%). MS found: $(M+H)^+=343$.

Example 198

(R,E)-3-(1-(4-fluorophenyl)-5,6-dimethyl-4,5-dihydro-1H-indazol-5-yl)-1-phenylprop-2-en-1-one To a CH$_2$Cl$_2$ (1 mL) solution of the aldehyde from reaction 144i (65 mg, 0.24 mmol), acetophenone (56.2 mL, 2 eq) and magnesium iodide (77.5 mg, 1.2 eq) was added piperidine (28.5 μL, 1.2 eq). The mixture was stirred at room temperature for 40 min, filtered and purified by flash column chromatography (12 g ISCO silica gel cartridge, 0 to 40% EtOAc-hexanes gradient) to give the title compound (48.7 mg, 55%). MS found: $(M+H)^+=373$.

Examples 199 and 200

3-((S)-1-(4-fluorophenyl)-5,6-dimethyl-4,5-dihydro-1H-indazol-5-yl)-3-hydroxy-1-phenylpropan-1-one The title compound mixture was isolated as byproducts from the preparation of Example 198 by flash column chromatography. The mixture was separated by preparative chiral HPLC (Chiralcel OJ column, 20×500 mm, 20% IPA-heptane, 20 mL/min) to give Examples 199 (13.6 mg, 15%, fast eluting isomer) and 200 (12.4 mg, 13%, slow eluting isomer). MS found: $(M+H)^+=391$ for both isomers.

Example 201

(S)-1-(1-(4-fluorophenyl)-5,6-dimethyl-4,5-dihydro-1H-indazol-5-yl)-2-phenylethanone A CH$_2$Cl$_2$ (8 mL) solution of Example 145 (328.3 mg, 0.906 mmol) was reacted with Dess-Martin Periodinane (469.7 mg, 1.2 eq) at room temperature. After 2 h the reaction was quenched by adding aqueous NaHSO$_3$ (1.4 M, 5 mL) and stirred until the white cloudy suspension became a clear solution. The CH$_2$Cl$_2$ phase was separated, washed with saturated NaHCO$_3$ (5 mL) and purified by flash column chromatography (12 g ISCO silica gel cartridge, 0 to 25% EtOAc-hexanes) to give the title compound (303 mg, 93%). MS found: $(M+H)^+=361$.

Example 202

1-(1-(4-fluorophenyl)-5-methyl-4,5-dihydro-1H-indazol-5-yl)-3-phenylpropan-1-one Using a procedure analogous to the preparation of Example 201, Example 191 (48.5 mg, 0.134 mmol) was oxidized to give the title compound (45.3 mg, 94%). MS found: $(M+H)^+=361$.

Example 203

2-(1-(4-fluorophenyl)-5-methyl-4,5-dihydro-1H-indazol-5-yl)-4-phenylbutan-2-ol

A 3 M THF solution of methylmagnesium bromide (0.15 mL, 5.4 eq) was added to a THF (1 mL) solution of Example 202 (30 mg, 0.083 mmol) at room temperature. After 2.5 h, the reaction was quenched with saturated NH$_4$Cl and extracted with EtOAc. The EtOAc layer was concentrated and purified by flash column chromatography (4 g ISCO silica gel cartridge, 0 to 50% EtOAc-hexanes) to give the title compound (25.7 mg, 82%) as a 1:1 mixture of two isomers. MS found: $(M+H)^+=377$.

Example 204

1,1,1-trifluoro-2-(1-(4-fluorophenyl)-5-methyl-4,5-dihydro-1H-indazol-5-yl)-4-phenylbutan-2-ol To a THF (1 mL) solution of Example 202 (7 mg, 0.019 mmol) and trifluoromethyl trimethylsilane (28 μL, 6.6 eq) at 0° C. was added a 1 M THF solution of tetrabutylammonium fluoride (128 μL, 6.7 eq). The mixture was slowly warmed to room temperature overnight. HPLC showed only about 10% conversion. Additional trifluoromethyl trimethylsilane (374 μL) was added and the reaction was completed in 1 h. The mixture was concentrated and purified by reverse-phase HPLC (80 to 100% solvent B gradient) to give the title compound (2.4 mg, 29%) as a 1:1 mixture of two isomers. MS found: $(M+H)^+=431$.

Examples 205 and 206

1-((S)-1-(4-fluorophenyl)-5-methyl-4,5-dihydro-1H-indazol-5-yl)-3-phenylpropan-1-ol The mixture from Example 191 (54.9 mg) was separated by chiral HPLC (Chiralcel AD column, 50×250 mm, 10% IPA-heptane, 35 mL/in) to give Examples 205 (20.4 mg, fast eluting isomer) and 206 (31.8 mg, slow eluting isomer). MS found: (M+H)$^+$=363 for both isomers.

Example 207

1-(1-(4-fluorophenyl)-5-methyl-4,5-dihydro-1H-indazol-5-yl)-3-methyl-3-phenylbutan-1-one Using conditions analogous to the preparation of Example 201, Example 186 (41 mg, 0.105 mmol) was oxidized to give the title compound (35.9 mg, 88%). MS found: (M+H)$^+$=389.

Example 208

2-(1-(4-fluorophenyl)-5-methyl-4,5-dihydro-1H-indazol-5-yl)-4-methyl-4-phenylpentan-2-ol Using conditions analogous to the preparation of Example 203, Example 207 (10.8 mg, 0.0277 mmol) was reacted with methylmagnesium bromide to give the title compound (9 mg, 61%) as a mixture of two isomers. MS found: (M+H)$^+$=405.

Example 209

3-(1-(4-fluorophenyl)-5-methyl-4,5-dihydro-1H-indazol-5-yl)-5-methyl-5-phenylhexan-3-ol A 1.7 M pentane solution of tert-butyllithium (0.56 1 mL, 0.952 mmol) was added to an ether (5 mL) solution of iodoethane (66.9 mg, 0.429 mmol) at −78° C. After 40 min at −78° C., Example 207 (9.7 mg, 0.025 mmol) was added. After 80 min, the mixture was quenched by adding saturated NH$_4$Cl (2 mL) and warmed to room temperature. The aqueous was extracted with ethyl acetate (5 mL). The combined ethyl acetate phase was concentrated and purified by flash column chromatography (4 g ISCO silica gel cartridge, 0 to 20% EtOAc-hexanes) to give the title compound (3.5 mg, 33%). MS found: (M+H)$^+$=419.

Example 210

(S)-1-tert-butyl-3-((1-(4-fluorophenyl)-5-methyl-4,5-dihydro-1H-indazol-5-yl)methyl)urea (210a-b) Following conditions analogous to 166a-b, the aldehyde from reaction 129e (100 mg, 0.39 mmol) was converted to the primary amine (97 mg), which was taken to next step without purification. MS found: (M+H)$^+$=258.

(210c) Following conditions analogous to the preparation of Example 167, the amine (10 mg) from reaction 210b was reacted with tert-butyl isocyanate to give the title compound (6.1 mg, 44%). MS found: (M+H)$^+$=357.

Example 211

(S)-1-((1-(4-fluorophenyl)-5-methyl-4,5-dihydro-1H-indazol-5-yl)methyl)-3-(2-phenylpropan-2-yl)urea A THF (0.5 mL) solution of the amine (11 mg, 0.0428 mmol) from reaction 210b and 1,1'-carbonyldiimidazole (7.3 mg, 1 eq) was stirred at room temperature for 2 h. Cumyl amine (6.2 mg, 1 eq) was added. The mixture was heated at 75° C. for 2 h, concentrated and purified by flash column chromatography (4 g ISCO silica gel cartridge, 0 to 70% EtOAc-hexanes) to give the title compound (5.9 mg, 33%). MS found: (M+H)$^+$=419.

Example 212

(S)-N-((1-(4-fluorophenyl)-5-methyl-4,5-dihydro-1H-indazol-5-yl)methyl)-2-phenylacetamide Using conditions analogous to the preparation of Example 195, the amine (13.8 mg, 0.0536 mmol) from reaction 210b was coupled with phenylacetic acid to give the title compound (7.8 mg, 39%). MS found: (M+H)$^+$=376.

Example 213

(S)-N-((1-(4-fluorophenyl)-5-methyl-4,5-dihydro-1H-indazol-5-yl)methyl)-1-phenylcyclopropanecarboxamide Using conditions analogous to the preparation of Example 195, the amine (14.8 mg, 0.0575 mmol) from reaction 210b was coupled with 1-phenyl-1-cyclopropane carboxylic acid to give the title compound (12.1 mg, 52%). MS found: (M+H)$^+$=402.

Example 214

(S)-3-(2,4-difluorophenyl)-1-(1-(4-fluorophenyl)-5-methyl-4,5-dihydro-1H-indazol-5-yl)propan-1-ol (214a) Sodium hydride (60% suspension with mineral oil, 148.7 mg, 3.72 mmol) was washed with hexanes to removed oil. To it was added DMSO (10 mL) and trimethyloxosulfonium iodide (823 mg, 3.74 mmol) at 0° C. After stirring for 1 h, the aldehyde (118.6 mg, 0.46 mmol) from reaction 129e in DMSO (2 mL) was added at room temperature. The mixture was stirred for 1.5 h then quenched with pH 7 phosphate buffer (20 mL) and extracted with ether (2×50 mL). The combined extracts were washed with brine (5 mL) and concentrated to give the crude epoxide (109.6 mg, 88%). MS found: (M+H)$^+$=271.

(214b) To an ether (0.5 mL) suspension of CuCN (2.7 mg, 0.75 eq) was added a 0.25 M ether solution of 2,4-difluorobenzylmagnesium bromide (0.4 mL, 2.5 eq) at −20° C. under nitrogen atmosphere. After 5 min stirring, a THF (0.5 mL) solution of the epoxide (10.8 mg, 0.040 mmol) from reaction 214a was added at −10° C. The mixture was allowed to slowly warm to room temperature over 1h then quenched with methanol. After removal of solvent in vacuo, the residue was treated with CH$_2$Cl$_2$ and filtered. The filtrate was concentrated and purified by flash column chromatography (4 g ISCO silica gel cartridge, 0 to 40% EtOAc-hexanes) to give the title compound (7.5 mg, 47%) as a 2:1 mixture of isomers. MS found: (M+H)$^+$=399.

Example 215

(S)-4-(2,4-difluorophenyl)-2-(1-(4-fluorophenyl)-5-methyl-4,5-dihydro-1H-indazol-5-yl)butan-2-ol (215a) Using conditions analogous to the preparation of Example 201, Example 214 (13.8 mg, 0.0346 mmol) was oxidized to the ketone (10.2 mg, 74%). MS found: (M+H)$^+$=397.

(215b) Using conditions analogous to the preparation of Example 203, the ketone (5.1 mg, 0.0129 mmol) from 215a was reacted with methylmagnesium bromide to give the title compound (3.3 mg, 62%) as a 1:1 mixture of isomers. MS found: (M+H)$^+$=413.

Example 216

(S)-1-(1-(4-fluorophenyl)-5-methyl-4,5-dihydro-1H-indazol-5-yl)-3-(3-methoxyphenyl)propan-1-ol Using conditions analogous to the reaction 214b, the epoxide (10.8 mg, 0.040 mmol) from reaction 214a was reacted with 3-methoxybenzylmagnesium chloride to give the title compound (11.4 mg, 73%) as a 2:1 mixture of isomers. MS found: $(M+H)^+=393$.

Example 217

(S)-3-(4-chlorophenyl)-1-(1-(4-fluorophenyl)-5-methyl-4,5-dihydro-1H-indazol-5-yl)propan-1-ol Using conditions analogous to the reaction 214b, the epoxide (10 mg, 0.037 mmol) from reaction 214a was reacted with 4-chlorobenzylmagnesium chloride to give the title compound (1.9 mg, 13%) as a 2:1 mixture of isomers. MS found: $(M+H)^+=397, 399$.

Example 218

(S)-2-(1-(4-fluorophenyl)-5-methyl-4,5-dihydro-1H-indazol-5-yl)-4-(3-methoxyphenyl)butan-2-ol (218a) Using conditions analogous to the preparation of Example 201, Example 216 (7.4 mg, 0.0189 mmol) was oxidized to the ketone (4.7 mg, 64%). MS found: $(M+H)^+=391$.

(218b) Using conditions analogous to the preparation of Example 203, the ketone (4.7 mg, 0.012 mmol) from reaction 218a was reacted with methylmagnesium bromide to give the title compound (4.2 mg, 88%) as a 1:1 mixture of isomers. MS found: $(M+H)^+=407$.

Example 219

(R)-1-(1-(4-fluorophenyl)-5-methyl-4,5-dihydro-1H-indazol-5-yl)-2-methyl-4-phenylbutan-2-ol (219a) Using conditions analogous to the preparation of Example 201, Example 192 (5.3 mg, 0.014 mmol) was oxidized to the ketone (2.7 mg, 51%). MS found: $(M+H)^+=375$.

(219b) Using conditions analogous to the preparation of Example 203, the ketone (2.7 mg, 0.0072 mmol) from 219a was reacted with methylmagnesium bromide to give the title compound (2.2 mg, 79%) as a 1:1 mixture of isomers. MS found: $(M+H)^+=391$.

Example 220

(R)-1-(1-(4-fluorophenyl)-5-methyl-4,5-dihydro-1H-indazol-5-yl)-2,4-dimethyl-4-phenylpentan-2-ol (220a) Using conditions analogous to the preparation of Example 201, Example 193 (3.1 mg, 0.00766 mmol) was oxidized to the ketone (1.7 mg, 55%). MS found: $(M+H)^+=403$.

(220b) Using conditions analogous to the preparation of Example 203, the ketone (1.7 mg, 0.004 mmol) from 220a was reacted with methylmagnesium bromide to give the title compound (1.7 mg, 94%) as a 1:1 mixture of isomers. MS found: $(M+H)^+=419$.

Example 221

(S)-1-(1-(4-fluorophenyl)-5-methyl-4,5-dihydro-1H-indazol-5-yl)-3-(4-methoxyphenyl)propan-1-ol Using conditions analogous to the reaction 214b, the epoxide (46.7 mg, 0.182 mmol) from reaction 214a was reacted with 4-methoxybenzylmagnesium chloride to give the title compound (56.6 mg, 79%) as a 2:1 mixture of isomers. MS found: $(M+H)^+=393$.

Example 222

(S)-2-(1-(4-fluorophenyl)-5-methyl-4,5-dihydro-1H-indazol-5-yl)-4-(4-methoxyphenyl)butan-2-ol (222a) Using conditions analogous to the preparation of Example 201, Example 221 (27.1 mg, 0.069 mmol) was oxidized to the ketone (20.4 mg, 76%). MS found: $(M+H)^+=391$.

(222b) Using conditions analogous to the preparation of Example 203, the ketone (10.2 mg, 0.0261 mmol) from 222a was reacted with methylmagnesium bromide to give the title compound (6.8 mg, 64%) as a 1:1 mixture of isomers. MS found: $(M+H)^+=407$.

Example 223

(R)-1-(2-(1-(4-fluorophenyl)-5-methyl-4,5-dihydro-1H-indazol-5-yl)ethyl)-3-(2-phenylpropan-2-yl)urea (223a-b) Using conditions analogous to 166a-b, the aldehyde from 129w (52.3 mg, 0.194 mmol) was converted to the crude amine (58.1 mg). MS found: $(M+H)^+=272$.

(223c) Using conditions analogous to the preparation of Example 211, the amine (8 mg, 0.0295 mmol) from reaction 223b was reacted with 1,1'-carbonyldiimidazole and cumyl amine to give the title compound (4.6 mg, 36%). MS found: $(M+H)^+=433$.

Example 224

(R)-1-tert-butyl-3-(2-(1-(4-fluorophenyl)-5-methyl-4,5-dihydro-1H-indazol-5-yl)ethyl)urea Using conditions analogous to the preparation of Example 211, the amine (5.4 mg, 0.0199 mmol) from reaction 223b was reacted with 1,1'-carbonyldiimidazole and tert-butylamine to give the title compound (2.6 mg, 35%). MS found: $(M+H)^+=3371$.

Example 225

(R)-N-(2-(1-(4-fluorophenyl)-5-methyl-4,5-dihydro-1H-indazol-5-yl)ethyl)-1-phenylcyclopropanecarboxamide Using conditions analogous to the preparation of Example 195, the amine (5.3 mg, 0.0195 mmol) from reaction 223b was coupled with 1-phenyl-1-cyclopropane carboxylic acid at room temperature to give the title compound (2.3 mg, 28%). MS found: $(M+H)^+=416$.

Example 226

(R)-N-(2-(1-(4-fluorophenyl)-5-methyl-4,5-dihydro-1H-indazol-5-yl)ethyl)thiazole-2-carboxamide (226a) To an ethanol (3 mL) solution of thiazole-2-carboxylic acid ethyl ester (213 mg, 1.355 mmol) was added aqueous KOH (2 M, 3.5 mL). The mixture was stirred at room temperature for 2 h then concentrated, acidified with aqueous HCl (2 M, 3 mL). The resulting white needle crystal (43 mg) was collected from the solution by filtration.

(226b) Using conditions analogous to the preparation of Example 195, the amine (6.3 mg, 0.0232 mmol) from reaction 223b was coupled with the acid (3 mg, I eq) from reaction 226a to give the title compound (2 mg, 22%). MS found: $(M+H)^+=383$.

Example 227

(R)-N-(2-(1-(4-fluorophenyl)-5-methyl-4,5-dihydro-1H-indazol-5-yl)ethyl)-2-phenylacetamide Using conditions analogous to the preparation of Example 195, the amine (6.5 mg, 0.024 mmol) from reaction 223b was coupled with phenylacetic acid at room temperature to give the title compound (2.3 mg, 25%). MS found: $(M+H)^+=390$.

Example 228

(S)-1-benzyl-3-((1-(4-fluorophenyl)-5-methyl-4,5-dihydro-1H-indazol-5-yl)methyl)urea Using conditions analogous to the preparation of Example 211, the amine (14.5 mg, 0.056 mmol) from reaction 223b was reacted with 1,1'-carbonyldiimidazole and benzylamine to give the title compound (7.8 mg, 35%). MS found: $(M+H)^+=391$.

Example 229

(S)-1-(2,4-difluorophenyl)-3-(1-(4-fluorophenyl)-5-methyl-4,5-dihydro-1H-indazol-5-yl)pentan-3-ol Using conditions analogous to the preparation of Example 209, the ketone (7 mg, 0.018 mmol) from reaction 215a was converted to the title compound (1.5 mg, 20%) as a 1:1 mixture of isomers. MS found: $(M+H)^+=427$.

Example 230

(R)-5-((R)-2-ethoxy-2-phenylethyl)-5,6-dimethyl-4,5-dihydro-1H-indazole-1-carboxamide (230a) A 3 M ether solution of methylmagnesium bromide (5.07 mL, 1.3 eq) was added to a solution of the nitrile from reaction 175d (3.00 g, 11.7 mmol) in benzene (100 mL) at room temperature. The mixture was heated to reflux for 18 h, cooled to room temperature, and carefully quenched with 1 N HCl (50 mL). After stirring for 30 min, the mixture was diluted with brine (200 mL) and extracted with EtOAc (3×300 mL). The combined extracts were washed with saturated NaHCO₃ (10 mL), brine (10 mL), dried (MgSO₄) and concentrated. HPLC and LCMS analysis indicated that the desired ketone is the minor product while most of the material is the imine intermediate. The crude material was stirred in THF (150 mL) and 2 N HCl (100 mL) at room temperature for 15 h. The reaction was incomplete. Concentrated HCl (35 mL) was added. The mixture was stirred at room temperature for 1 h and at reflux for 1 h, then concentrated in vacuo. The residue was taken up in EtOAc (300 mL), washed with saturated NaHCO₃ (2×10 mL), brine (10 mL), dried (MgSO₄) and concentrated. Silica gel chromatography (EtOAc-hexanes, 0% to 10% gradient) gave the desired methyl ketone as a colorless liquid (2.18 g, 68%). MS found: $(M+Na)^+=297$.

(230b) To a solution of the ketone (2.15 g, 7.85 mmol) from reaction 230a in N,N-dimethylacetamide (100 mL) and water (15 mL) were added PdCl₂ (278 mg, 0.2 eq) and Cu(OAc)₂ (695 mg, 0.5 eq). The mixture was stirred under balloon pressure oxygen for three days, diluted with brine (100 mL) and 1 N HCl (100 mL), and extracted with EtOAc (4×100 mL). The combined extracts were washed with brine (10 mL), dried (MgSO₄) and concentrated. Silica gel chromatography (EtOAc-hexanes, 5% to 25% gradient) gave the desired diketone (2.05 g, 90%). MS found: $(M+Na)^+=313$.

(230c) Piperidine (1.37 mL, 2 eq) and HOAc (0.797 mL, 2 eq) were added to a solution of the diketone (2.02 g, 6.97 mmol) from reaction 230b in THF (20 mL). Upon heating to reflux, the resulting solid became a homogeneous solution. After 20 h at reflux, the mixture was filtered through a silica gel pad. The pad was rinsed with ether. The filtrate was concentrated. Silica gel chromatography (EtOAc-hexanes, 5% to 25% gradient) separated the desired cyclohexenone (a mixture of two diastereomers) from unreacted starting material (592 mg, 29%). The product mixture was further separated using Sunfire reverse phase HPLC (60% to 90% solvent B gradient) to give a fast eluting isomer (556.9 mg, 29%) and a slow eluting isomer (476.2 mg, 25%). MS found: $(M-EtOH+H)^+=227$ for both isomers. The fast eluting isomer proved to be the desired (R)-4-((R)-2-ethoxy-2-phenylethyl)-3,4-dimethylcyclohex-2-enone by chemical conversion to Example 36.

(230d) To a solution of the fast eluting isomer (423 mg, 1.56 mmol) from reaction 230c in ether (20 mL) was added ethyl formate (346 mg, 3 eq), sodium (500 mg, washed with hexane then ether) and ethanol (0.25 mL). The mixture was stirred for 18 h. After removing the excess sodium with a tweezers, the mixture was quenched with 1 N HCl (20 mL), brine (20 mL), and extracted with ether (3×20 mL). The combine extracts were washed with brine (5 mL), dried (MgSO₄) and filtered through a silica gel pad. The pad was rinsed with ether. The filtrate was concentrated to give the desired keto-aldehyde (469 mg, 100%), which exists as a enol form, as a red liquid.

(230e) To a solution of the enol (15.1 mg, 0.050 mmol) from reaction 230d in HOAc (2 mL) were added semicarbizide hydrochloride (6.8 mg, 1.2 eq) and sodium acetate (5.0 mg, 1.2 eq). The mixture was stirred at room temperature for 16 h and at 70° C. for 2 h, concentrated and purified by reverse phase HPLC (70% to 100% solvent B gradient) to give Example 230 as a white solid (3.9 mg, 23%). MS found: $(M+H)^+=340$.

Example 231

(R)-5-((R)-2-ethoxy-2-phenylethyl)-5,6-dimethyl-1-phenyl-4,5-dihydro-1H-indazole To a solution of the enol (22 mg, 0.073 mmol) from reaction 230d in HOAc (2 mL) was added 2-hydrazinobenzothiazole (9.5 mg, 1.2 eq). The mixture was stirred at room temperature for 7 h, concentrated and purified by silica gel chromatography (EtOAc-hexanes, 0% to 15% gradient) to give Example 231 as a yellow liquid (20.7 mg, 76%). MS found: $(M+H)^+=373$.

Example 232

(R)-5-((R)-2-ethoxy-2-phenylethyl)-1,5,6-trimethyl-4,5-dihydro-1H-indazole

A 0.06 M HOAc solution of methylhydrazine (1.6 mL, 1.2 eq) was added to the enol (24.0 mg, 0.08 mmol) from reaction 230d. The mixture was stirred at room temperature for 16 h, concentrated and purified by reverse phase HPLC (60% to 100% solvent B gradient) to give Example 232 as a colorless liquid (15.2 mg, 61%). MS found: $(M+H)^+=311$.

Example 233

3-((R)-5-((R)-2-ethoxy-2-phenylethyl)-5,6-dimethyl-4,5-dihydro-1-indazol-1-yl)-N,N-dimethylbenzamide (233a) To a solution of the enol (10.5 mg, 0.035 mmol) from reaction 230d in HOAc (2 mL) was added 3-hydrazinobenzoic acid (6.4 mg, 1.2 eq). The mixture was stirred at room temperature for 5 h and concentrated. The residue was dissolved in EtOAc (30 mL), washed with 1 N HCl (5 mL), brine (5 mL), dried ($MgSO_4$) and concentrated. The crude material was used without purification.

(233b) HOBt monohydrate (14 mg, 3 eq), EDCI hydrochloride (20 mg, 3 eq), Hunig base (0.059 mL, 10 eq) and a 2 M THF solution of dimethylamine (0.085 mL, 5 eq) were added to the crude acid from reaction 233a in acetonitrile (3 mL) at room temperature. After 15 h at room temperature, the mixture was concentrated and purified by reverse phase HPLC (70-100% solvent B gradient) to give Example 233 (2.5 mg, 16% for 2 steps) as a yellow liquid. MS Found: $(M+H)^+=444$.

Example 234

(5R)-1-(2,5-difluorophenyl)-5-((R)-2-ethoxy-2-phenylethyl)-5,6-dimethyl-4,5-dihydro-1H-indazole Using a procedure analogous to reaction Example 231, the enol (15.6 mg, 0.052 mmol) from reaction 230d was reacted with 2,5-difluorophenylhydrazine to give Example 234 (2.5 mg, 12%). MS found: $(M+Na)^+=409$.

Example 235

(5R)-1-(2,4-difluorophenyl)-5-((R)-2-ethoxy-2-phenylethyl)-5,6-dimethyl-4,5-dihydro-1H-indazole To a solution of the enol (20 mg, 0.067 mmol) from reaction 230d in HOAc (2 mL) were added 2,4-difluorophenylhydrazine hydrochloride (14.5 mg, 1.2 eq) and sodium acetate (6.6 mg, 1.2 eq). The mixture was stirred at room temperature for 7 h, concentrated and purified by silica gel chromatography (EtOAc-hexanes, 0% to 15% gradient) to give Example 235 as a yellow liquid (18.6 mg, 68%). MS found: $(M+Na)^+=409$.

Example 236

(R)-1-(3-chloro-4-fluorophenyl)-5-((R)-2-ethoxy-2-phenylethyl)-5,6-dimethyl-4,5-dihydro-1H-indazole Using a procedure analogous to Example 231, the enol (21 mg, 0.070 mmol) from reaction 230d was reacted with 3-chloro-4-fluorophenylhydrazine to give Example 236 (21.2 mg, 71%). MS found: $(M+H)^+=425$.

Example 237

(R)-5-((R)-2-ethoxy-2-phenylethyl)-5,6-dimethyl-1-(pyridin-2-yl)-4,5-dihydro-1H-indazole Using a procedure analogous to Example 235, the enol (22 mg, 0.073 mmol) from reaction 230d was reacted with 2-hydrazinopyridine dihydrochloride to give Example 237 (15.4 mg, 43%). MS found: $(M+H)^+=374$.

Example 238

(R)-1-(6-chloropyridazin-3-yl)-5-((R)-2-ethoxy-2-phenylethyl)-5,6-dimethyl-4,5-dihydro-1H-indazole Using a procedure analogous to reaction Example 231, the enol (18.4 mg, 0.060 mmol) from reaction 230d was reacted with 3-chloro-6-hydrazinopyridazine to give Example 238 (10.0 mg, 41%). MS found: $(M+Na)^+=431$.

Example 239

(5R)-5-((R)-2-ethoxy-2-phenylethyl)-1-(2-fluorophenyl)-5,6-dimethyl-4,5-dihydro-1H-indazole Using a procedure analogous to Example 235, the enol (22 mg, 0.073 mmol) from reaction 230d was reacted with 2-fluorophenylhydrazine hydrochloride to give Example 239 (3.8 mg, 13%). MS found: $(M+H)^+=391$.

Example 240

(R)-5-((R)-2-ethoxy-2-phenylethyl)-1-(3-fluorophenyl)-5,6-dimethyl-4,5-dihydro-1H-indazole Using a procedure analogous to Example 235, the enol (22 mg, 0.073 mmol) from reaction 230d was reacted with 3-fluorophenylhydrazine hydrochloride to give Example 240 (3.2 mg, 11%). MS found: $(M+H)^+=391$.

What is claimed is:
1. A compound having the formula

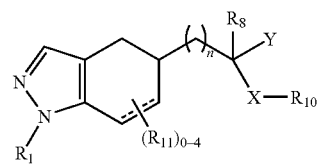

II or a pharmaceutically acceptable salt thereof, wherein:
n is 0, 1 or 2;
X is a bond;
Y is $OR_{12}$;
$R_1$ is phenyl substituted with 1-3 groups independently selected from H and halogen;
$R_8$ is hydrogen;
$R_{10}$ is optionally substituted phenyl or optionally substituted naphthyl, each group of which is optionally substituted by one up to the maximum number of substitutable positions with a substituent independently selected from halogen, CN, $NR_dR_e$, $C_{1-6}$alkyl, OH, $OC_{1-6}$alkyl, $OCF_3$, $CF_3$, —O(optionally substituted phenyl), or —O(optionally substituted benzyl);

$R_d$ and $R_e$ are independently selected (i) from hydrogen, $C_{1-6}$alkyl, and substituted $C_{1-6}$alkyl; or (ii) $R_d$ is taken together with $R_e$ to form a heteroaryl or heterocyclo ring;

each $R_{11b}$ is independently selected from H, $C_{1-6}$alkyl, substituted $C_{1-6}$alkyl, acetylenyl, CN, Cl and $C_{3-6}$cycloalkyl; and $R_{12}$ is hydrogen, or $C_{1-6}$alkyl or $C_{2-6}$ alkenyl.

2. A compound of formula IV:

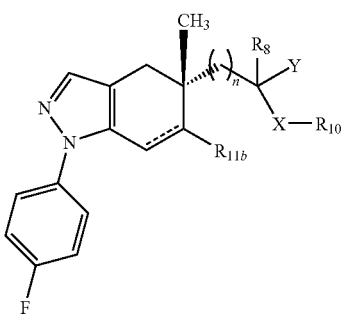

IV or a pharmaceutically acceptable salt thereof, wherein:
X is a bond;
Y is —$OC_{1-6}$alkyl or —$OC_{2-6}$alkenyl;
$R_8$ is hydrogen;
$R_{10}$ is an optionally substituted phenyl group;
$R_{11b}$ is hydrogen, acetylenyl, cyano, chloro, or $C_{1-6}$alkyl; and
n is 1.

3. A compound of formula IV:

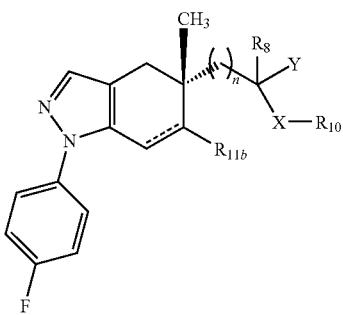

IV or a pharmaceutically acceptable salt thereof, wherein:
X is —NH—;
Y is taken together with $R_8$ to form oxo;
$R_{10}$ is an optionally substituted five-membered heteroaryl group;
$R_{11b}$ is $C_{1-6}$alkyl; and
n is 2.

4. A compound selected from:
(i)
Example 1 (2-[(5R)-1-(4-fluorophenyl)-5,6-dimethyl-4,5-dihydro-1H-indazol-5-yl]-1-phenylethanol);

Example 2 (2-[(5R)-1-(4-fluorophenyl)-5,6-dimethyl-4,5-dihydro-1H-indazol-5-yl]-1-phenylethanol);

Example 3 (1-(4-fluorophenyl)-2-[(5R)-1-(4-fluorophenyl)-5,6-dimethyl-4,5-dihydro-1H-indazol-5-yl]ethanol);

Example 4 (1-(4-fluorophenyl)-2-[(5R)-1-(4-fluorophenyl)-5,6-dimethyl-4,5-dihydro-1H-indazol-5-yl]ethanol);

Example 5 (2-[(5R)-1-(4-fluorophenyl)-5,6-dimethyl-4,5-dihydro-1H-indazol-5-yl]1-[4-(methyloxy)phenyl]ethanol);

Example 6 (2-[(5R)-1-(4-fluorophenyl)-5,6-dimethyl-4,5-dihydro-1H-indazol-5-yl]-1-[4-(methyloxy)pheny]ethanol);

Example 11 (2-[(5R)-1-(4-fluorotophenyl)-5,6-dimethyl-4,5-dihydro-1H-indazol-5-yl]-1-naphthalen-1-ylethanol);

Example 12 (2-[(5R)-1-(4-fluorophenyl)-5,6-dimethyl-4,5-dihydro-1H-indazol-5-yl]-1-naphthalen-1-ylethanol);

Example 13 (2-[(5R)-1-(4-fluorophenyl)-5,6-dimethyl-4,5-dihydro-1H-indazol-5-yl]-1-naphthalen-2-ylethanol);

Example 14 (2-[(5R)-1-(4-fluorophenyl)-5,6-dimethyl-4,5-dihydro-1H-indazol-5-yl]-1-naphthalen-2-ylethanol);

Example 35 ((5R)-1-(4-fluorophenyl)-5-(2-methoxy-2-phenylethyl)-5,6-dimethyl-4,5-dihydro-1H-indazole);

Example 36 ((5R)-5-(2-ethoxy-2-phenylethyl)-1-4-fluorophenyl)-5,6-dimethyl-4,5-dihydro-1H-indazole);

Example 37 ((5R)-5-(2-(benzyloxy)-2-phenylethyl)-1-(4-fluorophenyl)-5,6-dimethyl-4,5-dihydro-1H-indazole);

Example 38 ((5R)-1-(4-fluorophenyl)-5,6-dimethyl-5-(2-phenyl-2-propoxyethyl)-4,5-dihydro-1H-indazole);

Example 39 ((5R)-5-(2-(allyloxy)-2-phenylethyl)-1-(4-fluorophenyl)-5,6-dimethyl-4,5-dihydro-1H-indazole);

Example 41 ((5R)-1-(4-fluorophenyl)-5-(2-isopropoxy-2-phenylethyl)-5,6-dimethyl-4,5-dihydro-1H-indazole);

Example 43 ((5R)-1-(4-fluorophenyl)-5-(2-methoxy-2-(naphthalen-1-yl)ethyl)-5,6-dimethyl-4,5-dihydro-1H-indazole);

Example 44 ((5R)-1-(4-fluorophenyl)-5-(2-methoxy-2-(naphthalen-1-yl)ethyl)-5,6-dimethyl-4,5-dihydro-1H-indazole);

Example 45 ((5R)-1-(4-fluorophenyl)-5-(2-(4-fluorophenyl)-2-methoxyethyl)-5,6-dimethyl-4,5-dihydro-1H-indazole);

Example 46 ((5R)-5-(2-ethoxy-2-(4-fluorophenyl)ethyl)-1-(4-fluorophenyl)-5,6-dimethyl-4,5-dihydro-1H-indazole);

Example 48 (1-(biphenyl-3-yl)-2-((R)-1-(4-fluorophenyl)-5,6-dimethyl-4,5-dihydro-1H-indazol-5-yl)ethanol);

Example 49 (1-(biphenyl-3-yl)-2-((R)-1-(4-fluorophenyl)-5,6-dimethyl-4,5-dihydro-1H-indazol-5-yl)ethanol);

Example 50 (2-((R)-1-(4-fluorophenyl)-5,6-dimethyl-4,5-dihydro-1H-indazol-5-yl)-1-m-tolylethanol);

Example 51 (2-((R)-1-(4-fluorophenyl)-5,6-dimethyl-4,5-dihydro-1H-indazol-5-yl)-1-m-tolylethanol);

Example 52 ((5R)-5-(2-ethoxy-2-m-tolylethyl)-1-(4-fluorophenyl)-5,6-dimethyl-4,5-dihydro-1H-indazole);

Example 53 (1-(3-fluorophenyl)-2-((R)-1-(4-fluorophenyl)-5,6-dimethyl-4,5-dihydro-1H-indazol-5-yl)ethanol);

Example 54 (1-(3-fluorophenyl)-2-((R)-1-(4-fluorophenyl)-5,6-dimethyl-4,5-dihydro-1H-indazol-5-yl)ethanol);

Example 55 ((5R)-5-(2-ethoxy-2-(3-fluorophenyl)ethyl)-1-(4-fluorophenyl)-5,6-dimethyl-4,5-dihydro-1H-indazole);

Example 56 (2-((R)-1-(4-fluorophenyl)-5,6-dimethyl-4,5-dihydro-1H-indazol-5-yl)-1-(2-methoxyphenyl) ethanol);

Example 57 (2-((R)-1-(4-fluorophenyl)-5,6-dimethyl-4,5-dihydro-1H-indazol-5-yl)-1-(2-methoxyphenyl)ethanol);

Example 58 ((5R)-1-(4-fluorophenyl)-5-(2-methoxy-2-(2-methoxyphenyl)ethyl)-5,6-dimethyl-4,5-dihydro-1H-indazole);

Example 59 (2-((R)-1-(4-fluorophenyl)-5,6-dimethyl-4,5-dihydro-1H-indazol-5-yl)-1-o-tolylethanol);

Example 60 (2-((R)-1-(4-fluorophenyl)-5,6-dimethyl-4,5-dihydro-1H-indazol-5-yl)-1-o-tolylethanol);

Example 61 ((5R)-1-(4-fluorophenyl)-5-(2-methoxy-2-o-tolylethyl)-5,6-dimethyl-4,5-dihydro-1H-indazole);

Example 62 ((5R)-1-(4-fluorophenyl)-5-(2-methoxy-2-o-tolylethyl)-5,6-dimethyl-4,5-dihydro-1H-indazole);

Example 63 ((5R)-5-(2-ethoxy-2-o-tolylethyl)-1-(4-fluorophenyl)-5,6-dimethyl-4,5-dihydro-1H-indazole);

Example 64 ((5R)-1-(4-fluorophenyl)-5-(2-methoxy-2-o-tolylethyl)-5,6-dimethyl-4,5,6,7-tetrahydro-1H-indazole);

Example 65 (2-((R)-1-(4-fluorophenyl)-5,6-dimethyl-4,5-dihydro-1H-indazol-5-yl)-1-(3-methoxyphenyl)ethanol);

Example 66 (2-((R)-1-(4-fluorophenyl)-5,6-dimethyl-4,5-dihydro-1H-indazol-5-yl)-1-(3-methoxyphenyl)ethanoly Example 81 (2-((R)-1-(4-fluorophenyl)-5,6-dimethyl-4,5-dihydro-1H-indazol-5-yl)-1-(pyridin-3-yl)ethanol);

Example 82 (1-(2,6-dimethylphenyl)-2-((R)-1-(4-fluorophenyl)-5,6-dimethyl-4,5-dihydro-1H-indazol-5-yl) ethanol);

Example 83 (1-(2,6-dimethylphenyl)-2-((R)-1-(4-fluorophenyl)-5,6-dimethyl-4,5-dihydro-1H-indazol-5-yl) ethanol);

Example 84 (2-((R)-1-(4-fluorophenyl)-5,6-dimethyl-4,5-dihydro-1H-indazol-5-yl)-1-(2-methylnaphthalen-1-yl) ethanol);

Example 85 (2-((R)-1-(4-fluorophenyl)-5,6-dimethyl-4,5-dihydro-1H-indazol-5-yl)-1-(2-methylnaphthalen-1-yl) ethanol);

Example 86 (2-((R)-1-(4-fluorophenyl)-5,6-dimethyl-4,5-dihydro-1H-indazol-5-yl)-1-(2-methoxynaphthalen-1-yl)ethanol);

Example 87 (2-((R)-1-(4-fluorophenyl)-5,6-dimethyl-4,5-dihydro-1H-indazol-5-yl)-1-(2-methoxynaphthalen-1-yl)ethanol);

Example 88 (1-(2,6-dimethoxyphenyl)-2-((R)-1-(4-fluorophenyl)-5,6-dimethyl-4,5-dihydro-1H-indazol-5-yl) ethanol);

Example 89 (1-(2,6-dimethoxyphenyl)-2(((R)-1-(4-fluorophenyl)-5,6-dimethyl-4,5-dihydro-1H-indazol-5-yl) ethanol);

Example 92 (2-((R)-1-(4-fluorophenyl)-5,6-dimethyl-4,5-dihydro-1H-indazol-5-yl)-1-(2-(pyrrolidin-1-ylmethyl) phenyl)ethanol);

Example 93 (2-((R)-1-(4-fluorophenyl)-5,6-dimethyl-4,5-dihydro-1H-indazol-5-yl)-1 -(2-(pynolidin-1-ylmethyl) phenyl)ethanol);

Example 94 (2-((R)-1-(4-fluorophenyl)-5,6-dimethyl-4,5-dihydro-1H-indazol-5-yl)-1-(2-(morpholinomethyl) phenyl)ethanol);

Example 96 (1-(2-chlorophenyl)-2-((R)-1-(4-fluorophenyl)-5,6-dimethyl-4,5-dihydro-1H-indazol-5-yl)ethanol);

Example 97 (1-(2-chlorophenyl)-2-((R)-1-(4-fluorophenyl)-5,6-dimethyl-4,5-dihydro-1H-indazol-5-yl)ethanol);

Example 98 ((5R)-5-(2-(2-chlorophenyl)-2-ethoxyethyl)-1-(4-fluorophenyl)-5,6-dimethyl-4,5-dihydro-1H-indazole);

Example 115 (2-((5R)-1-(4-fluorophenyl)-5,6-dimethyl-4,5,6,7-tetrahydro-1H-indazol-5-yl)-1-phenylethanol);

Example 116 ((5R)-5-(2-ethoxy-2-phenylethyl)-1-(4-fluorophenyl)-5,6-dimethyl-4,5,6,7-tetrahydro-1H-indazole);

Example 117 (2-(1-(4-fluorophenyl)-5-methyl-4,5,6,7-tetrahydro-1H-indazol-5-yl)-1-phenylethanol);

Example 118 (2-(1-(4-fluorophenyl)-5-methyl-4,5,6,7-tetrahydro-1H-indazol-5-yl)-1 -phenylethanol);

Example 119 (5-(2-ethoxy-2-phenylethyl)-1-(4-fluorophenyl)-5-methyl-4,5,6,7-tetrahydro-1H-indazole);

Example 120 (5-(2-ethoxy-2-phenylethyl)-1-(4-fluorophenyl)-5-methyl-4,5,6,7-tetrahydro-1H-indazole);

Example 127 (5R)-5-(2-ethoxy-2-phenylethyl)-6-ethyl-1-(4-fluorophenyl)-5-methyl -4,5-dihydro-1H-indazole);

Example 128 ((5R)-6-(difluoromethyl)-5-(2-ethoxy-2-phenylethyl)-1-(4-fluorophenyl)-5-methyl-4,5-dihydro-1H-indazole);

Example 129 (2-(1-(4-fluorophenyl)-5-methyl-4,5-dihydro-1H-indazol-5-yl)-1-phenylethanol);

Example 130 (2-(1-(4-fluorophenyl)-5-methyl-4,5-dihydro-1H-indazol-5-yl)-1-phenylethanol);

Example 131 (2-(1-(4-fluorophenyl)-5-methyl-4,5-dihydro-1H-indazol-5-yl)-phenylethanol);

Example 132 (5-(2-ethoxy-2-phenylethyl)-1-(4-fluorophenyl)-5-methyl-4,5-dihydro-1H-indazole);

Example 133 (5-(2-ethoxy-2-phenylethyl)-1-(4-fluorophenyl)-5-methyl-4,5-dihydro-1H-indazole);

Example 134 (5-(2-ethoxy-2-phenylethyl)-1-(4-fluorophenyl)-5-methyl-4,5-dihydro-1H-indazole);

Example 144 ((R)—((S)-1-(4-fluorophenyl)-5,6-dimethyl-4,5-dihydro-1H-indazol-5-yl)(phenyl)methanol);

Example 175 (5-((R)-2-ethoxy-2-phenylethyl)-1-(4-fluorophenyl)-5-methyl-4,5-dihydro-1H-indazole);

Example 177 (5-((R)-2-ethoxy-2-phenylethyl)-6-ethynyl-1-(4-fluorophenyl)-5-methyl-4,5-dihydro-1H-indazole);

Example 179 (5-((R)-2-ethoxy-2-phenylethyl)-1-(4-fluorophenyl)-5-methyl-4,5-dihydro-1H-indazole-6-carbonitrile);

Example 180 (6-chloro-5-((R)-2-ethoxy-2-phenylethyl)-1-(4-fluorophenyl)-5-methyl-4,5-dihydro-1H-indazole);

Example 234 ((5R)-1-(2,5-difluorophenyl)-5-((R)-2-ethoxy-2-phenylethyl)-5,6-dimethyl-4,5-dihydro-1H-indazole); or Example 235 ((5R)-1-(2,4-difluorophenyl)-5-((R)-2-ethoxy-2-phenylethyl)-5,6-dimethyl-4,5-dihydro-1H-indazole);

Example 236 ((R)-1-(3-chloro-4-fluorophenyl)-5-((R)-2-ethoxy-2-phenylethyl)-5,6-dimethyl-4,5-dihydro-1H-indazole);

Example 239 ((5R)-5-((R)-2-ethoxy-2-phenylethyl)-1-(2-fluorophenyl)-5,6-dimethyl-4,5-dihydro-1H-indazole); and Example 240 ((R)-5-((R)-2-ethoxy-2-phenylethyl)-1-(3-fluorophenyl)-5,6-dimethyl-4,5-dihydro-1H-indazole); or (ii) a pharmaceutically acceptable salt of (i) thereof.

5. A compound according to claim 4 selected from:
(i) Example 1 (2-[(5R)- 1 -(4-fluorophenyl)-5,6-dimethyl-4, 5-dihydro-1H-indazol-5-yl]-1 -phenylethanol);

Example 2 (2-[(5R)-1-(4-fluorophenyl)-5,6-dimethyl-4,5-dihydro-1H-indazol-5-yl]1-1-phenylethanol);

Example 3 (1-(4-fluorophenyl)-2-[(5R)-1-(4-fluorophenyl)-5,6-dimethyl-4,5-dihydro-1H-indazol-5-yl]ethanol);

Example 4 (1-(4-fluorophenyl)-2-[(5R)-1-(4-fluorophenyl)-5,6-dimethyl-4,5-dihydro-1H-indazol-5-yl]ethanol);

Example 5 (2-[(5R)-1-(4-fluorophenyl)-5,6-dimethyl-4,5-dihydro-1H-indazol-5-yl]1-[4-(methyloxy)phenyl]ethanol);

Example 11 (2-[(5R)-1-(4-fluorophenyl)-5,6-dimethyl-4, 5-dihydro-1H-indazol-5-yl]-1-naphthalen-1-ylethanol);

Example 12 (2-[(5R)-1-(4-fluorophenyl)-5,6-dimethyl-4, 5-dihydro-1H-indazol-5-yl]-1 -naphthalen-1-ylethanol);

Example 14 (2-[(5R)-1-(4-fluorophenyl)-5,6-dimethyl-4, 5-dihydro-1H-indazol-5-yl]-1-naphthalen-2-ylethanol);

Example 35 ((5R)-1-(4-fluorophenyl)-5-(2-methoxy-2-phenylethyl)-5,6-dimethyl-4,5-dihydro-1H-indazole);

Example 36 ((5R)-5-(2-ethoxy-2-phenylethyl)-1-(4-fluorophenyl)-5,6-dimethyl-4,5-dihydro-1H-indazole);

Example 37 ((5R)-5-(2-(benzyloxy)-2-phenylethyl)-1-(4-fluorophenyl)-5,6-dimethyl-4,5-dihydro-1H-indazole);

Example 38 ((5R)-1-(4-fluorophenyl)-5,6-dimethyl-5-(2-phenyl-2-propoxyethyl)-4,5-dihydro-1H-indazole);

Example 39 ((5R)-5-(2-(allyloxy)-2-phenylethyl)-1-(4-fluorophenyl)-5,6-dimethyl-4,5-dihydro-1H-indazole);

Example 41 ((5R)-1-(4-fluorophenyl)-5-(2-isopropoxy-2-phenylethyl)-5,6-dimethyl-4,5-dihydro-1H-indazole);

Example 43 ((5R)-1 -(4-fluorophenyl)-5-(2-methoxy-2-(naphthalen-1-yl)ethyl)-5,6-dimethyl-4,5-dihydro-1H-indazole);

Example 44 ((5R)-1-(4-fluorophenyl)-5-(2-methoxy-2-(naphthalen-1-yl)ethyl)-5,6-dimethyl-4,5-dihydro-1H-indazole);

Example 45 ((5R)-1-(4-fluorophenyl)-5-(2-(4-fluorophenyl)-2-methoxyethyl)-5,6-dimethyl-4,5-dihydro-1H-indazole);

Example 46 ((5R)-5-(2-ethoxy-2-(4-fluorophenyl)ethyl)-1-(4-fluorophenyl)-5,6-dimethyl-4,5-dihydro-1H-indazole);

Example 48 (1-(biphenyl-3-yl)-2-((R)-1-(4-fluorophenyl)-5,6-dimethyl-4,5-dihydro-1H-indazol-5-yl)ethanol);

Example 49 (1-(biphenyl-3-yl)-2-((R)-1(4-fluorophenyl)-5,6-dimethyl-4,5-dihydro-1H-indazol-5-yl)ethanol);

Example 50 (2-((R)-1-(4-fluorophenyl)-5,6-dimethyl-4,5-dihydro-1H-indazol-5-yl)-1-m-tolylethanol);

Example 51 (2-((R)-1-(4-fluorophenyl)-5,6-dimethyl-4,5-dihydro-1H-indazol-5-yl)-1-m-tolylethanol);

Example 52 ((5R)-5-(2-ethoxy-2-m-tolylethyl)-1-(4-fluorophenyl)-5,6-dimethyl-4,5-dihydro-1H-indazole);

Example 53 (1-(3-fluorophenyl)-2-((R)-1-(4-fluorophenyl)-5,6-dimethyl-4,5-dihydro-1H-indazol-5-yl)ethanol);

Example 54 (1-(3-fluorophenyl)-2-((R)-1-(4-fluorophenyl)-5,6-dimethyl-4,5-dihydro-1H-indazol-5-yl)ethanol);

Example 55 ((5R)-5-(2-ethoxy-2-(3-fluorophenyl)ethyl)-1-(4-fluorophenyl)-5,6-dimethyl-4,5-dihydro-1H-indazole);

Example 56 (2-((R)-1-(4-fluorophenyl)-5,6-dimethyl-4,5-dihydro-1H-indazol-5-yl)-1-(2-methoxyphenyl)ethanol);

Example 57 (2-((R)-1-(4-fluorophenyl)-5,6-dimethyl-4,5-dihydro-1H-indazol-5-yl)-1-(2-methoxyphenyl)ethanol);

Example 58 ((5R)-1-(4-fluorophenyl)-5-(2-methoxy-2-(2-methoxyphenypethyl)ethyl)-5,6-dimethyl-4,5-dihydro-1H-indazole);

Example 59 (2-((R)-1-(4-fluorophenyl)-5,6-dimethyl-4,5-dihydro-1H-indazol-5-yl)-1-o-tolylethanol);

Example 60 (2-((R)-1-(4-fluorophenyl)-5,6-dimethyl-4,5-dihydro-1H-indazol-5-yl)-1 -o-tolylethanol);

Example 61 ((5R)-1-(4-fluorophenyl)-5-(2-methoxy-2-o-tolylethyl)-5,6-dimethyl-4,5-dihydro-1H-indazole);

Example 62 ((5R)-1-(4-fluorophenyl)-5-(2-methoxy-2-o-tolylethyl)-5,6-dimethyl-4,5-dihydro-1H-indazole);

Example 63 ((5R)-5-(2-ethoxy-2-o-tolylethyl)-1-(4-fluorophenyl)-5,6-dimethyl-4,5-dihydro-1H-indazole);

Example 65 (2-((R)-1-(4-fluorophenyl)-5,6-dimethyl-4,5-dihydro-1H-indazol-5-yl)-1-(3-methoxyphenyl)ethanol);

Example 66 (2-((R)-1-(4-fluorophenyl)-5,6-dimethyl-4,5-dihydro-1H-indazol-5-yl)-1-(3-methoxyphenyl)ethanolv Example 81 (2-((R)-1-(4-fluorophenyl)-5,6-dimethyl-4,5-dihydro-1H-indazol-5-yl)-1-(pyridin-3-yl)ethanol);

Example 82 (1-(2,6-dimethylphenyl)-2-((R)-1-(4-fluorophenyl)-5,6-dimethyl-4,5-dihydro-1H-indazol-5-yl)ethanol);

Example 83 (1-(2,6-dimethylphenyl)-2-((R)-1-(4-fluorophenyl)-5,6-dimethyl-4,5-dihydro-1H-indazol-5-yl)ethanol);

Example 84 (2-((R)-1-(4-fluorophenyl)-5,6-dimethyl-4,5-dihydro-1H-indazol-5-yl)-1-(2-methylnaphthalen-1-yl)ethanol);

Example 85 (2((R)-1-(4-fluorophenyl)-5,6-dimethyl-4,5-dihydro-1H-indazol-5-yl)-1-(2-methylnaphthalen-1-yl)ethanol);

Example 86 (2-((R)-1-(4-fluorophenyl)-5,6-dimethyl-4,5-dihydro-1H-indazol-5-yl)-1-(2-methoxynaphthalen-1 -yl)ethanol);

Example 87 (2-((R)-1-(4-fluorophenyl)-5,6-dimethyl-4,5-dihydro-1H-indazol-5-yl)-1-(2-methoxynaphthalen-1-yl)ethanol);

Example 89 (1-(2,6-dimethoxyphenyl)-2-((R)-1-(4-fluorophenyl)-5,6-dimethyl-4,5-dihydro-1H-indazol-5-yl)ethanol);

Example 96 (1-(2-chlorophenyl)-2-((R)-1-(4-fluorophenyl)-5,6-dimethyl-4,5-dihydro-1H-indazol-5-yl)ethanol);

Example 97 (1-(2-chlorophenyl)-2-((R)-1-(4-fluorophenyl)-5,6-dimethyl-4,5-dihydro-1H-indazol-5-yl)ethanol);

Example 98 ((5R)-5-(2-(2-chlorophenyl)-2-ethoxyethyl)-1-(4-fluorophenyl)-5,6-dimethyl-4,5-dihydro-1H-indazole);

Example 116 ((5R)-5-(2-ethoxy-2-phenylethyl)-1-(4-fluorophenyl)-5,6-dimethyl-4,5,6,7-tetrahydro-1H-indazole);

Example 127 (5R)-5-(2-ethoxy-2-phenylethyl)-6-ethyl-1-(4-fluorophenyl)-5-methyl-4,5-dihydro-1H-indazole);

Example 128 ((5R)-6-(difluoromethyl)-5-(2-ethoxy-2-phenylethyl)-1-(4-fluorophenyl)-5-methyl-4,5-dihydro-1H-indazole);

Example 132 (5-(2-ethoxy-2-phenylethyl)-1-(4-fluorophenyl)-5-methyl-4,5-dihydro-1H-indazole);

Example 175 (5-((R)-2-ethoxy-2-phenylethyl)-1-(4-fluorophenyl)-5-methyl-4,5-dihydro-1H-indazole);
Example 177 (5-((R)-2-ethoxy-2-phenylethyl)-6-ethynyl-1-(4-fluorophenyl)-5-methyl-4,5-dihydro-1H-indazole);
Example 179 (5-((R)-2-ethoxy-2-phenylethyl)-1-(4-fluorophenyl)-5-methyl-4,5-dihydro-1H-indazole-6-carbonitrile);
Example 180 (6-chloro-5-((R)-2-ethoxy-2-phenylethyl)-1-(4-fluorophenyl)-5-methyl-4,5-dihydro-1H-indazole);
Example 234 ((5R)-1-(2,5-difluorophenyl)-5-((R)-2-ethoxy-2-phenylethyl)-5,6-dimethyl-4,5-dihydro-1H-indazole);
Example 235 ((5R)-1-(2,4-difluorophenyl)-5-((R)-2-ethoxy-2-phenylethyl)-5,6-dimethyl-4,5-dihydro-1H-indazole);
Example 236 ((R)-1-(3-chloro-4-fluorophenyl)-5-((R)-2-ethoxy-2-phenylethyl)-5,6-dimethyl-4,5-dihydro-1H-indazole);
Example 239 ((5R)-5-((R)-2-ethoxy-2-phenylethyl)-1-(2-fluorophenyl)-5,6-dimethyl-4,5-dihydro-1H-indazole); and
Example 240 ((R)-5-((R)-2-ethoxy-2-phenylethyl)-1-(3-fluorophenyl)-5,6-dimethyl-4,5-dihydro-1H-indazole); or (ii) a pharmaceutically acceptable salt of (i) thereof.

6. A pharmaceutical composition comprising a compound as defined in claim 1 and a pharmaceutically acceptable carrier therefor.

* * * * *

UNITED STATES PATENT AND TRADEMARK OFFICE
CERTIFICATE OF CORRECTION

PATENT NO.        : 7,888,381 B2                                           Page 1 of 1
APPLICATION NO.   : 11/451660
DATED             : February 15, 2011
INVENTOR(S)       : Jingwu Duan et al.

It is certified that error appears in the above-identified patent and that said Letters Patent is hereby corrected as shown below:

In the Claims:

Claim 1:

Column 94, lines 46 to 51, change

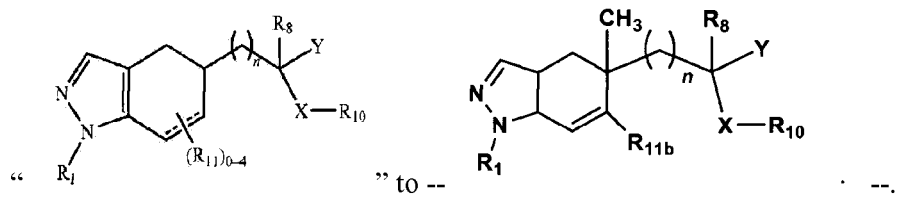

Column 95, line 1, change "$R_4$" to -- $R_d$ --.

Claim 2:

Column 95, line 31, change "$R_{1/b}$" to -- $R_{11b}$ --.

Claim 4:

Column 96, line 8, change "pheny]" to -- phenyl] --.

Column 96, line 24, change "-4-" to -- -(4- --.

Column 97, line 53, change "2(((R)" to -- 2((R) --.

Column 98, line 31, change "-phenylethanol)" to -- -1-phenylethanol) --.

Claim 5:

Column 99, line 5, change "yl]1-1" to yl]-1 --.

Column 99, line 13, change "yl]1" to -- yl]-1 --.

Column 100, line 8, change "methoxyphenypethyl)" to -- methoxyphenyl) --.

Signed and Sealed this
Twenty-second Day of November, 2011

David J. Kappos
*Director of the United States Patent and Trademark Office*